US010011630B2

(12) United States Patent
Vernejoul et al.

(10) Patent No.: US 10,011,630 B2
(45) Date of Patent: Jul. 3, 2018

(54) CYCLIC DINUCLEOTIDES FOR CYTOKINE INDUCTION

(71) Applicant: INVIVOGEN, Toulouse (FR)

(72) Inventors: Fabienne Vernejoul, Toulouse (FR); Gerard Tiraby, Toulouse (FR); Thierry Lioux, Balma (FR)

(73) Assignee: INVIVOGEN, Toulouse (FR)

( * ) Notice: Subject to any disclaimer, the term of this patent is extended or adjusted under 35 U.S.C. 154(b) by 239 days.

(21) Appl. No.: 15/034,335

(22) PCT Filed: Sep. 9, 2015

(86) PCT No.: PCT/EP2015/070635
§ 371 (c)(1),
(2) Date: May 4, 2016

(87) PCT Pub. No.: WO2016/096174
PCT Pub. Date: Jun. 23, 2016

(65) Prior Publication Data
US 2016/0362441 A1 Dec. 15, 2016

(30) Foreign Application Priority Data
Dec. 16, 2014 (EP) .................................... 14307054

(51) Int. Cl.
C07H 21/04 (2006.01)
A61K 31/7084 (2006.01)
C07H 21/00 (2006.01)
C07H 21/02 (2006.01)

(52) U.S. Cl.
CPC ......... *C07H 21/04* (2013.01); *A61K 31/7084* (2013.01); *C07H 21/00* (2013.01); *C07H 21/02* (2013.01)

(58) Field of Classification Search
None
See application file for complete search history.

(56) References Cited

U.S. PATENT DOCUMENTS

| | | |
|---|---|---|
| 2007/0281897 A1 | 12/2007 | Karaolis |
| 2014/0205653 A1 | 7/2014 | Dubensky, Jr. et al. |
| 2014/0219961 A1 | 8/2014 | Jung et al. |
| 2014/0329889 A1 | 11/2014 | Vance et al. |
| 2015/0056224 A1 | 2/2015 | Dubensky, Jr. et al. |

FOREIGN PATENT DOCUMENTS

| | | | |
|---|---|---|---|
| CN | 103908468 A | 7/2014 | |
| EP | 2 674 170 A1 | 12/2013 | |
| EP | 3 135 290 A1 | 3/2017 | |
| WO | 2013/185052 A1 | 12/2013 | |
| WO | 2014/099824 A1 | 6/2014 | |
| WO | 2014/179335 A1 | 11/2014 | |
| WO | 2014/189805 A1 | 11/2014 | |
| WO | WO-2014189805 A1 * | 11/2014 | ............. C07H 21/02 |
| WO | 2015/0747354 A1 | 5/2015 | |

OTHER PUBLICATIONS

Yildiz, S. et al., "Enhanced Immunostimulatory Activity of Cyclic Dinucleotides on Mouse Cells When Complexed With a Cell-Penetrating Peptide or Combined with CpG," Eur. J. Immunol., 2015, pp. 1170-1179.

Sato, Y. et al., "A pH-Sensitive Cationic Lipid Facilitates the Delivery of Liposomal siRNA and Gene Silencing Activity In Vitro and In Vivo," Journal of Controlled Release, 163, 2012, pp. 267-276.

Nakamura, T. et al., "Liposomes Loaded with a STING Pathway Ligand, Cyclic di-GMP, Enhance Cancer Immunotherapy Against Metastatic Melanoma," Journal of Controlled Release, 216, 2015, pp. 149-157.

"InvivoGen Insight," http://www.invivogen.com/docs/insight201402.pdf, Feb. 2014, pp. 1-3.

Shanahan, C. et al., "Differential Analogue Binding by Two Classes of c-di-GMP Riboswitches," Journal of the American Chemical Society, 133, 2011, pp. 15578-15592.

Gao, P. et al., "Cyclic [G(2',5')pA(3',5')p] Is the Metazoan Second Messenger Produced by DNA-Activated Cyclic GMP-AMP Synthase," Cell, 153, May 23, 2013, pp. 1094-1107.

Takafumi Tezuka et al.: "Synthesis of 2'-Modified Cyclic Bis(3'-5')diadenylic Acids (c-di-AMPs) and Their Promotion of Cell Division in a Freshwater Green Alga", Chemistry Letters, vol. 41, No. 12, Dec. 8, 2012 (Dec. 8, 2012), pp. 1723-1725, XP055172477, ISSN: 0366-7022, DOI: 10.1246/cl.2012.1723 the whole document p. 1723.

Carly A. Shanahan et al.: "Identification of c-di-GMP Derivatives Resistant to an EAL Domain Phosphodiesterase", Biochemistry, vol. 52, No. 2, Jan. 15, 2013 (Jan. 15, 2013), pp. 365-377, XP055172476, ISSN: 0006-2960, DOI: 10.1021/bi301510v cited in the application abstract p. 369; figure 3; compounds of c-di-2'F-GMP "Enzymataic Hydrolysis of Analogues containing ribose modifications" p. 370, left-hand column, last paragraph—right-hand column, paragraph first.

(Continued)

*Primary Examiner* — Travis C McIntosh, III

(74) *Attorney, Agent, or Firm* — Young & Thompson

(57) ABSTRACT

A cyclic dinucleotide compound of Formula (I):

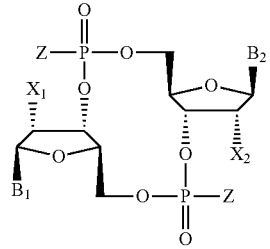

Formula (I)

wherein $X_1$ is H or F; $X_2$ is H or F; at least one among $X_1$ and $X_2$ is a fluorine atom; Z is OH, $OR_1$, SH or $SR_1$, wherein: $R_1$ is Na or $NH_4$, or $R_1$ is an enzyme-labile group which provides OH or SH in vivo such as pivaloyloxymethyl; $B_1$ and $B_2$ are bases chosen from Adenine, Hypoxanthine or Guanine, and $B_1$ is a different base than $B_2$ and a pharmaceutically acceptable salt thereof. Pharmaceutical compositions including the cyclic dinucleotide, as well as their use in the treatment of a bacterial infection, a viral infection or a cancer are also described.

14 Claims, 12 Drawing Sheets

(56) References Cited

OTHER PUBLICATIONS

Benjamin T. Roembke et al.: "A cyclic dinucleotide containing 2-aminopurine is a general fluorescent sensor to c-di-GMP and 3',3'-cGAMP", Molecular Biosystems, vol. 10, No. 6, Mar. 28, 2014 (Mar. 28, 2014), p. 1568, XP055172186, ISSN: 1742-206X, DOI: 10.1039/c3mb70518th abstract p. 1569; figure 1; compound 1.

Lingyin Li et al: "Hydrolysis of 2'3'-cGAMP by ENPPI and design of nonhydrolyzable analogs", Nature Chemical Biology, vol. 10, No. 12, Oct. 26, 2014 (Oct. 26, 2014), pp. 1043-1048, XP055172172, ISSN: 1552-4550, DOI: 10.1038/nchembio.1661 cited in the application abstract p. 1043, left-hand column; figure 4; compounds 4-6 Form.

International Search Report, dated Nov. 23, 2015, from corresponding PCT application.

\* cited by examiner

CYCLIC DINUCLEOTIDES FOR CYTOKINE INDUCTION

FIELD OF THE INVENTION

The present invention is in the field of immunotherapy. It concerns cyclic dinucleotides (CDNs) of Formulas I, II and III. In particular, it concerns fluorinated deoxyribo-CDNs and pharmaceutically acceptable salts and prodrugs thereof, which are able to induce production of Type I interferons in human and animal cells. The cytokine-induction activity of these cyclic dinucleotides requires the presence of the eukaryotic cellular receptor stimulator of interferon genes (STING), as demonstrated in vitro.

BACKGROUND OF THE INVENTION

Cytokine Induction Immunotherapy

Immunotherapy is a rapidly expanding area of medical treatment in which a patient's immune system is deliberately activated, suppressed or otherwise modulated for therapeutic benefit. Immunotherapy agents include cells, antigens (e.g. fragments of bacteria or viruses), antibodies, nucleic acids, peptides, proteins, naturally occurring ligands and synthetic molecules. Cytokines are small glycoprotein messengers known chiefly for their role in orchestrating immune response through complex signaling networks, although they also perform non-immune functions. They have been extensively explored as immunotherapy agents. However, direct administration of cytokines as immunotherapy is limited by numerous factors, including the very short half-life of cytokines in blood, which must be compensated for with frequent dosing and high doses. One highly promising immunotherapy approach is cytokine induction, whereby the patient is treated with an immunomodulatory agent that triggers the production of one or more therapeutically beneficial cytokines in their body as needed.

STING, Cytokines and Immune Response

A major player in physiological production of cytokines is stimulator of interferon genes (STING; also known as ERIS, MITA, MPYS, or TM173), a transmembrane receptor protein that is paramount in innate immunity. Human STING is encoded by the gene TMEM173. Activation of STING leads to production of Type I interferons (e.g. IFN-α and IFN-β), via the IRF3 (interferon regulatory factor 3) pathway; and to production of pro-inflammatory cytokines (IL-1α, IL-1β, IL-2, IL-6, TNF-α, etc.), via the oncogenic transcription factor NF-κB (nuclear factor kappa-light-chain-enhancer of activated B cells) pathway. Moreover, researchers recently reported that in response to viral infection, STING activates STAT6 (signal transducer and activator of transcription 6) to induce (Th2-type), increase (IL-12) or decrease (IL-10) production of various cytokines, including the chemokines CCL2, CCL20, and CCL26 (Chen et al., 2011)

STING Agonists

Human STING is currently known to be activated three ways: via binding of exogenous (3',3) cyclic dinucleotides (c-diGMP, c-diAMP and c-GAMP) that are released by invading bacteria or archaea (see (Gomelsky, 2011) and references therein); via binding of (2',3')cyclic guanosine monophosphate-adenosine monophosphate ((2',3')c-GAMP), a recently discovered endogenous cyclic dinucleotide that is produced by the enzyme cyclic GMP-AMP synthase (cGAS; also known as C6orf150 or MB21D1) in the presence of exogenous double-stranded DNA (e.g. that released by invading bacteria, viruses or protozoa) or of self-DNA in mammals (see, for example: (Ablasser et al., 2013) and (Zhang et al., 2013)); or via binding of synthetic ligands, such as analogs of the aforementioned naturally-occurring cyclic dinucleotides (see, for example: (Dubensky, Kanne, & Leong, 2013) and (Li et al., 2014)).

Modulation of STING in Immunotherapy

Inspired by the interplay among STING, cytokines and immune response, as well as by the ever-growing body of knowledge on the clinical implications of STING and its mutations, researchers have very recently begun to explore STING as a therapeutic target for myriad indications. New STING agonists are being pursued as therapeutic agents for human and animal health in areas such as cancer or infectious diseases. The known cyclic dinucleotide STING agonists are an excellent class of compounds on which to base analogs that might exhibit interesting biological activities or desirable drug-like properties. The present invention comprises novel cyclic dinucleotides for therapeutic use in human and animal health.

DETAILED DESCRIPTION OF THE INVENTION

CDN STING Agonists

Some examples of cyclic dinucleotide (CDN) STING agonists are described in US/2014/0329889 and WO/2014/189805. However, the authors only chemically synthesized and biologically tested a very small number of the compounds that would be theoretically possible from the extremely general chemical structure drawings that they provide. They do not disclose any detailed structure-activity relationships or describe any class effects of particular structural classes of CDNs. Consequently, the authors provide scant rationale to corroborate the choice of one structural class of CDNs over another in terms of actual STING activity or other properties (e.g. drug-like properties) for a desired STING-related application. More recently, WO/2015/077354 (PCT/US2014/066436) explored STING agonists, including CDNs, all of which are (2',3')-CDNs in which both nucleotides contain a ribose sugar moiety and the two nucleotides are connected by phosphorothioate diester linkages.

Knowledge Gaps on CDN STING Agonists

Very little is known about the biological activity of different structural classes of CDNs. Specifically, there is scant patent precedent on class effects according to CDN structural class, nor is there any patent precedent on how such class effects might be specifically exploited for specific therapeutic, diagnostic or research applications related to STING activity. Such information will be critical for discovery and exploitation of novel CDN STING agonists with desirable properties for therapeutic, diagnostic or research applications based on manipulation of STING activity.

The Present Invention

Considering the paucity of reported structure-activity relationships for STING agonists, the field of STING agonists is ripe for invention. In this context, the present invention concerns fluorinated deoxyribo-CDN STING agonists that exhibit unique, unobvious and previously unreported class effects relative to their corresponding non-fluorinated analogs.

In our work exploring cyclic dinucleotides (CDNs) as immunomodulatory compounds and potential agonists of STING, we initially sought to synthesize and assay CDNs of the following Formulas (I), (II) and (III):

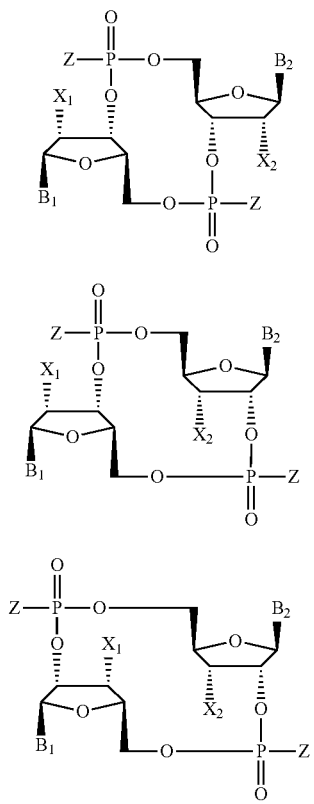

Formula (I)

Formula (II)

Formula (III)

wherein:

X$_1$ is H, OH, or F;

X$_2$ is H, OH, or F;

Z is OH, OR$_1$, SH or SR$_1$, wherein:

i) R$_1$ is Na or NH$_4$, or ii) R$_1$ is an enzyme-labile group which provides OH or SH in vivo such as pivaloyloxymethyl;

B$_1$ and B$_2$ are bases chosen from:

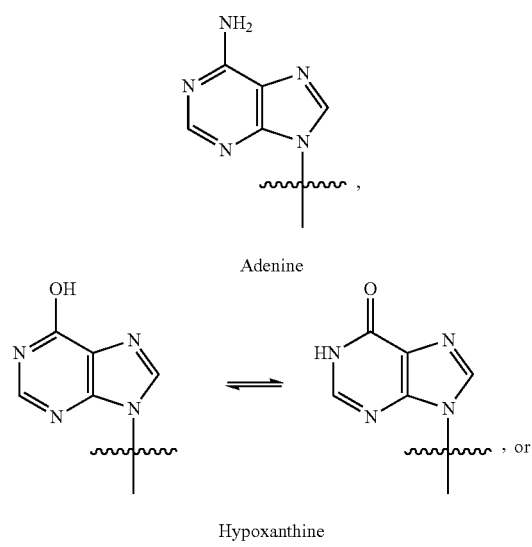

Adenine

Hypoxanthine

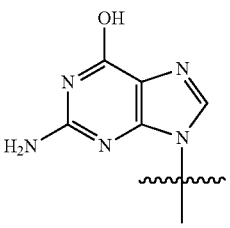

Guanine with the proviso that:

in Formula (I): X$_1$ and X$_2$ are not OH, in Formula (II): when X$_1$ and X$_2$ are OH, B$_1$ is not Adenine and B$_2$ is not Guanine, and in Formula (III): when X$_1$ and X$_2$ are OH, B$_1$ is not Adenine, B$_2$ is not Guanine and Z is not OH.

In the present invention, the term "cyclic dinucleotide" (abbreviated as "CDN") represent a class of cyclic molecules with two phosphodiester linkages, or two phosphorothioate diester linkages, or one phosphodiester linkage and one phosphorothioate diester linkage, between two nucleosides. This includes (3',5')-(3',5') nucleotide linkages (abbreviated as (3',3')); (3',5')-(2',5') nucleotide linkages (abbreviated as (3',2')); (2',5')-(3',5') nucleotide linkages (abbreviated as (2',3')); and (2',5')-(2',5') nucleotide linkages (abbreviated as (2',2')).

The term "nucleoside" refers to a glycosylamine comprising a nitrogenous base and a five-carbon sugar, wherein the nitrogenous base is bound to the five-carbon sugar via a beta-glycosidic linkage.

The term "nucleotide" refers to any nucleoside linked to a phosphate group at position 5', 3' or 2' of the sugar moiety.

"Pharmaceutically acceptable salts" include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art.

The term "pharmaceutically acceptable prodrug" herein refers to a compound that is metabolized, for example hydrolyzed or oxidized, in the host (i.e. the human or animal subject that receives the compound) to form the compound of the present invention. Typical examples of prodrugs include compounds that have biologically labile protecting groups on functional moieties of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated or dephosphorylated to produce the active compound.

The term "prodrug", as used herein, relates to an inactive or active derivative of a compound represented by the structural Formula (I), (II) or (III) as defined herein above or any one of their specific embodiments, which undergoes spontaneous or enzymatic transformation within the body of an animal, e.g. a mammal such as a human being, in order to release the pharmacologically active form of the compound. For a comprehensive review, see (Rautio et al., 2008).

In particular for the purpose of the present invention, prodrugs of the compounds represented by the structural Formula (I), (II) or (III) including any one of the above-described specific embodiments thereof, may be formed as described in detail in (Hecker & Erion, 2008).

Phosphate prodrug can take the form of an ester, in particular acyloxyalkyl esters (e.g. pivaloyloxymethyl ester (POM)) or S-acylthioethyl (SATE) esters, a carbonate, a carbamate or an amide, such as amino acid prodrugs.

The expression "enzyme-labile protecting group" denotes a group designed to enable passive diffusion of a compound across cellular or parasitic membranes via charge-masking, such that, once inside the cell or parasite interior, the compound undergoes an enzymatic transformation (or deprotection) that affords an OH or SH group. Examples of enzyme-labile protecting groups include for instance acyloxyalkyl groups such as pivaloyloxymethyl (POM) or S-acylthioethyl (SATE) or amino acid groups.

In the present description, it is considered that the expression "cyclic dinucleotides of Formula (I), (II) or (III)" is considered to also include the pharmaceutically acceptable salts or a pharmaceutically acceptable prodrugs of said cyclic dinucleotides of Formula (I), (II) or (III).

A particular class of cyclic dinucleotides of Formula (I), (II) or (III) is when $B_1$ or $B_2$ is Guanine.

A particular class of cyclic dinucleotides of Formula (I), (II) or (III) is when $B_1$ or $B_2$ is Adenine.

A particular class of cyclic dinucleotides of Formula (I), (II) or (III) is when $B_1$ or $B_2$ are Hypoxanthine.

A particular class of cyclic dinucleotides of Formula (I), (II) or (III) is when $B_1$ and $B_2$ are independently chosen from Guanine or Adenine.

A particular class of cyclic dinucleotides of Formula (I), (II) or (III) is when $B_1$ or $B_2$ are independently chosen from Guanine or Hypoxanthine.

A particular class of cyclic dinucleotides of Formula (I), (II) or (III) is when $B_1$ and $B_2$ are independently chosen from Adenine or Hypoxanthine.

A particular class of cyclic dinucleotides of Formula (I), (II) or (III) is when Z is OH.

A particular class of cyclic dinucleotides of Formula (I), (II) or (III) is when Z is SH.

A particular class of cyclic dinucleotides of Formula (I), (II) or (III) is when Z is OH or SH.

A particular class of cyclic dinucleotides of Formula (I), (II) or (III) is when Z is $SR_1$, wherein:
 i) $R_1$ is Na or $NH_4$, or
 ii) $R_1$ is an enzyme-labile group which provides OH or SH in vivo such as pivaloyloxymethyl.

A particular class of cyclic dinucleotides of Formula (I), (II) or (III) is when $B_1$ and $B_2$ are independently chosen from Adenine or Hypoxanthine and $X_1$ and $X_2$ are identical. Preferably, $X_1$ and $X_2$ are OH or a fluorine atom. In one particular embodiment, Z is OH or SH.

A particular class of cyclic dinucleotides of Formula (I), (II) or (III) is when $B_1$ and $B_2$ are independently chosen from Guanine or Hypoxanthine and $X_1$ and $X_2$ are identical. Preferably, $X_1$ and $X_2$ are OH or a fluorine atom. In one particular embodiment, Z is OH or SH.

A particular class of cyclic dinucleotides of Formula (I), (II) or (III) is when $B_1$ and $B_2$ are independently chosen from Adenine or Guanine and $X_1$ and $X_2$ are identical. Preferably, $X_1$ and $X_2$ are OH or a fluorine atom. In one particular embodiment, Z is OH or SH.

A particular class of cyclic dinucleotides of Formula (I), (II) or (III) is when $X_1$ and $X_2$ are not a fluorine atom.

A particular class of cyclic dinucleotides of Formula (I), (II) or (III) is when at least one among $X_1$ and $X_2$ is a fluorine atom. In one particular embodiment, $X_1$ and $X_2$ are both a fluorine atom.

A particular class of cyclic dinucleotides of Formula (I), (II) or (III) is the following cyclic dinucleotides (each of which is provided with a five-character code of the format "CL###"):

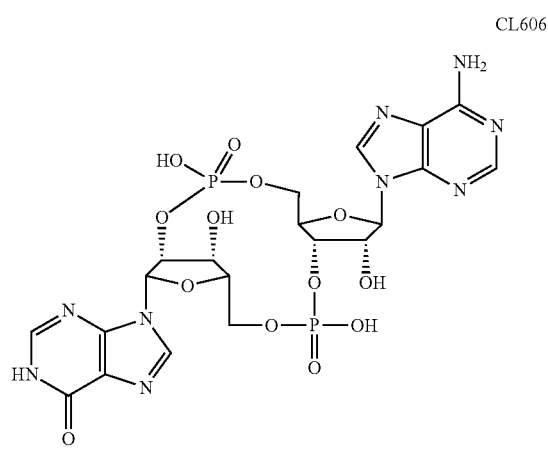

(3',2')c-AIMP

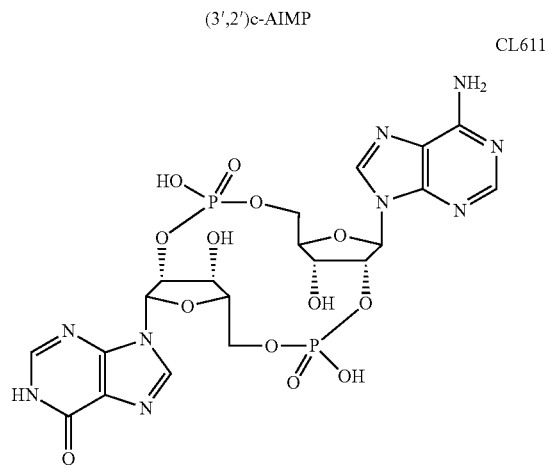

(2',2')c-AIMP

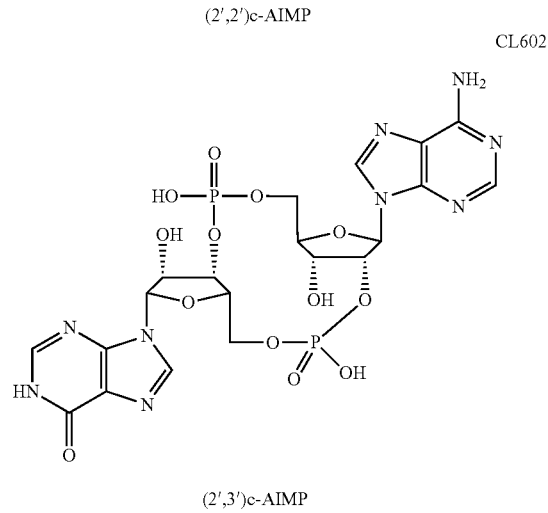

(2',3')c-AIMP

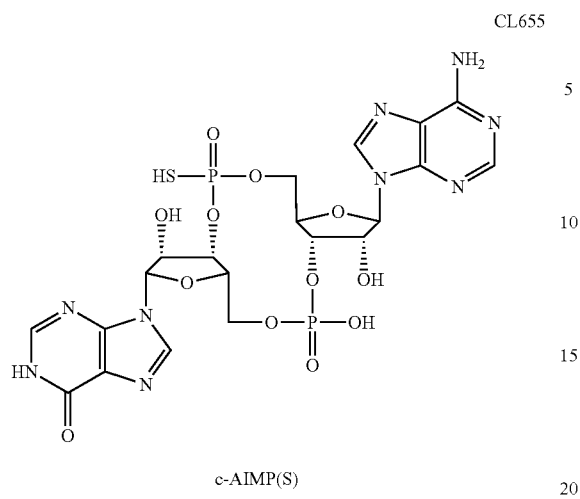
c-AIMP(S)
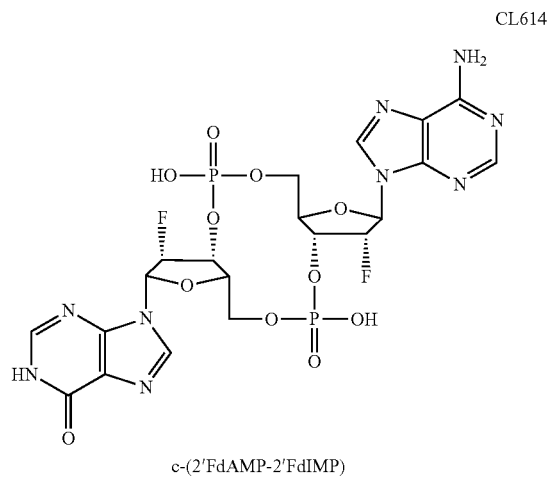
c-(2'FdAMP-2'FdIMP)
or a pharmaceutically acceptable salt or prodrug thereof.
A particular class of cyclic dinucleotides of Formula (I), (II) or (III) is when one or both nucleosides are modified at the 2' position. This class comprises the following compounds:
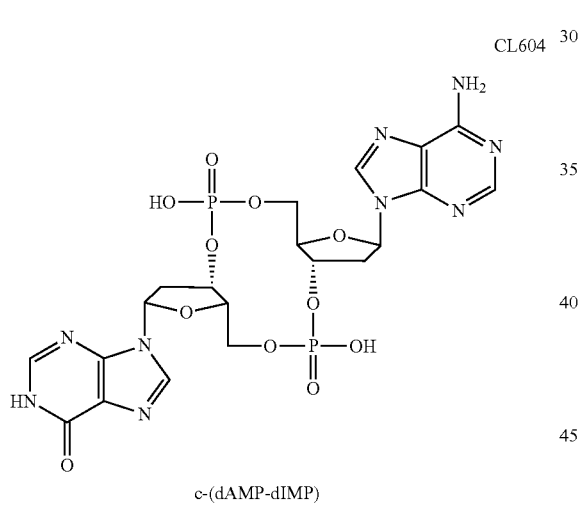
c-(dAMP-dIMP)
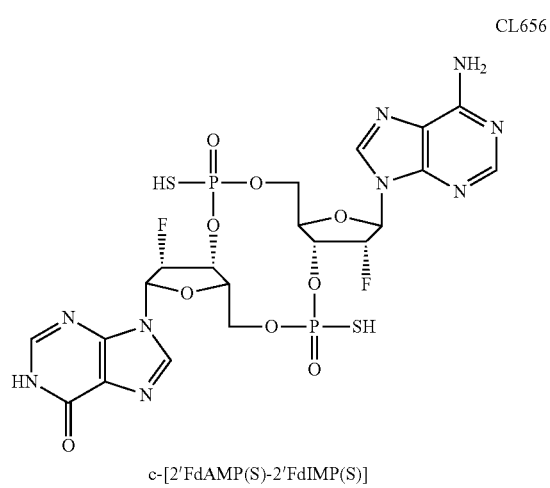
c-[2'FdAMP(S)-2'FdIMP(S)]
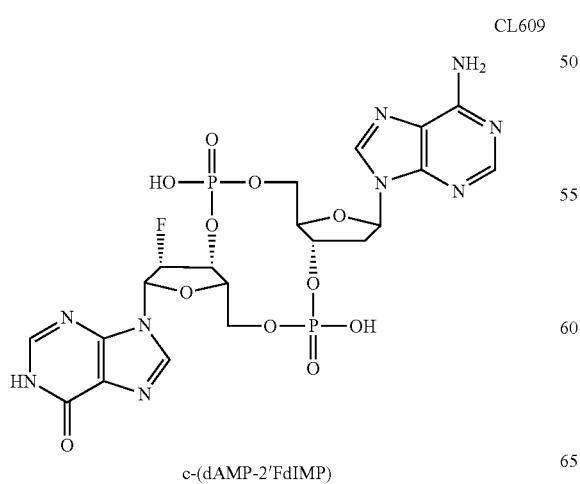
c-(dAMP-2'FdIMP)
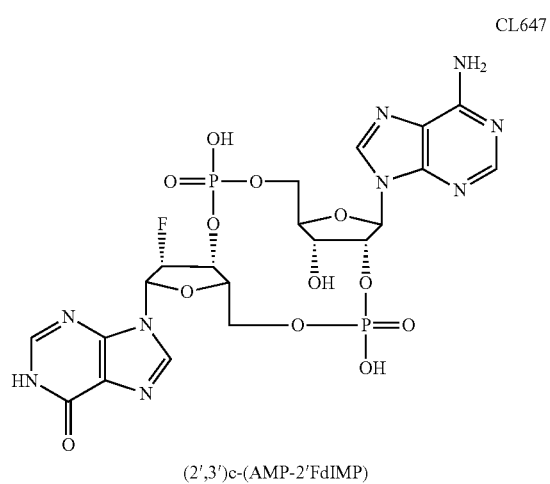
(2',3')c-(AMP-2'FdIMP)

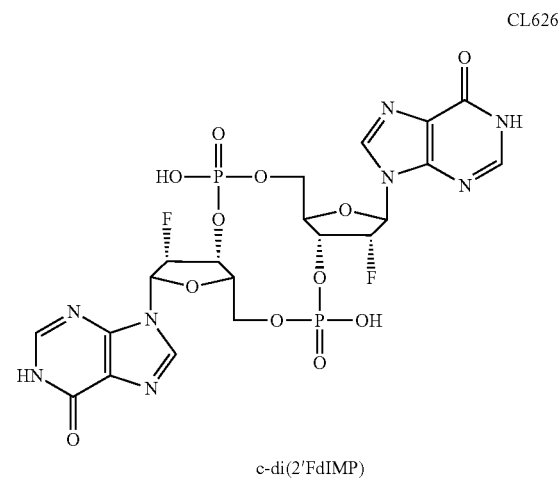

c-di(2'FdIMP)

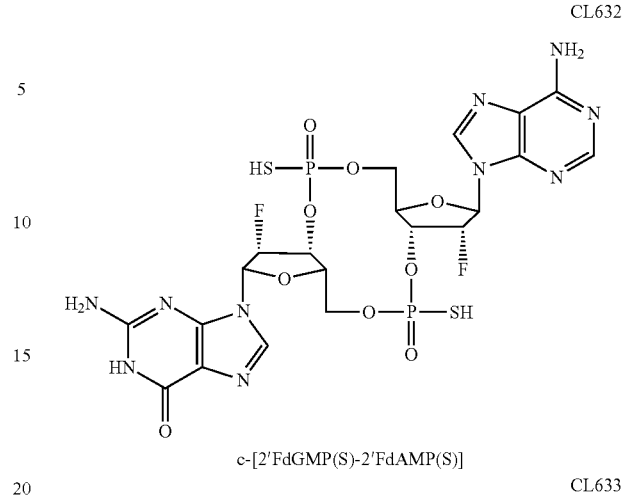

c-[2'FdGMP(S)-2'FdAMP(S)]

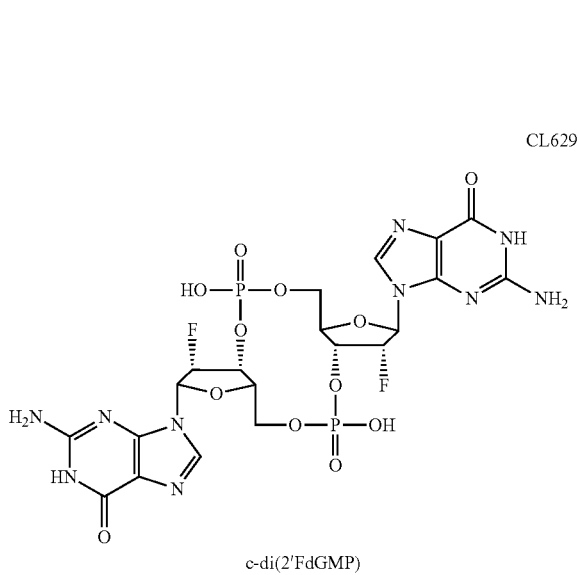

c-di(2'FdGMP)

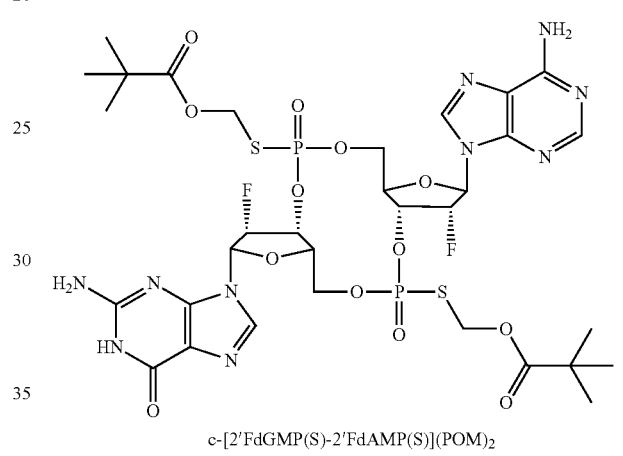

c-[2'FdGMP(S)-2'FdAMP(S)](POM)$_2$

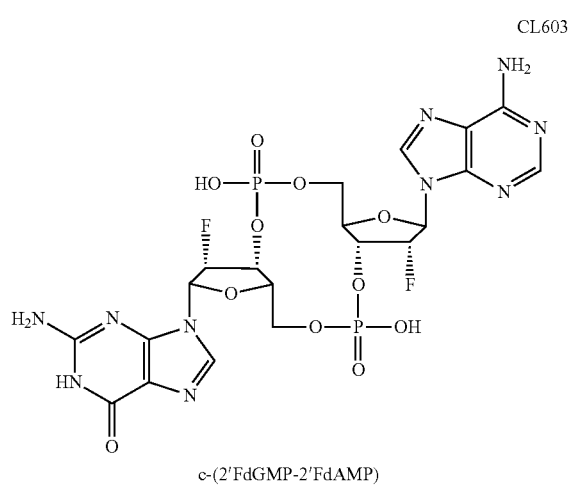

c-(2'FdGMP-2'FdAMP)

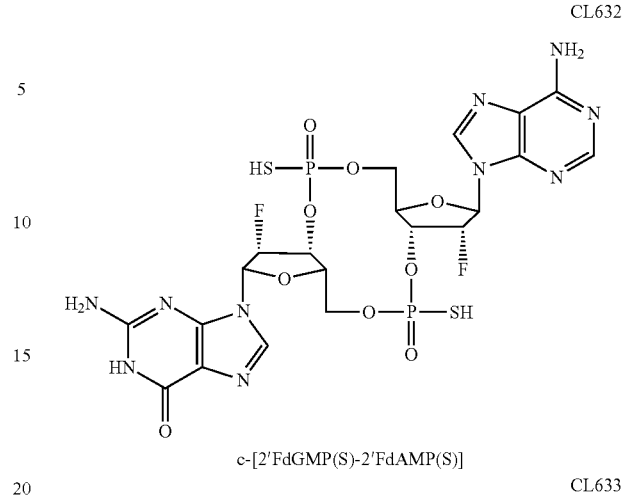

c-[2'FdAMP(S)-2'FdIMP(S)](POM)$_2$

We identified a structurally unprecedented subset of these CDNs that showed surprising biological activity and that have never previously been reported as STING agonists. These CDNs form the basis for the present invention and are distinct from previously reported CDN STING agonists (see, for example: US/2014/0329889 and WO/2014/189805). Thus, in one aspect, the present invention provides CDNs that are defined by all of the following structural criteria: firstly, unlike in naturally occurring CDNs, in which the sugar moiety of each nucleotide is a ribose, in the CDNs of the present invention the sugar moiety of each nucleotide is a 2'-deoxyribose; secondly, in the CDNs of the present invention, either the 2' position of the sugar moiety in both nucleotides must be substituted with a fluorine atom, or the 2' position of the sugar moiety of one nucleotide must be substituted with a fluorine atom while the 2' position of the sugar moiety of the other nucleotide must be substituted with a hydrogen atom; thirdly, in the CDNs of the present invention, the base in each nucleotide is preferably chosen from guanine, adenine or hypoxanthine, with the proviso that the two nucleotides of the CDN cannot contain the same base.

Thus, in one embodiment, the present invention provides CDNs of Formula (I) according to claim 1, i.e. compounds of Formula (I):

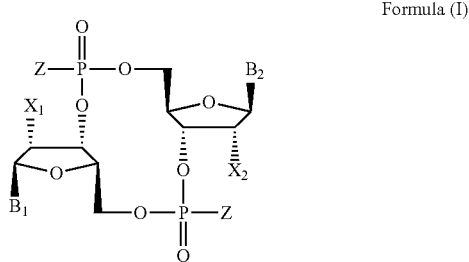

Formula (I)

wherein:
$X_1$ is H or F;
$X_2$ is H or F;
At least one among $X_1$ and $X_2$ is a fluorine atom;
Z is OH, $OR_1$, SH or $SR_1$, wherein:
  i) $R_1$ is Na or $NH_4$, or
  ii) $R_1$ is an enzyme-labile group which provides OH or SH in vivo such as pivaloyloxymethyl;
$B_1$ and $B_2$ are bases chosen from:

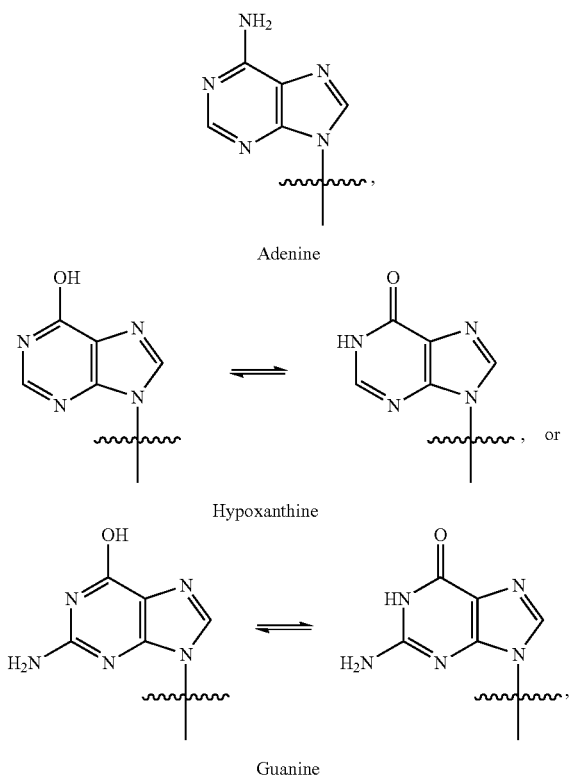

and $B_1$ is a different base than $B_2$,
or a pharmaceutically acceptable salt thereof.
The expression "$B_1$ is a different base than $B_2$" includes $B_1$ is Guanine and $B_2$ is Adenine or $B_1$ is Guanine and $B_2$ is Hypoxanthine or $B_1$ is Adenine and $B_2$ is Guanine or $B_1$ is Adenine and $B_2$ is Hypoxanthine or $B_1$ is Hypoxanthine and $B_2$ is Guanine or $B_1$ is Hypoxanthine and $B_2$ is Adenine.

A particular class of cyclic dinucleotides of Formula (I) as defined above is when $B_1$ and $B_2$ are different and both $X_1$ and $X_2$ are F.

A particular class of cyclic dinucleotides of Formula (I) as defined above is when $B_1$ and $B_2$ are different, both $X_1$ and $X_2$ are F and Z is OH.

A particular class of cyclic dinucleotides of Formula (I) as defined above is when $B_1$ and $B_2$ are different, both $X_1$ and $X_2$ are F and Z is $OR_1$ as defined above.

A particular class of cyclic dinucleotides of Formula (I) as defined above is when $B_1$ and $B_2$ are different, both $X_1$ and $X_2$ are F and Z is SH as defined above.

A particular class of cyclic dinucleotides of Formula (I) as defined above is when $B_1$ and $B_2$ are different, both $X_1$ and $X_2$ are F and Z is $SR_1$ as defined above.

A particular class of cyclic dinucleotides of Formula (I) as defined above is when $B_1$ and $B_2$ are different and $X_1$ and $X_2$ are different (i.e. $X_1$=H and $X_2$=F or $X_1$=F and $X_1$=H).

A particular class of cyclic dinucleotides of Formula (I) as defined above is when $B_1$ and $B_2$ are different, $X_1$ and $X_2$ are different and Z is OH.

A particular class of cyclic dinucleotides of Formula (I) as defined above is when $B_1$ and $B_2$ are different, $X_1$ and $X_2$ are different and Z is $OR_1$ as defined above.

A particular class of cyclic dinucleotides of Formula (I) as defined above is when $B_1$ and $B_2$ are different, $X_1$ and $X_2$ are different and Z is SH as defined above.

A particular class of cyclic dinucleotides of Formula (I) as defined above is when $B_1$ and $B_2$ are different, $X_1$ and $X_2$ are different and Z is $SR_1$ as defined above.

The cyclic dinucleotides of the present invention induce Type I interferons and/or pro-inflammatory cytokines in vitro in human cells, animal cells and human blood. The cytokine-induction activity of these cyclic dinucleotides requires the presence of STING, as confirmed by in vitro experiments in human or animal cells.

The cyclic dinucleotides of the invention are agonists of the receptor STING.

The term "agonist" refers to any substance that activates a biologic receptor in vitro or in vivo to provoke a physiologic response.

"STING" is an abbreviation of "stimulator of interferon genes", which is also known as "endoplasmic reticulum interferon stimulator (ERIS)", "mediator of IRF3 activation (MITA)", "MPYS" or "transmembrane protein 173 (TM173)". STING is a transmembrane receptor protein that in humans is encoded by the gene TMEM173. Activation of STING by cyclic dinucleotides (CDN) leads to activation of the IRF3 and NF-κB pathways and consequently, to induction of Type I interferons and of pro-inflammatory cytokines, respectively. In response to viral infection, STING activates STAT6 (signal transducer and activator of transcription 6) to induce (Th2-type), increase (IL-12) or decrease (IL-10) production of various cytokines, including the chemokines CCL2, CCL20, and CCL26 (Chen et al., 2011).

The term "STING agonist" herein refers to a substance that activates the receptor STING in vitro or in vivo. According to the invention, a compound is deemed to be a STING agonist if:
  it induces Type I interferons in vitro in human or animal cells that contain active STING; and
  it does not induce Type I interferons in vitro in human or animal cells that do not contain active STING.

A typical test to ascertain whether a ligand is a STING agonist is to incubate the ligand in a wild-type human or animal cell line and in the corresponding cell line in which the STING coding gene has been genetically inactivated by small or long base deletions (e.g. a homozygous STING knockout cell line). An agonist of STING will induce Type I interferons in the wild-type cells but will not induce Type I interferons in the cells in which the STING coding gene has been inactivated.

The cyclic dinucleotides of the invention induce Type I interferons in vitro in human or animal cells that contain active STING. However, they do not induce Type I interferons in vitro in human or animal cells that do not contain active STING.

The present invention is concerned with fluorinated deoxyribo-cyclic dinucleotides (CDNs). Specifically, it is concerned with (3',3')-2'(mono- or di-fluorinated)-2'-deoxyribo-(CDNs).

The cyclic dinucleotides of Formula (I), (II) or (III) wherein at least one among $X_1$ and $X_2$ is a fluorine atom, in particular $X_1$ and $X_2$ are both a fluorine atom, and Z is OH induce more Type I interferon and NF-κB activity than do their non-fluorinated counterparts in human and murine cell lines.

The cyclic dinucleotides of Formula (I), (II) and (III) wherein at least one among $X_1$ and $X_2$ is a fluorine, in particular $X_1$ and $X_2$ are both a fluorine atom, and Z is OH or SH exhibit slower elimination from blood after intravenous injection in mice, i.e. longer kinetics of clearance, and exhibit greater resistance to enzymatic cleavage in vitro; as compared to their corresponding non-fluorinated CDNs.

Salts or Prodrug Formulations of the Cyclic Dinucleotides

Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. The term "pharmaceutically acceptable prodrugs" refers to a compound that is metabolized, for example hydrolyzed or oxidized, in the host (i.e. the human or animal subject that receives the compound) to form the compound of the present invention. Typical examples of prodrugs include compounds that have biologically labile protecting groups on functional moieties of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated or dephosphorylated to produce the active compound.

The CDN prodrugs described herein can be administered to additionally increase the activity, bioavailability or stability, or otherwise alter the properties of the CDN monophosphate.

A number of CDN prodrug ligands are known. In general, alkylation, acylation or other lipophilic modifications on the phosphate moiety, or the use of other analog of the nucleoside, will increase the stability of the nucleotide.

Examples of substituent groups that can replace one or more hydrogens on the phosphate moiety are alkyl, aryl, steroids, carbohydrates, including, but not limited to, sugars, 1,2-diacylglycerol and alcohols. Many are described in (Jones, 1995).

Use of the Compounds of the Invention

Another object of the present invention is the cyclic dinucleotides of Formula (I), (II) or (III) for use in a therapeutic treatment in humans or animals.

In particular, the compounds of the present invention may be used for therapeutic or diagnostic applications in human or animal health. The following examples serve to illustrate different possible applications of the present invention; however, these examples are not intended to limit the scope of the invention.

The term "therapeutic agent" refers to one or more substances that are administered to a human or animal in order to achieve some kind of therapeutic effect in that human or animal, including to prevent, cure, or mitigate the effects of, infection or disease, and/or to otherwise improve the health of that human or animal.

The term "monotherapy" refers to the use of a single substance and/or strategy to treat a human or animal in any clinical or medical context, as opposed to the use of multiple substances and/or strategies to treat a human or animal in the same clinical or medical context, regardless of whether the multiple substances and/or strategies are used sequentially in any order or concurrently.

The term "chemotherapeutic agent" herein refers to one or more chemical substances that are administered to a human or animal in order to kill tumors, or slow or stop the growth of tumors, and/or slow or stop the division of cancerous cells and/or prevent or slow metastasis. Chemotherapeutic agents are often administered to treat cancer, but are also indicated for other diseases.

The term "chemotherapy" refers to medical treatment of a human or animal with one or more chemotherapeutic agents (see definition above).

The term "chemoimmunotherapy" refers to the combined use, whether sequentially in any order or concurrently, of chemotherapy substances and/or strategies, and immunotherapy substances and/or strategies. Chemoimmunotherapy is often employed to treat cancer, but can also be employed to treat other diseases.

The term "immune system" refers to the ensemble, or to any one or more components, of the molecules, substances (e.g. bodily fluids), anatomic structures (e.g. cells, tissue and organs) and physiologic processes involved in preventing infection in the body, in protecting the body during infection or during disease, and/or in helping the body to recuperate after infection or disease. A complete definition of "immune system" is beyond the scope of this patent; however, this term should be understood by any ordinary practitioner in the field.

The term "immune agent" refers to any endogenous or exogenous substance that can interact with any one or more components of the immune system. The term "immune agent" includes antibodies, antigens, vaccines and their constituent components, nucleic acids, synthetic drugs, natural or synthetic organic compounds, cytokines, natural or modified cells, synthetic analogs thereof, and/or fragments thereof.

The term "immunotherapy" refers to any medical treatment in which one or more components of a human's or animal's immune system is deliberately modulated in order to directly or indirectly achieve some therapeutic benefit, including systemic and/or local effects, and preventative and/or curative effects. Immunotherapy can involve administering one or more immune agents (see definition above), either alone or in any combination, to a human or animal subject by any route (e.g. orally, intravenously, dermally, by injection, by inhalation, etc.), whether systemically, locally or both. "Immunotherapy" can involve provoking, increasing, decreasing, halting, preventing, blocking or otherwise modulating the production of cytokines, and/or activating or deactivating cytokines or immune cells, and/or modulating the levels of immune cells, and/or delivering one or more therapeutic or diagnostic substances to a particular location in the body or to a particular type of cell or tissue, and/or destroying particular cells or tissue. Immunotherapy can be used to achieve local effects, systemic effects or a combination of both.

The term "immunosuppressed" describes the state of any human or animal subject whose immune system is functionally diminished, deactivated or otherwise compromised, or in whom one or more immune components is functionally diminished, deactivated or otherwise compromised. "Immunosuppression" can be the cause, consequence or byproduct of disease, infection, exhaustion, malnutrition, medical treatment or some other physiologic or clinical state.

The terms "immunomodulating substance", "immunomodulatory substance", "immunomodulatory agent" and "immunomodulator", used here synonymously, refer to any substance that, upon administration to a human or animal, directly influences the functioning of the immune system of that human or animal. Examples of common immunomodulators include, but are not limited to, antigens, antibodies and small-molecule drugs.

The term "vaccine" refers to a biological preparation administered to a human or animal in order to elicit or enhance a specific immune system response and/or protection against one or more antigens in that human or animal.

The term "vaccination" refers to treatment of a human or animal with a vaccine or to the act of administering a vaccine to a human or animal.

The term "adjuvant" refers to a secondary therapeutic substance that is administered together (either sequentially in any order, or concurrently) with a primary therapeutic substance to achieve some kind of complimentary, synergic or otherwise beneficial effect that could not be achieved through use of the primary therapeutic substance alone. An adjuvant can be used together with a vaccine, chemotherapy, or some other therapeutic substance. Adjuvants can enhance the efficacy of the primary therapeutic substance, reduce the toxicity or side effects of the primary therapeutic substance, or provide some kind of protection to the subject that receives the primary therapeutic substance, such as, but not limited to, improved functioning of the immune system.

In one embodiment, the cyclic dinucleotide of Formula (I), (II) or (III) can be administered as immunotherapy to a human or an animal to induce in vivo production of one or more cytokines that are therapeutically beneficial to that human or animal. This type of immunotherapy could be used alone or in combination with other treatment strategies, whether sequentially in any order, or concurrently. It could be used to prevent, cure, and/or mitigate the effects of, infection or disease in that human or animal, and/or to modulate the immune system of that human or animal to achieve some other therapeutic benefit.

In one particular embodiment, the cyclic dinucleotides of the present invention can be used for cytokine induction immunotherapy of immunosuppressed individuals.

In this example, a cyclic dinucleotide of Formula (I) (II) or (III) would be administered to an immunosuppressed human or animal subject to induce in vivo production of one or more cytokines that directly or indirectly enhance the immune system of that human or animal. Subjects that might benefit from such treatment include those suffering from autoimmune disorders, immune system deficiencies or defects, microbial or viral infections, infectious diseases, or cancer.

The present invention thus discloses a method for inducing cytokine in immunosuppressed individuals, said method comprising administering to a patient in need thereof a cyclic dinucleotide of Formula (I), (II) or (III) or a pharmaceutically acceptable salt or prodrug thereof.

In another embodiment, the cyclic dinucleotides of the present invention can be used for cytokine induction immunotherapy in combination with chemotherapy In this example, a cyclic dinucleotide of Formula (I) (II) or (III) would be administered together with one or more chemotherapeutic agents, sequentially in any order or concomitantly, to a cancer patient to stop the growth of, shrink and/or destroy tumors in that patient. The chemoimmunotherapy resulting from the combination of cytokine induction, provided by the compound(s) of the present invention, and cytotoxicity, provided by the chemotherapeutic agent(s), might be less toxic to the patient, cause fewer side effects in the patient and/or exhibit greater anti-tumor efficacy than would the chemotherapeutic agent(s) when used as monotherapy.

The present invention thus discloses a method for treating cancer, said method comprising administering to a patient in need thereof:
  a chemotherapeutic agent; and
  a cyclic dinucleotide of Formula (I), (II) or (III) or a pharmaceutically acceptable salt or prodrug thereof.

In another embodiment, the cyclic dinucleotides of the present invention can be used for cytokine induction immunotherapy as vaccine adjuvant therapy.

In this example, a cyclic dinucleotide of Formula (I) (II) or (III) would be administered to a human or animal subject that has received, is receiving or will receive a vaccination. The benefits provided by the present invention might include enhanced efficacy of the vaccination against the target antigen, reduced toxicity of the vaccination, reduced adverse side effects of the vaccination, or enhanced immune protection of the human or animal subject.

Another object of the present invention is the cyclic dinucleotides of Formula (I), (II) or (III) for use in the treatment of a bacterial infection, a viral infection or a cancer.

As used herein, "cancer" refers to the physiological condition in subjects that is characterized by unregulated or dysregulated cell growth or death. The term "cancer" includes solid tumors and blood-born tumors, whether malignant or benign.

In a preferred embodiment, the cancer is from the following group: bladder cancer, breast cancer, cholangiocellular cancer, leukemia, lung cancer, lymphoma, nasopharyngeal cancer, ovarian cancer, pancreatic cancer and urothelial cancer.

In one particular embodiment, the cancer is a solid pancreatic tumor.

The present invention thus discloses a method for treating a bacterial infection, a viral infection or a cancer, said method comprising administering to a patient in need thereof a cyclic dinucleotide of Formula (I), (III) or (III) or a pharmaceutically acceptable salt or prodrug thereof.

Another object of the present invention is the cyclic dinucleotides of Formula (I), (II) or (III) for use in the treatment of a pathology that may be alleviated by the induction of an immune response via the STING pathway.

Another object of the present invention is a kit-of-parts comprising a cyclic dinucleotide of Formula (I), (II) or (III) and a chemotherapeutic agent for use in the treatment of solid pancreatic tumors.

The term "kit-of-parts" herein refers to a combined preparation wherein the active ingredients are physically separated for use in a combined therapy by simultaneous administration or sequential administration to the patient.

Hence, according to the present invention, the chemotherapeutic agent and the cyclic dinucleotide or a pharmaceutically acceptable salt or prodrug thereof are administered to the patient in a separate form, either simultaneously, separately or sequentially in any order, for the treatment of cancer.

In one embodiment, said chemotherapeutic agent is gemcitabine.

Deoxynucleosides for the Synthesis of Cyclic Dinucleotides

Natural nucleosides, 2'-deoxy-Adenosine (dA), 2'-deoxy-Guanosine (dG), or 2'-deoxy-Inosine (dI) can be used for the synthesis of CDNs of the Formulas (I) and (II).

The 3'-deoxy-Adenine, 3'-deoxy-Guanosine, or 3'-deoxy-Inosine for CDNs of the Formula (II) and (III) refers to a nucleoside unit having a sugar moiety, for example a ribosyl moiety or a xylosyl moiety that is modified at the 3' position such that the hydroxyl group (3'-OH) is replaced by an hydrogen group.

Fluoro-Substituted Nucleosides for the Synthesis of CDNs

Since STING is located in the endoplasmic reticulum and detects cyclic dinucleotides in the cytoplasm, any STING agonist destined for therapeutic use must be able to penetrate into cells. Furthermore, greater cellular uptake of a compound translates to higher bioavailability, which is a desirable property for clinical use. In the present invention, the fluorinated compounds were designed to explore the possibility that greater cellular uptake conferred by one or two fluorine atoms would lead to greater Type I interferon induction activity than that of the reference compound, c-AIMP, which does not contain any fluorine atoms.

In the present invention, we surprisingly found that the subject CDNs, all of which contain at least one fluorine atom, are more active as STING agonists than are their corresponding non-fluorinated analogs. Specifically, the CDNs of the present invention exhibit greater STING-dependent cytokine induction activity in human cells, animal cells and human blood than do their corresponding non-fluorinated analogs The more quickly a drug is enzymatically degraded in the body, the shorter will be its half-life and consequently, the lesser will be its activity. Thus, a desirable property for compounds intended for therapeutic use is resistance to enzymatic degradation. There are in vitro enzymatic cleavage tests that can provide some indication of the resistance of a given compound to common enzymes that degrade compounds that are structurally similar to the one being tested. In our work, we were very surprised to discover yet another distinguishing characteristic of the subject CDNs of the present invention: these fluorinated deoxyribo-CDNs consistently showed superior resistance to cleavage by snake-venom phosphodiesterase (SVPD) or nuclease P1 (NP1), compared to their corresponding non-fluorinated ribo-CDNs.

Monofluoro-Nucleoside

The 2'-deoxy-2'-fluoro of Adenosine, Guanosine or Inosine for CDNs of Formula (I) and (II) refers to a nucleoside with a modification at the 2' position, such that, the hydroxyl group (2'-OH) is replaced by a fluoro group (2'-F).

The 2'-fluoronucleoside derivatives for the synthesis of CDNs of Formula (I) and (II) may be prepared by any of the methods known in the art (see, for example: (Herdewijna, 1989; Thomas, 1994) and (Ross, 1997)).

The 3'-deoxy-3'-fluoro of Adenosine, Guanosine or Inosine for CDN of Formula (II) and (III) refers to a nucleoside with a modification at the 3' position, such that the hydroxyl group (3'-OH) is replaced by a fluoro group (3'-F).

Phosphorothioate Internucleotide Linkage

The phosphorothioate internucleotide linkage refers to the replacement of a P=O group with a P=S group, and includes phosphorodithioate internucleoside linkages. One or both of the internucleotide linkages that are present in the cyclic dinucleotides can be phosphorothioate internucleotide linkages.

The phosphorous atom in a phosphodiester linkage of CDNs can be described as being "pro-chiral." Once a non-bonding oxygen atom of the phosphodiester linkage is replaced or modified, a chiral sugar-phosphate linkage is generated. The resulting intersugar linkage is either an Sp intersugar linkage or an Rp intersugar linkage. Replacement of a non-bonding oxygen atom in the natural phosphodiester linkage, with a sulfur atom to obtain a phosphorothioate linkage generates a chiral center and consequently, affords Sp and Rp diastereomers. Molecules wherein substantially all of the phosphorous atoms in the sugar backbone are either Sp or Rp are referred to herein as "chirally pure".

Cyclic dinucleotides are enzymatically degraded by nucleases and/or phosphodiesterases (see, for example: (Li et al., 2014) (Diner et al., 2013) (Danilchanka & Mekalanos, 2013) (Shanahan, Gaffney, Jones, & Strobel, 2013) (Simm, Morr, Kader, Nimtz, & Romling, 2004)) and therefore, when used as therapeutic agents, these compounds can suffer from diminished half-life. The compounds CL655 and CL656 were chosen to enable maximal half-life, and possibly higher activity, in vivo, as they contain phosphorothioate (also known as "P(S)" or "thiophosphate") internucleotide linkages. The use of such linkages is a known strategy to circumvent enzymatic hydrolysis (see, for example: US 2014/0205653 A1). An example of a phosphorothioate compound that is more resistant to enzymatic hydrolysis than its phosphodiester analog is (2',3')c-$G^sA^sMP$ or (2',3') c-GAMP(S) (InvivoGen catalog code: tlrl-scga; Li, 2014). The phosphorothioate linkage introduces an additional chiral center on the phosphorus atom, which yields a diastereoisomer pair ([Rp] and [Sp]) at each phosphorothioate linkage. In the present invention, CL655 and CL656 were obtained and tested as racemic mixtures.

General Schemes for Preparing Active Compounds

Methods for the easy preparation of cyclic dinucleotides or prodrugs thereof disclosed herein can be prepared as described in detail below, or by other methods known to those skilled in the art. It will be understood by one of ordinary skill in the art that these schemes are in no way limiting and that variations of detail can be made without departing from the spirit and scope of the present invention.

The term "protecting group" as used herein, and unless otherwise defined, refers to a chemical functional group that is attached to an oxygen, nitrogen or phosphorus atom to prevent further reaction of that atom, or for other purposes. A wide variety of protecting groups for oxygen and for nitrogen are known to those skilled in the art of organic synthesis, and are described, for example, in (Wuts, Greene, & Greene, 2014).

Generally, cyclic dinucleotides or prodrugs thereof of the Formulas (I), (II) or (III) are prepared by first preparing the corresponding nucleoside, then preparing the 5'-hydroxy group, the functional group (OH) at the 2' position or 3' position, and then, if necessary, protecting the exocyclic amine of the purine base. Then, the appropriately protected nucleosides are converted to the corresponding 3'-phosphoramidite, 2'-phosphoramidite, 3'-H-phosphonate or 2'-H-phosphonate, which constitute the starting material for the preparation of the cyclic dinucleotides described herein.

The reaction schemes shown below apply to the synthesis of CDNs of Formula I and can be employed for the synthesis of CDNs of Formulas (II) and (III):

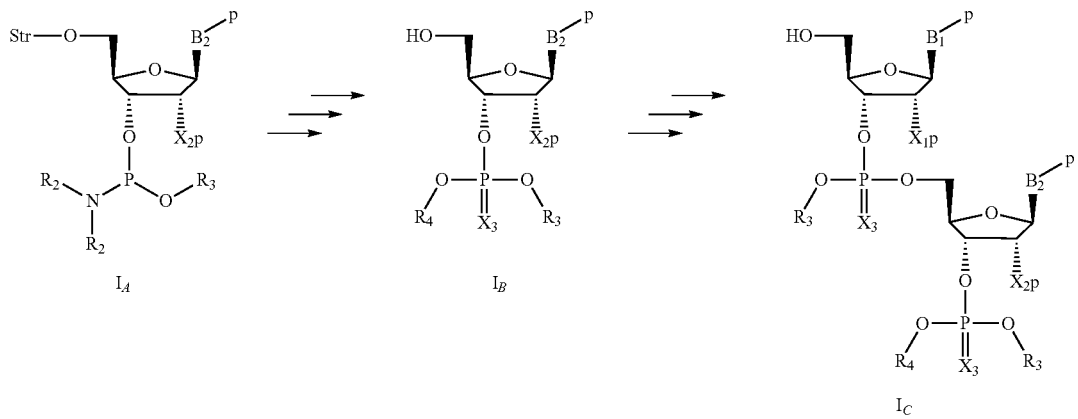

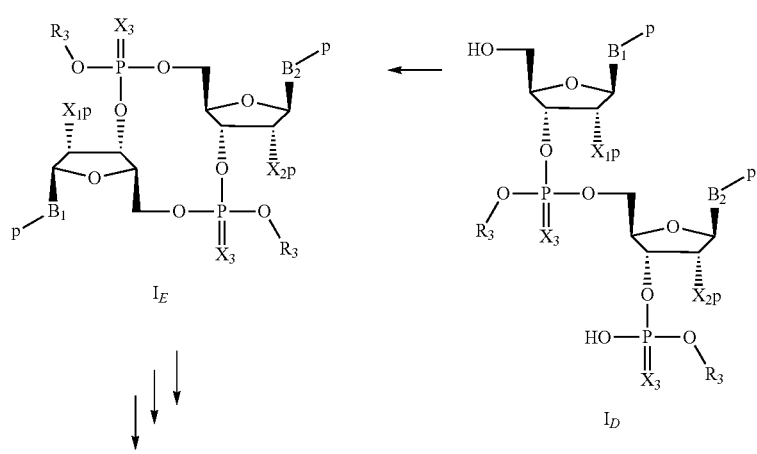

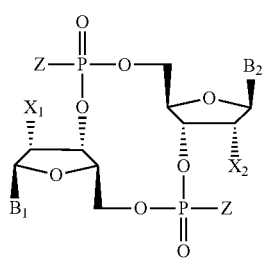

Formula I

Scheme 1 is a non-limiting example of the synthesis of active compounds of the present invention, and in particular, a synthetic approach to CDNs of Formula (I), where $B_1$, $B_2$, $X_1$, $X_2$, and Z are defined above. Str is a trityl derivative such as dimethoxytrityl (DMTr), p is a protecting group, $R_2$ is an alkyl group such as an isopropyl group, $R_3$ is a protecting group such as cyanoethyl, $R_4$ is a protecting group such as allyl, and $X_3$ is O or S.

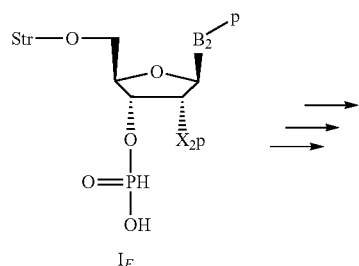

$I_F$

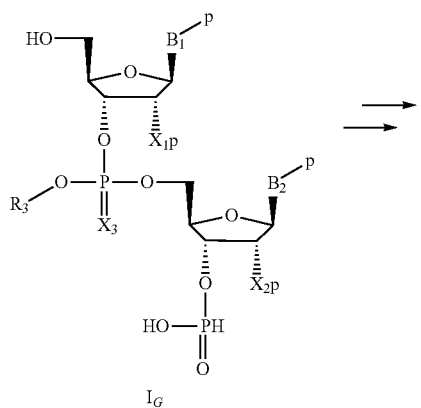

$I_G$

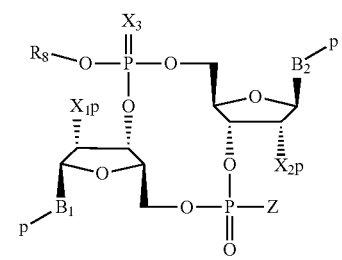

$I_H$

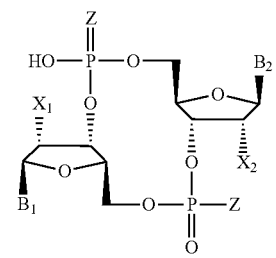

Formula I

Scheme 2 is a non-limiting example of the synthesis of active compounds of the present invention, and in particular, an alternate synthetic approach to CDNs of Formula (I), where $B_1$, $B_2$, $X_1$, $X_2$, and Z are defined above. Str is a trityl derivative such as dimethoxytrityl (DMTr), p is a protecting group, $R_2$ is an alkyl group such as an isopropyl group, $R_4$ is a protecting group such as cyanoethyl, $R_5$ is a protecting group such as allyl, and $X_3$ is O or S.

CDNs of Formulas (I) and (II) are prepared by first preparing appropriately protected phosphoramidite of Formula ($I_A$) or H-phosphonate of Formula ($I_F$):

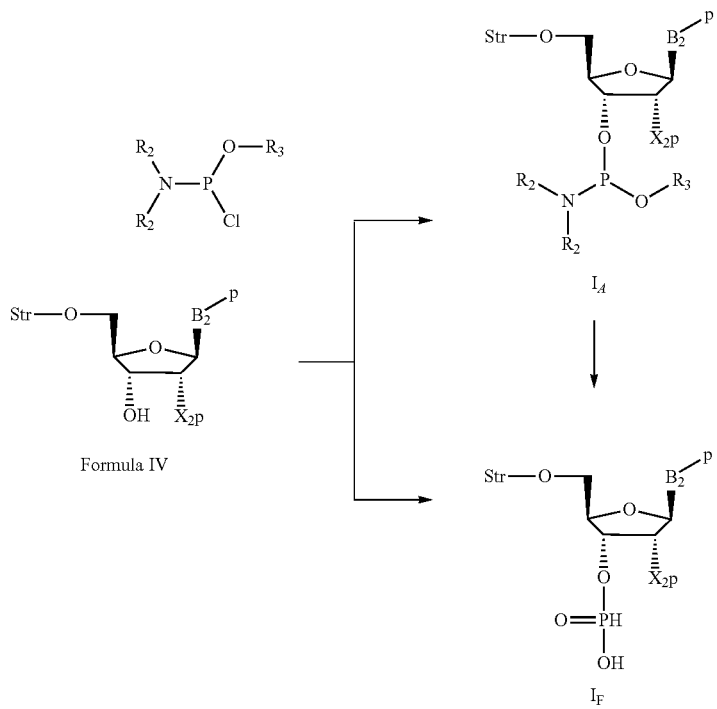

Formula IV $I_A$ $I_F$

Scheme 3 is a non-limiting example of the synthesis of phosphoramidites of Formula ($I_A$) and of H-phosphonates of Formula ($I_F$), where $B_2$, Yp, Xp, $R_7$, $R_8$, and Str are defined above.

Phosphoramidites of the Formula ($I_A$) and H-phosphonates of the Formula ($I_F$) can be synthesized by first preparing the appropriately protected nucleosides of the Formula (IV), which can be accomplished by one of ordinary skill in the art. Firstly, the base, which has an exocyclic amine, is protected, and then the 3'- and 5'-hydroxyl groups are simultaneously or selectively protected. The substitutions $X_2$ are eventually protected, using protecting groups such as TBDMS or tetrahydropyran (Thp) when $X_2$ is hydroxyl. Finally, the protecting groups at the 3'- and 5'-hydroxyls are cleaved, and the 5'-hydroxyl is subsequently protected with a trityl derivative to give the nucleoside of the Formula (IV):

FIG. 5. In vitro Type I interferon induction activity in wild-type vs. STING-knockout RAW cells. It shows relative ISG54 activity (as an indirect measurement of Type I interferon induction) of non-fluorinated vs. fluorinated cyclic dinucleotides incubated in cultures of wild-type (left-side of graph) or STING-knockout (right-side of graph) RAW cells for 24 h. WT: wild-type; SKO: STING knockout (homozygous).

FIG. 6. Type I interferon induction activity of cyclic dinucleotides in mice. Measurement of Type I interferon induction in sera from mice at 4 h post-treatment.

FIG. 7. IL-6 induction activity of cyclic dinucleotides in mice. Measurement of IL-6 induction in sera from mice at 4 h post-treatment.

FIG. 8. In vivo elimination of cyclic dinucleotides in mice. Temporal change in plasma concentration of cyclic dinucleotides in treated mice.

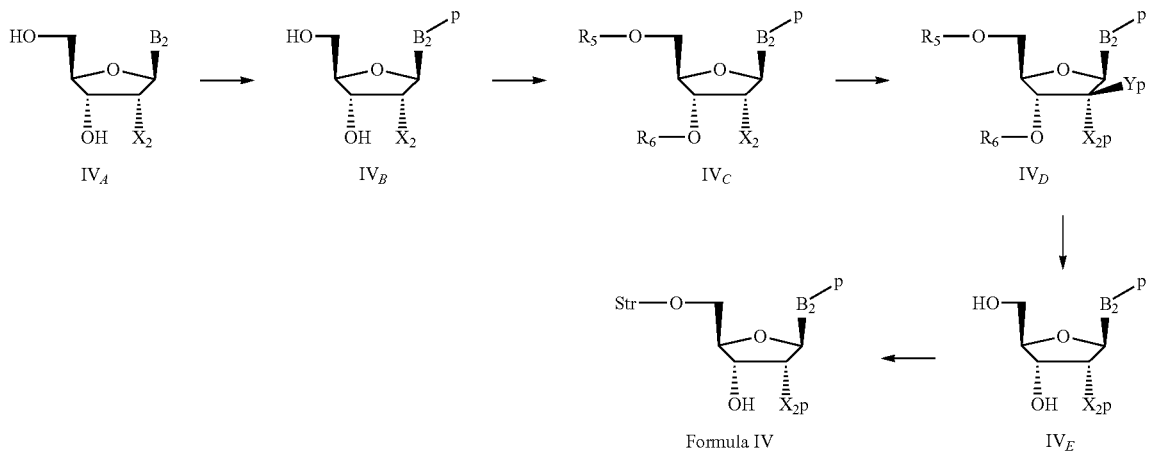

Scheme 4 is a non-limiting example of the synthesis of appropriately protected nucleoside of Formula (IV), where $B_2$, $X_2$, p, and Str are defined above. $R_5$ and $R_6$ are protecting groups.

Nucleosides of the Formula ($IV_A$) can be prepared by methods outlined in: (Chu, 2002; Rajagopalan, 2003; Schinazi, 2004; Vorbrüggen, 2001).

Figure 1:
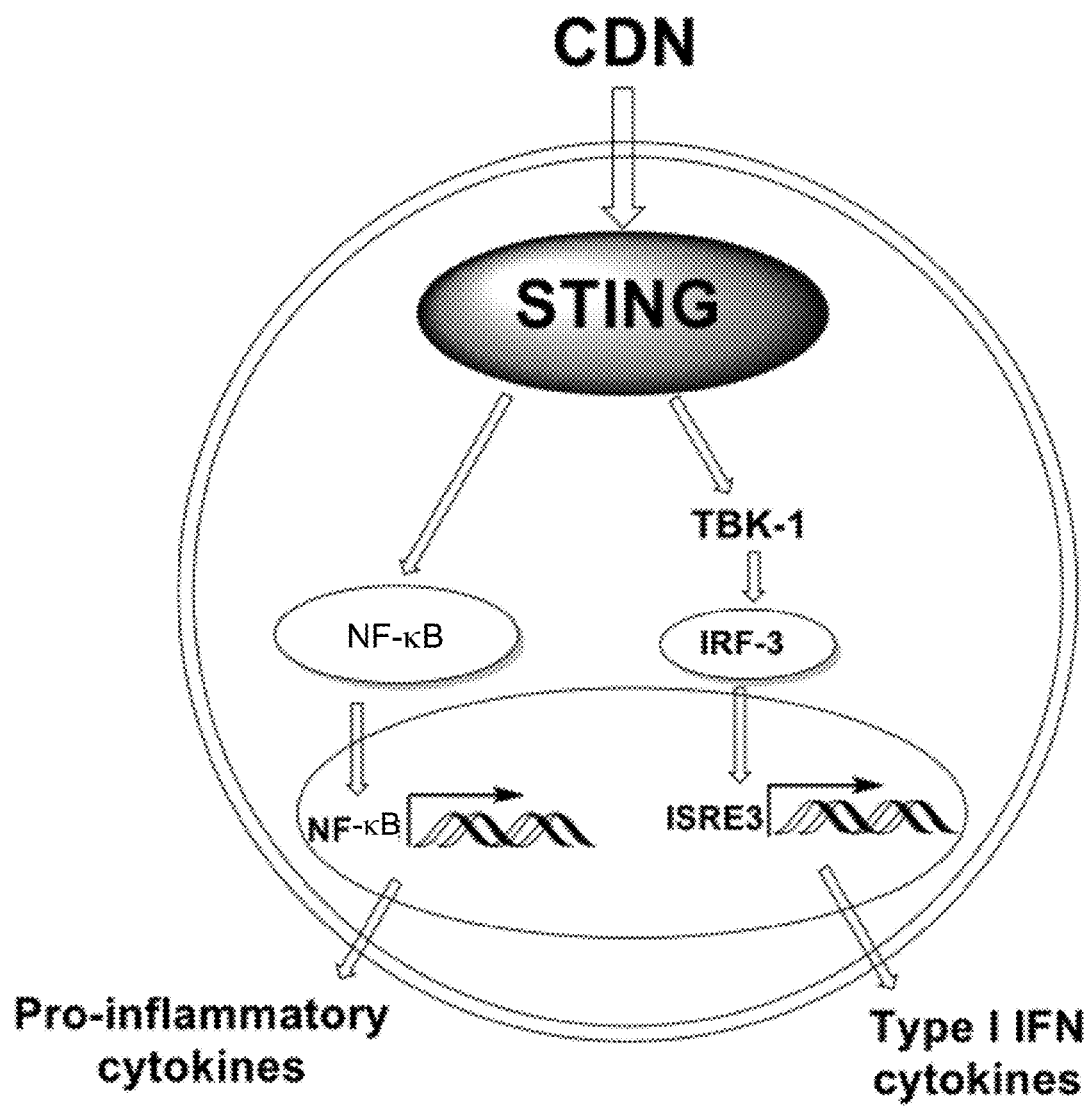
FIG. 1. STING signaling in the cell. Activation of STING by cyclic dinucleotides (CDN) leads to activation of the IRF3 and NF-κB pathways and consequently, to induction of Type I interferons and of pro-inflammatory cytokines, respectively.

The invention will be illustrated by the non-limiting following examples.

EXAMPLES

Specific compounds that are representative of this invention were prepared as per the following examples and are offered by way of illustration to aid in the understanding of the invention. They should not be construed to limit in any way the invention set forth in the claims that follow thereafter. The present compounds can also be used as intermediates in subsequent examples to produce additional compounds of the present invention. No attempt has necessarily been made to optimize the yields obtained in any of the reactions. One skilled in the art would know how to increase such yields through routine variations in reaction times, temperatures, solvents, reagents and chemical synthesis other parameters.

The present invention is further illustrated in Examples 1, which shows preparative methods for synthesizing CDNs, and in Example 2, which shows methods for the biological evaluation of these CDNs. It will be understood by one of ordinary skill in the art that these examples are in no way limiting and that variations of detail can be made without departing from the spirit and scope of the present invention.

The terms used in describing the invention are commonly used and known to those skilled in the art. As used herein, the following abbreviations have the indicated meanings:

° C. for degrees Celsius; A for adenosine; ACN for acetonitrile; aq. for aqueous; $CDCl_3$ for deuterated chloroform; $C_{18}$ for octadecyl carbon chain bonded silica; d for doublet; dA for deoxyadenosine; dd for doublet of doublets; dI for deoxyinosine; $D_2O$ for deuterium oxide; DCA for dichloroacetic acid; DCM for dichloromethane; DMSO-$d_6$ for deuterated dimethylsulfoxide; DMTrCl for 4;4'-dimethoxytrityl chloride; equiv. for equivalent; ES for electrospray ionization; $Et_2O$ for diethyl ether; EtOAc ethyl acetate; EtOH for ethanol; $Et_3N.3HF$ for triethylamine trihydrofluoride; g for grams; $^1H$ for proton; h for hours; Hz for Hertz; HPLC for high-performance liquid chromatography; I for inosine; IFN for interferon; IFN-α for interferon alpha; IFN-β for interferon beta; iPrOH for isopropanol; IRF3 for interferon regulatory factor 3; ISG (or ISG54) for interferon-stimulated gene; ISRE for interferon-stimulated response element; i.v. for intravenous; LC for liquid chromatography; m for multiplet; M for molar; m/z for mass-to-charge ratio; MeOH for methanol; mg for milligrams; $MgSO_4$ for magnesium sulfate; MHz for megahertz; min for Minutes; mL (or ml) for milliliters; mmol for millimoles; mol/L for mole/liter; MS for mass spectrometry; $NaHCO_3$ for sodium bicarbonate; $NaHSO_3$ for sodium thiosulfate; $NH_4OH$ for ammonium hydroxide; NF-κB for nuclear factor kappa-light-chain-enhancer of activated B cells; NMR for nuclear magnetic resonance; PADS for phenylacetyl disulfide; ppm for parts per million; PPTS for pyridinium p-toluenesulfonate; rt for room temperature; SEAP for secreted embryonic alkaline phosphatase; s for singlet; sl for large singlet; t for triplet; SKO for homozygous STING knockout; STING for stimulator of interferon genes; TBAF for tetra-n-butylammonium fluoride; THF for tetrahydrofuran; TBDMSCl for tert-butyldimethylsilyl chloride; TEAA for triethylammonium acetate; TFA for trifluoroacetic acid; TIPSCl2 for 1,3-dichloro-1,1,3,3-tetraisopropyldisiloxane; WT for wild type; μg for microgram; μL (or μl) for microliter; μm for micrometer; δ for chemical shift.

Anhydrous solvents and reagents suitable for nucleoside and nucleotide synthesis were purchased and were handled under dry argon or nitrogen using anhydrous technique. Amidite coupling reactions and cyclizations were performed in anhydrous acetonitrile or pyridine under dry argon or nitrogen. The starting materials for all reactions in dry pyridine were dried by concentration (three times) from pyridine. Preparative silica-gel flash chromatography was performed using Fluka 60 Å high-purity grade or Merck Grade 9385 silica using gradients of methanol in dichloromethane. Analytical LC/ES MS was performed on an Agilent 1290 Infinity UHPLC system coupled to a diode array detector (DAD) Agilent 1260 Infinity and an Agilent 6130 Quadrupole mass spectrometer equipped with an electrospray ionization source (ESI) and controlled by Chemstation software. The LC system was equipped with an Aquity CSH C18 50×2.1 mm 1.7 μm column using gradients of 10 mM ammonium formate and acetonitrile at 300 μl/min flow. The UV detection wavelength was 254 nm. The mass spectrometer was operated in positive and negative ESI modes Preparative HPLC was performed on a Waters preparative 150Q HPLC system monitoring at 254 nm on a SunFire Prep C18 5 μm OBD 30×150 mm column using gradients of 10 mM ammonium formate and acetonitrile at a flow rate 60 mL/min. The $^1H$ NMR spectra were acquired on either a Bruker 300 MHz (Fourier 300) at room temperature and reported in ppm downfield. Molecular sieves (MS) 3 Å were employed after drying the commercially supplied product at 250° C. for 12 h under vacuum. The commercial nucleoside phosphoramidites were supplied from Chemgenes.

The following examples serve to illustrate the present invention. These examples are in no way intended to limit the scope of the invention.

Example 1: Synthesis of the Compounds of the Invention

Example 1.A: General Protocol for Preparation of Phosphotriester

The appropriately protected phosphoramidite or commercially available phosphoramidite was coevaporated three times with dry ACN, and the resulting solid was dissolved in a solution of Activator42® (0.1 mol/L, 2 equiv.) in the presence of molecular sieves 3 Å. To the solution was added allyl alcohol (2 equiv.) and the resulting mixture was stirred for 30 min.

For Phosphotriester Linkage:

Tert-butyl hydroperoxide in decane (5.5 M, 2 equiv.) was added to the mixture, which was stirred for 40 min. The solution was filtered and the molecular sieves were washed with DCM. The filtrate was concentrated in vacuo.

For Phosphorothioate Triester Linkage:

The mixture was concentrated in vacuo and the residue was dissolved in a solution of PADS (2.5 equ) 0.2 M in dry pyridine. The mixture was stirred at rt for 45 min. The solution was filtered and the molecular sieves were washed with DCM. The filtrate was concentrated in vacuo and coevaporated three times with ACN.

The residue was treated with a solution of DCA/DCM (3%) in the presence of water (10 equiv.) for 15 min. The reaction was quenched with addition of MeOH and pyridine. The solvents were removed in vacuo and the residue was purified by silica-gel column chromatography, using DCM/MeOH as eluent. The structure of the compound was confirmed by LC-ES/MS analysis with ions at $[M-H]^-$ and/or $[M+H]^+$.

Example 1.B: General Protocol for Preparation of H-Phosphonate

The appropriately protected phosphoramidite or commercial phosphoramidite was dissolved in a solution of ACN. To the solution were added water (2 equiv.) and pyridium TFA (1.2 equiv.), and the mixture was stirred for 15 min. Then, the solvents were removed in vacuo. The residue was treated with a solution of DCA/DCM (3%) in the presence of water (10 equiv.) for 15 min. The reaction was quenched with addition of MeOH and pyridine. The solvents were removed in vacuo and the residue was purified by silica-gel column chromatography, using DCM/MeOH as eluent. The structure of the compound was confirmed by LC-ES/MS analysis with ions at $[M-H]^-$ and/or $[M+H]^+$.

Example 1.C: Protocol for the Dinucleotide Synthesis

To a solution of compound of Example 1.A or appropriately protected compound in a solution of Activator42® (0.1 mol/L, 2 equiv.) in the presence of molecular sieves 3 Å was added in one portion an appropriately protected phosphoramidite or commercial phosphoramidite. The mixture was stirred for 30 min.

For Phosphotriester Linkage:

Tert-butyl hydroperoxide in decane (5.5 M, 2 equiv.) was added to the mixture, which was stirred for 40 min. The solution was filtered and the molecular sieves were washed with DCM. The filtrate was concentrated in vacuo.

For Phosphorothioate Triester Linkage:

The mixture was concentrated in vacuo and the residue was dissolved in a solution of PADS (2.5 equ) 0.2 M in dry pyridine. The mixture was stirred at rt for 45 min. The solution was filtered and the molecular sieves were washed with DCM. The filtrate was concentrated in vacuo and coevaporated three times with ACN.

The residue was treated with a solution of DCA/DCM (3%) in the presence of water (10 equiv.) for 15 min. The reaction was quenched by addition of MeOH and pyridine. The solvents were removed in vacuo and the residue was purified by silica-gel column chromatography, using DCM/MeOH as eluent. The structure of the compound was confirmed by LC-ES/MS analysis with ions at [M−H]⁻ and/or [M+H]⁺.

Example 1.D: Alternative Protocol for the Dinucleotide Synthesis

To a solution of compound of Example 1.B in a solution of Activator42® (0.1 mol/L, 2 equiv.) in the presence of molecular sieves 3 Å was added in one portion an appropriately protected phosphoramidite or commercial phosphoramidite. The mixture was stirred for 30 min.

For Phosphotriester Linkage:

Tert-butyl hydroperoxide in decane (5.5 M, 2 equiv.) was added to the mixture, which was stirred for 40 min. The solution was filtered and the molecular sieves were washed with DCM. The filtrate was concentrated in vacuo.

For Phosphorothioate Triester Linkage:

The mixture was concentrated in vacuo and the residue was dissolved in a solution of PADS (2.5 equ) 0.2 M in dry pyridine. The mixture was stirred at rt for 45 min. The solution was filtered and the molecular sieves were washed with DCM. The filtrate was concentrated in vacuo and coevaporated three times with ACN.

The residue was treated with a solution of DCA/DCM (3%) in the presence of water (10 equiv.) for 15 min. The reaction was quenched with addition of MeOH and pyridine. The solvents were removed in vacuo and the residue was purified by silica-gel column chromatography, using DCM/MeOH as eluent. The structure of the compound was confirmed by LC-ES/MS analysis with ions at [M−H]⁻ and/or [M+H]⁺.

Example 1.E: Protocol to Remove Allyl Group

To a solution of dinucleotide from Example 1.C in acetone was added sodium iodide (10 equiv.), and the resulting suspension was stirred under reflux for 2 h. The resulting colorless precipitate was collected by filtration and washed with chilled acetone. This precipitate is highly hygroscopic and thus, was immediately used in the next procedure. The structure of the compound was confirmed by LC-ES/MS analysis with ions at [M−H]⁻ and/or [M+H]⁺.

Example 1.F: Alternative Protocol to Remove Allyl Group

To a solution of dinucleotide from Example 1.C in dry THF was added N-methyl aniline (3 equiv.) and tetrakis (triphenylphosphine)palladium(0) (0.2 equiv.). The resulting suspension was stirred at rt for 15 min. Then, the solvent was removed in vacuo and the residue was triturated with diethyl ether. The resulting colorless precipitate was collected by filtration and washed with chilled diethyl ether. This precipitate was purified by silica-gel column chromatography, using DCM/MeOH as eluent. The structure of the compound was confirmed by LC-ES/MS analysis with ions at [M−H]⁻ and/or [M+H]⁺.

Example 1.G: Protocol for Cyclization of the Dinucleotide

The solid obtained in Example 1.E or 1.F was coevaporated three times with dry pyridine and then, dry ACN. The residue was suspended in THF, and to the resulting heterogeneous mixture were successively added N-methylimidazole (10 equiv.) and 2,4,6-triisopropylbenzenesulfonyl chloride (10 equiv.). The resulting mixture was stirred at 25° C. for 3 h to 36 h. Then, the solvent was removed in vacuo and the residue was triturated with EtOAc. The resulting colorless precipitate was collected by filtration and washed with chilled EtOAc. This precipitate was used in the next step without any further purification. The structure of the compound was confirmed by LC-ES/MS analysis with ions at [M−H]⁻ and/or [M+H]⁺.

Example 1.H: Alternative Protocol for Cyclization of the Dinucleotide

The solid obtained from Example 1.E or 1.F was coevaporated three times with dry pyridine. The residue was suspended in dry pyridine, and to the resulting solution was added 1-(Mesitylene-2-sulfonyl)-3-nitro-1,2,4-triazole (MSNT) (5 equiv.). The resulting mixture was stirred at 25° C. for 3 h to 18 h. Then, the solvent was removed in vacuo, and the resulting product used in the next step without any further purification. The structure of the compound was confirmed by LC-ES/MS analysis with ions at [M−H]⁻ and/or [M+H]⁺.

Example 1.I: Alternative Protocol for Cyclization of the Dinucleotide

The solid obtained in Example 1.D or appropriately protected compound was coevaporated three times with dry pyridine. The residue was suspended in dry pyridine, and to the resulting solution was added 5,5-dimethyl-2-oxo-2-chloro-1,3,2-dioxaphosphinane (DMOCP) (3 equiv.). The resulting mixture was stirred at 25° C. for 3 h to 18 h.

For Phosphodiester Linkage:

Iodine (1.3 equiv.) and water (30 equiv.) were added to the mixture. After 10 min aq. NaHSO₃ (0.15%) was added until complete decoloration was observed, and then aq. NaHCO₃ was added. The aqueous layer was extracted three times with a 1:1 (v/v) mixture of EtOAc/Et₂O. The organic layers were pooled, dried over MgSO₄, filtered, and then concentrated in vacuo.

For Phosphorothioate Triester Linkage:

Elemental sulfur (5 equiv.) was added. The mixture was stirred at rt for 45 min. Then the mixture was concentrated in vacuo and coevaporated three times with toluene, precipitated in ACN to removed excess of sulfur and concentrated in dryness.

The residue was used in the next step without any further purification. The structure of the compound was confirmed by LC-ES/MS analysis with ions at [M−H]⁻ and/or [M+H]⁺.

Example 1.J: Protocol for the Deprotection and Purification of Cyclic Dinucleotides The protected cyclic dinucleotide of Example 1.G, 1.H or 1.I was treated with a solution of methylamine in EtOH (33%), and the resulting mixture was stirred at 50° C. for 4 h. The reaction mixture was concentrated, and the resulting residue was dried in vacuo. The dried material was mixed with $Et_3N.3HF$ (25 equiv.) and stirred at 25° C. for 6 h. To this mixture was added a 1 M ammonium formate buffer solution, and the mixture was vigorously stirred at 30° C. to 40° C. for 10 min. The resulting precipitate was filtered, and the filtrate was subjected to preparative HPLC using a $C_{18}$ Sunfire column (19×150 mm, 5 μm) and ammonium formate/ACN as eluent. The fractions containing the desired compound were pooled and lyophilized. The structure of the compound was confirmed by LC-ES/MS analysis with ions at [M–H]⁻ and/or [M+H]⁺.

Example 1.K: Protocol for the Deprotection and Purification of Cyclic Dinucleotides The protected cyclic dinucleotide of Example 1.G, 1.H or 1.I was treated with a solution of methylamine in EtOH (33%), and the resulting mixture was stirred at 50° C. for 4 h. The reaction mixture was concentrated, and the resulting residue was subjected to preparative HPLC using a $C_{18}$ Sunfire column (19×150 mm, 5 μm) and ammonium formate/ACN as eluent. The fractions containing the desired compound were pooled and lyophilized. The structure of the compound was confirmed by LC-ES/MS analysis with ions at [M–H]⁻ and/or [M+H]⁺.

Intermediate 1: 2'-O(TBDMS)-3'-O(H-phosphonate)-N⁶(Bz)Adenosine

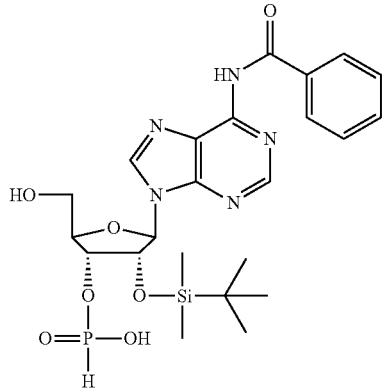 [SMILES: CC(C)(C)[Si](C)(C)O[C@H]1C(n2cnc3c(NC(=O)c4ccccc4)ncnc32)OC(CO)[C@H]1O[PH](=O)O]

Intermediate 1 was prepared from the commercially available phosphoramidite of Adenosine using a similar procedure to that described in Example 1.B to provide 6.20 g (93% yield) of intermediate 1. LC-MS: Rt=4.41 min, m/z=550 [M+H]⁺, m/z=548 [M–H]⁻

Intermediate 2: [2'-O(TBDMS)-3'-O(CE)phosphotriester-Inosine]-(3',5')-[2'-O(TBDMS)-3'-O(H-phosphonate)-N⁶(Bz)Adenosine]

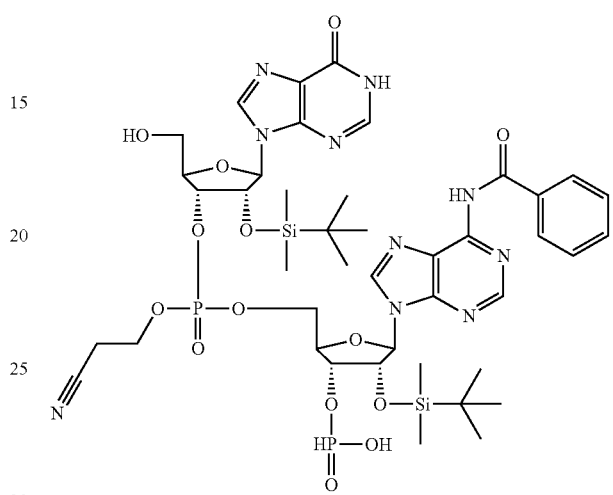

Intermediate 2 was prepared from intermediate 1 and the commercially available phosphoramidite of Inosine using a similar procedure to that described in Example 1.D to provide 8.04 g (68% yield) of intermediate 2. LC-MS: Rt=5.22 min, m/z=1048 [M+H]⁺, m/z=1046 [M–H]⁻.

Intermediate 3: (3',3')Cyclic-[2'-O(TBDMS)-3'-O(phosphodiester)-N⁶(Bz)Adenosine]-[2'-O(TBDMS)-3'-O(CE)phosphotriester-Inosine]

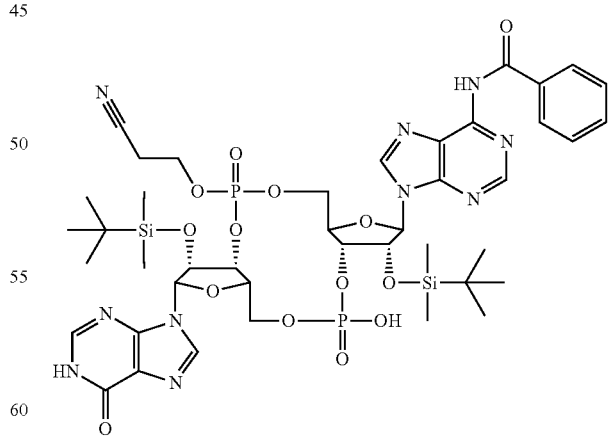

Intermediate 3 was prepared from intermediate 2 using a similar procedure to that described in Example 1.I to provide 8.04 g (68% yield) of intermediate 3. LC-MS: Rt=5.41 min, m/z=1046 [M+H]⁺, m/z=1044 [M–H]⁻.

Intermediate 4: (5',3')-O(TIPS)Inosine

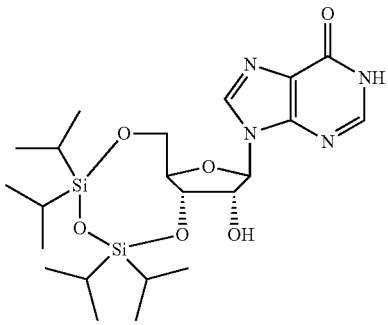

To a solution of Inosine (10.0 g, 37.2 mmol) in dry pyridine (200 mL) was added TIPSCl$_2$ (14.1 g, 44.7 mmol). The solution was stirred for 18 h at rt. Then, the reaction was quenched by addition of MeOH (50 mL) and the solvents were removed in vacuo. The residue was dissolved in EtOAc and washed with saturated aq. NaHCO$_3$, water and brine. The organic layer was dried over MgSO$_4$, filtered, and then concentrated in vacuo. The crude compound was purified by silica-gel column chromatography, using DCM/MeOH as eluent, to give 13.5 g (70% yield) intermediate 4. LC-MS: Rt=5.32 min, m/z=511 [M+H]$^+$, m/z=509 [M−H]$^-$. $^1$H NMR (CDCl$_3$-d$_1$, 300 MHz) δ (ppm) 13.04 (s, 1H), 8.10 (s, 1H), 8.03 (s, 1H), 5.99 (s, 1H), 4.93 (t, 1H), 4.50 (d, 1H), 4.11 (m, 3H), 1.83 (m, 4H), 1.09 (m, 32H).

Intermediate 5: (5',3')-O(TIPS)-2'-O(Thp)Inosine

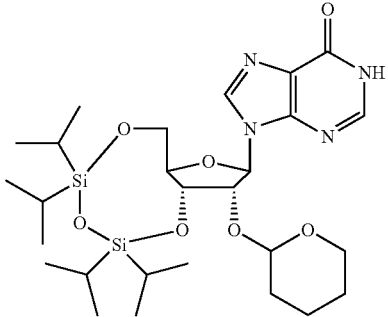

To a solution of intermediate 4 (5 g, 9.79 mmol) in dry DCM (75 mL) were added 3,4-dihydro-2H-pyran (24.7 g, 293.7 mmol) and PPTS (7.38 g, 29.37 mmol). The solution was stirred for 18 h at rt. Then, the reaction was quenched by a saturated solution of NaHCO$_3$. The different layers were separated and the organic layer was washed with water and brine, dried over MgSO$_4$, filtered, and then concentrated in vacuo. The crude compound was purified by silica-gel column chromatography, using DCM/MeOH as eluent, to give 4.71 g (80% yield) of intermediate 5. LC-MS: Rt=6.72 min, m/z=595 [M+H]$^+$, m/z=593 [M−H]$^-$. $^1$H NMR (CDCl$_3$-d$_1$, 300 MHz) δ (ppm) 12.89 (d, 1H), 8.12 (s, 1H), 8.09 (s, 1H), 8.04 (d, 1H), 6.05 (d, 1H), 5.07 (t, 1H), 4.76 (m, 1H), 4.53 (m, 2H), 4.40-4.05 (m, 5H), 1.85-1.55 (m, 10H), 1.04 (m, 32H).

Intermediate 6: 2'-O(Thp)Inosine

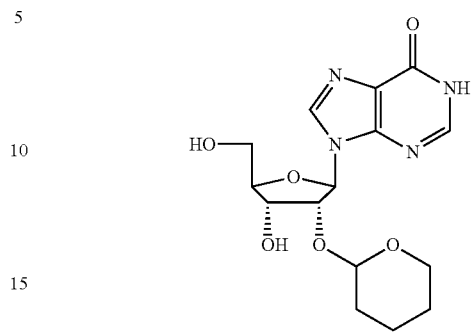

To a solution of intermediate 5 (4.71 g, 7.92 mmol) in THF (100 mL) was added TBAF on silica gel (10.56 g, 15.84 mmol). The solution was stirred for 3 h at rt. Then, the reaction was filtered, the silica gel was washed with THF, and the filtrate was concentrated in vacuo. The crude compound was purified by silica-gel column chromatography, using DCM/MeOH as eluent, to give 2.7 g (96% yield) of intermediate 6. LC-MS: Rt=4.32 min, m/z=353 [M+H]$^+$, m/z=351 [M−H]$^-$.

Intermediate 7: 5'-O(DMTr)-2'-O(Thp)Inosine

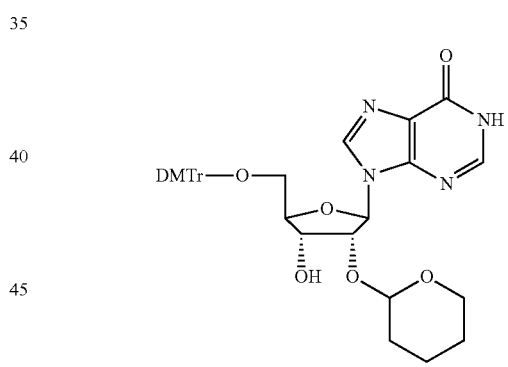

To a solution of intermediate 6 (2.70 g, 7.66 mmol) in dry pyridine (40 mL) was added dropwise a solution of DMTrCl (2.17 g, 6.42 mmol) in DCM (5 mL). The solution was at rt for 2 h. Then, the reaction was quenched by addition of 5% aq. NaHCO$_3$ (110 mL), the aqueous layer was extracted three times with DCM. The organic layers were pooled and dried over MgSO$_4$, filtered, and then concentrated in vacuo. The residue was purified by silica-gel column chromatography, using 1% pyridine in DCM/MeOH as eluent, to give 4.78 g (95% yield) of intermediate 7. LC-MS: Rt=6.80 min, m/z=655 [M+H]$^+$, m/z=653 [M−H]$^-$. $^1$H NMR (CDCl$_3$-d$_1$, 300 MHz) δ (ppm) 12.80 (s, 1H), 8.02 (s, 1H), 8.00 (s, 1H), 7.71 (m, 2H), 7.73 (m, 2H), 7.24 (m, 9H), 6.20 (d, 1H), 5.07 (t, 1H), 4.83 (m, 1H), 4.35 (m, 2H), 3.78 (s, 6H), 3.45-3.30 (m, 4H), 1.77-1.56 (m, 6H).

Intermediate 8: 5'-O(DMTr)-3'-O(TBDMS)-2'-O(Thp)Inosine

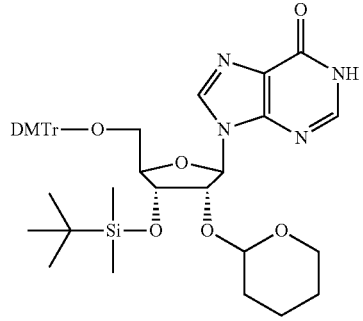

To a solution of intermediate 7 (4.78 g, 7.30 mmol) in dry pyridine (40 mL) were added imidazole (1.29 g, 18.98 mmol) and TBDMSCl (1.43 g, 9.49 mmol), the reaction was stirred for 18 h at rt. Then, the reaction was diluted with DCM (100 mL), the solution was washed with saturated aq. NaHCO$_3$, water and brine. The organic layer was dried over MgSO$_4$, filtered, and then concentrated in vacuo. The residue was purified by silica-gel column chromatography, using 1% pyridine in DCM/MeOH as eluent, to give ((5.12 g (91% yield) of intermediate 8. LC-MS: Rt=8.15 min, m/z=769 [M+H]$^+$, m/z=767 [M−H]$^-$. 1H NMR (CDCl$_3$-d$_1$, 300 MHz) δ (ppm) 12.70 (s, 1H), 8.02 (s, 1H), 7.97 (s, 1H), 7.40 (m, 2H), 7.26 (m, 11H), 6.09 (d, 1H), 4.80 (m, 1H), 4.36 (m, 1H), 4.16 (m, 2H), 3.72 (s, 6H), 3.45-3.26 (m, 4H), 1.61-1.37 (m, 8H), 0.81 (s, 9H), 0.09 (dd, 6H).

Intermediate 9: 3'-O(TBDMS)-2'-O(Thp)Inosine

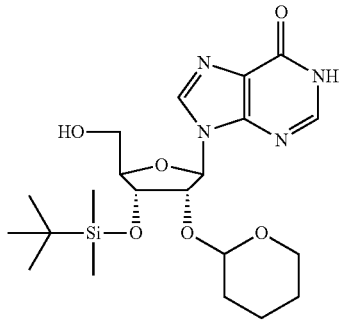 [SMILES: CC(C)(C)[Si](C)(C)O[C@@H]1C(CO)OC(n2cnc3c(=O)[nH]cnc32)[C@@H]1OC1CCCCO1]

The intermediate 8 (4.93 g, 6.41 mmol) was dissolved in a solution of ZnBr$_2$ (0.5 M) in DCM/iPrOH (1/1) (40 mL, 19.3 mmol). The solution was stirred for 40 min at rt. The reaction was neutralized with 1N NaHCO$_3$ solution. The different layers were separated and the organic layer was washed with water and brine, dried over MgSO$_4$, filtered, and then concentrated in vacuo. The residue was purified by silica-gel column chromatography, using DCM/MeOH as eluent to give 2.68 g (90% yield) of intermediate 9. LC-MS: Rt=6.22 min, m/z=467 [M+H]$^+$, m/z=465 [M−H]$^-$.

Intermediate 10: [2'-O(TBDMS)-3'-O(CE)phosphotriester-N$^6$(Bz)Adenosine]-(3',5')-[3'-O(TBDMS)-2'-O(Thp)Inosine]

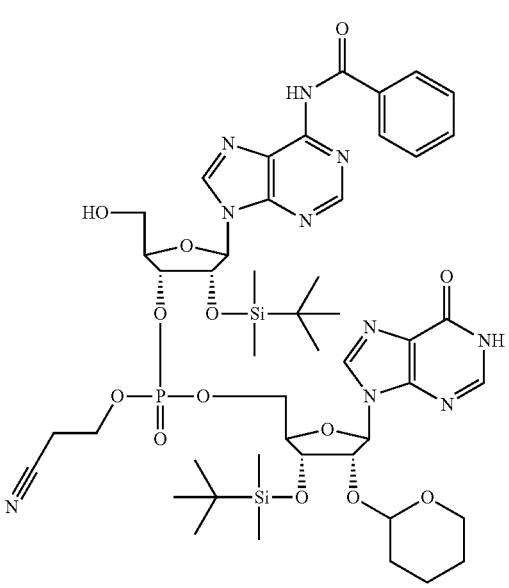 [SMILES: CC(C)(C)[Si](C)(C)O[C@@H]1C(COP(=O)(OCCC#N)O[C@@H]2C(CO)OC(n3cnc4c(NC(=O)c5ccccc5)ncnc43)[C@@H]2O[Si](C)(C)C(C)(C)C)OC(n2cnc3c(=O)[nH]cnc32)[C@@H]1OC1CCCCO1]

Intermediate 10 was prepared from intermediate 9 and the commercially available phosphoramidite of Adenosine using a similar procedure to that described in Example 1.C to give 1.9 g (64% yield) of intermediate 10. Rt=6.99 min, m/z=1068 [M+H]$^+$, m/z=1066 [M−H]$^-$.

Intermediate 11: [5'-O(H-phosphonate)-2'-O(TBDMS)-3'-O(CE)phosphotriester-N$^6$(Bz)Adenosine]-(3',5')-[3'-O(TBDMS)-2'-O(Thp)Inosine]

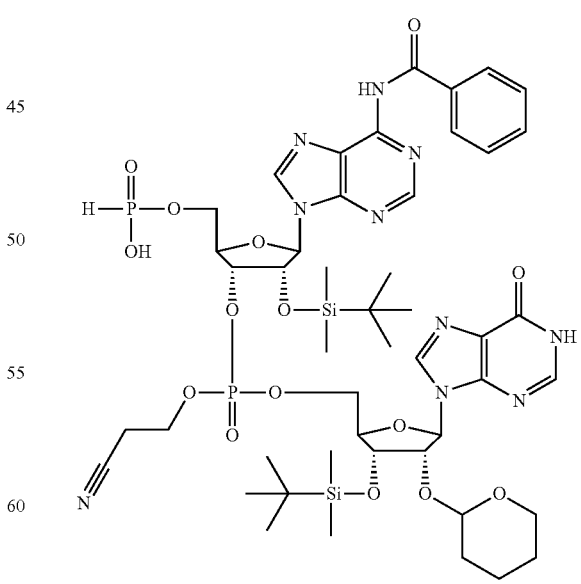

To a solution of intermediate 10 (1.9 g, 1.78 mmol) in dry pyridine (20 mL) was added diphenylphosphite (1.25 g, 5.34 mmol). The reaction was stirred for 2 h at rt. To the reaction was added a solution of TEAA 0.1 M (53 mL, 5.34 mmol).

The reaction was stirred for 45 min at rt. Then, the solvents were removed in vacuo and the residue was dissolved in DCM (100 mL). The organic layer was washed with aq. NaHCO$_3$ (5%) solution, water and brine, dried over MgSO$_4$, filtered, and then concentrated in vacuo to give 2.0 g (99% yield) of crude intermediate 11. This intermediate was used in the next step without any further purification. LC-MS: Rt=6.06 min, m/z=1132 [M+H]$^+$, m/z=1130 [M−H]$^-$.

Intermediate 12: [5'-O(H-phosphonate)-2'-O(TBDMS)-3'-O(CE)phosphotriester-N$^6$(Bz)Adenosine]-(3',5')-[3'-O(TBDMS)Inosine]

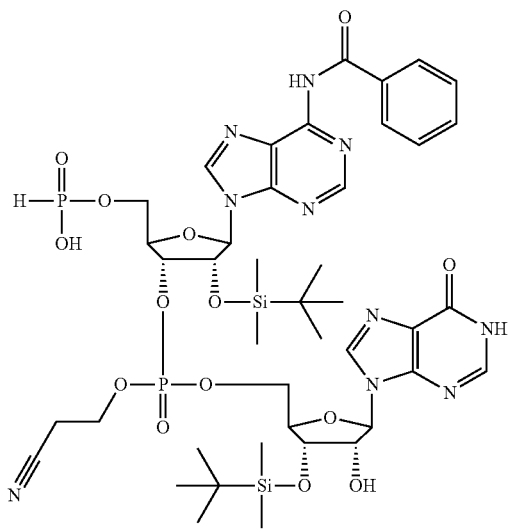 [SMILES: CC(C)(C)[Si](C)(C)O[C@@H]1C(COP(=O)(OCCC#N)O[C@@H]2C(CO[PH](=O)O)OC(n3cnc4c(NC(=O)c5ccccc5)ncnc43)[C@@H]2O[Si](C)(C)C(C)(C)C)OC(n2cnc3c(=O)[nH]cnc32)[C@@H]1O]

The intermediate 11 (2.0 g, 2.12 mmol) was treated with a solution of DCA 10% in DCM (50 mL). The reaction was stirred for 2 h at rt. Then, the reaction was neutralized by addition of pyridine (17 mL). The solvents were removed in vacuo to give 2.2 g (100% yield) of crude intermediate 12. This intermediate was used in the next step without any further purification. LC-MS: Rt=7.38 min, m/z=1048 [M+H]$^+$, m/z=1046 [M−H]$^-$.

Intermediate 13: (3',2')Cyclic-[2'-O(TBDMS)-3'-O(CE)phosphotriester-N$^6$(Bz)Adenosine]-[2'-O(phosphodiester)-3'-O(TBDMS)Inosine]

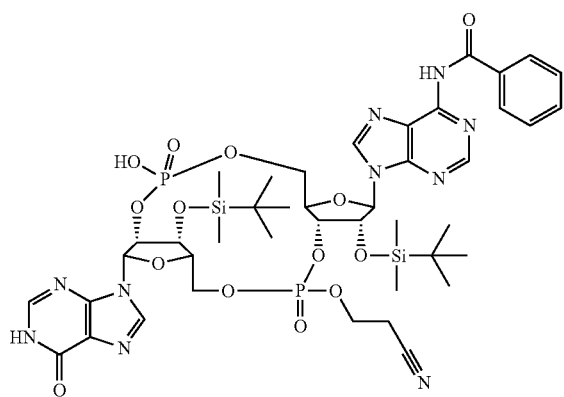 [SMILES: CC(C)(C)[Si](C)(C)O[C@@H]1C2COP(=O)(OCCC#N)O[C@@H]3C(COP(=O)(O)O[C@H]1C(n1cnc4c(=O)[nH]cnc41)O2)OC(n1cnc2c(NC(=O)c4ccccc4)ncnc21)[C@@H]3O[Si](C)(C)C(C)(C)C]

Intermediate 13 was prepared from intermediate 12 using a similar procedure to that described in Example 1.I to provide 1.73 g (83% yield) of intermediate 13. LC-MS: Rt=7.20 min, m/z=1046 [M+H]$^+$, m/z=1044 [M−H]$^-$.

Intermediate 14: [3'-O(TBDMS)-2'-O(CE)phosphotriester-N$^6$(Bz)Adenosine]-(3',5')-[3'-O(TBDMS)-2'-O(Thp)Inosine]

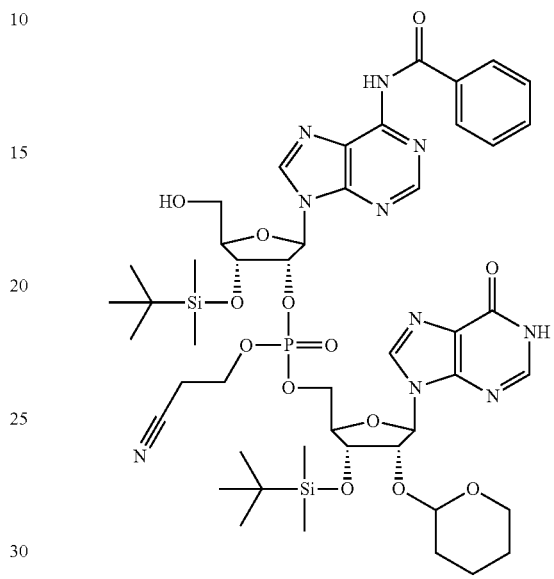

Intermediate 14 was prepared from intermediate 9 and the commercially available phosphoramidite of adenosine using a similar procedure to that described in Example 1.C to provide 1.9 g (60% yield) of intermediate 14. Rt=7.08 min, m/z=1068 [M+H]$^+$, m/z=1066 [M−H]$^-$.

Intermediate 15: [5'-O(H-phosphonate)-3'-O(TBDMS)-2'-O(CE)phosphotriester-N$^6$(Bz)Adenosine]-(3',5')-[3'-O(TBDMS)-2'-O(Thp)Inosine]

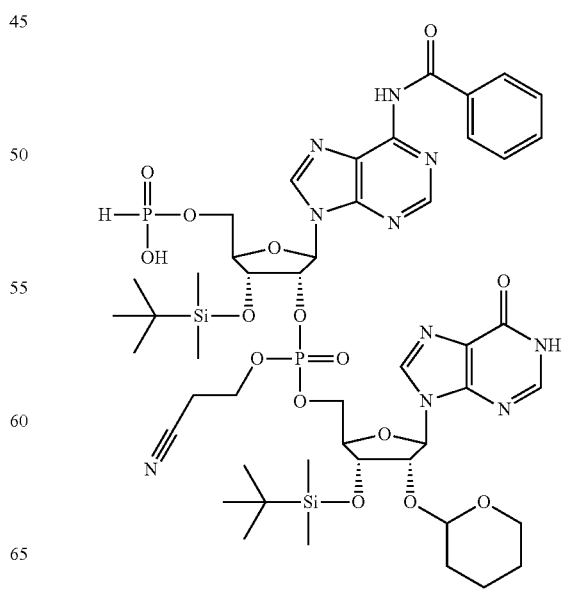

To a solution of intermediate 14 (1.9 g, 1.78 mmol) in dry pyridine (20 mL) was added diphenylphosphite (1.25 g, 5.34 mmol). The reaction was stirred at rt for 2 h. To the reaction was added a solution of TEAA 0.1 M (53 mL, 5.34 mmol). The reaction was stirred for 45 min at rt. Then, the solvents were removed in vacuo and the residue was dissolved in DCM (100 mL). The organic layer was washed with aq. NaHCO$_3$ (5%) solution, water and brine, dried over MgSO$_4$, filtered, and then concentrated in vacuo to give 2.0 g (99% yield) of crude intermediate 15. This intermediate was used in the next step without any further purification. LC-MS: Rt=6.11 min, m/z=1132 [M+H]$^+$, m/z=1130 [M−H]$^-$.

Intermediate 16: [5'-O(H-phosphonate)-2'-O(TBDMS)-3'-O(CE)phosphotriester-N$^6$(Bz)Adenosine]-(3',5')-[3'-O(TBDMS)Inosine]

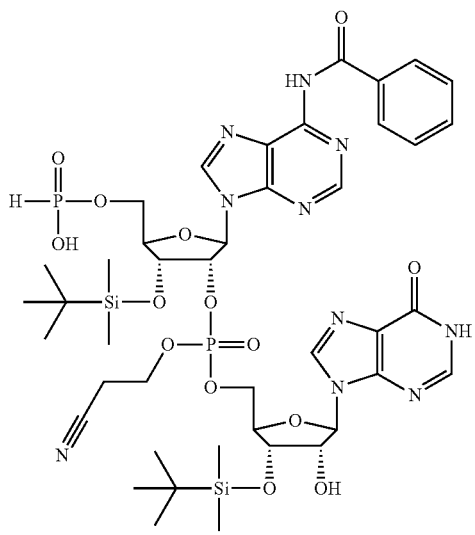 [SMILES: CC(C)(C)[Si](C)(C)O[C@@H]1C(COP(=O)(OCCC#N)O[C@H]2C(n3cnc4c(NC(=O)c5ccccc5)ncnc43)OC(CO[PH](=O)O)[C@H]2O[Si](C)(C)C(C)(C)C)OC(n2cnc3c(=O)[nH]cnc32)[C@@H]1O]

The intermediate 15 (2.0 g, 1.76 mmol) was treated with a solution of DCA 10% in DCM (50 mL, 85.0 mmol). The reaction was stirred at rt for 2 h. Then, the reaction was neutralized by addition of pyridine (17 mL, 177.0 mmol). The solvents were removed in vacuo to give 1.8 g (100% yield) of crude intermediate 16. This intermediate was used in the next step without any further purification. LC-MS: Rt=5.39 min, m/z=1048 [M+H]$^+$, m/z=1046 [M−H]$^-$.

Intermediate 17: (2',2')Cyclic-[3'-O(TBDMS)-2'-O(CE)phosphotriester-N$^6$(Bz)Adenosine]-[2-O(phosphodiester)-3-O(TBDMS)Inosine]

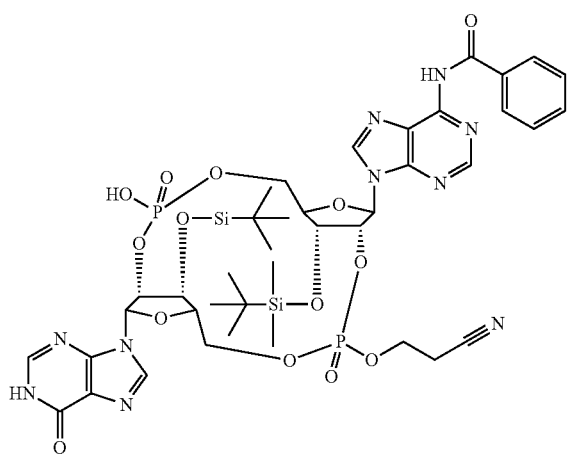

Intermediate 17 was prepared from intermediate 16 using a similar procedure to that described in Example 1.I to provide 1.5 g (75% yield) of intermediate 17. LC-MS: Rt=5.41 min, m/z=1046 [M+H]$^+$, m/z=1044 [M−H]$^-$.

Intermediate 18: 3'-O(TBDMS)-2'-O(H-phosphonate)-N$^6$(Bz)Adenosine

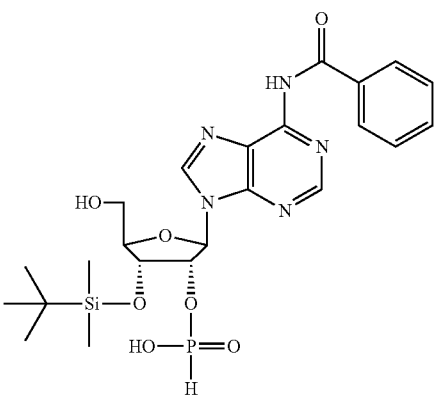 [SMILES: CC(C)(C)[Si](C)(C)O[C@@H]1C(CO)OC(n2cnc3c(NC(=O)c4ccccc4)ncnc32)[C@@H]1O[PH](=O)O]

Intermediate 18 was prepared from the commercially available phosphoramidite of Adenosine using a similar procedure to that described in Example 1.B to provide 1.1 g (94% yield) of intermediate 18. LC-MS: Rt=4.47 min, m/z=550 [M+H]$^+$, m/z=548 [M−H]$^-$.

Intermediate 19: [2'-O(TBDMS)-3'-O(CE)phosphotriester-Inosine]-(3',5')-[3'-O(TBDMS)-2'-O(H-phosphonate)-N$^6$(Bz)Adenosine]

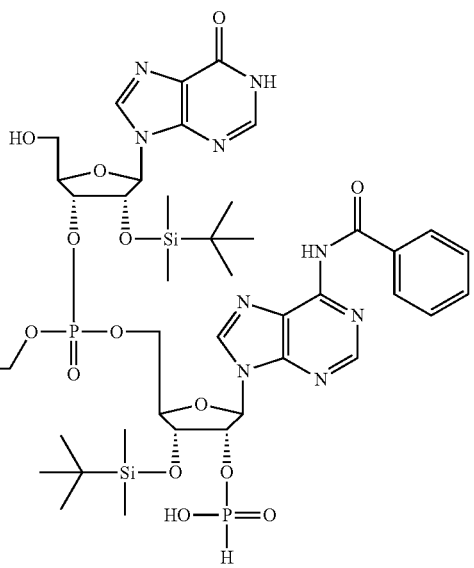

Intermediate 19 was prepared from intermediate 18 and commercially available phosphoramidite of Inosine using a similar procedure to that described in Example 1.D to provide 410 mg (44% yield) of intermediate 19. Rt=4.70 min, m/z=1048 [M+H]$^+$, m/z=1046 [M−H]$^-$.

Intermediate 20: (2',3')cyclic-[3'-O(TBDMS)-2'-O(phosphodiester)-N⁶(Bz)Adenosine]-[2'-O(TBDMS)-3'-O(phosphodiester)-Inosine]

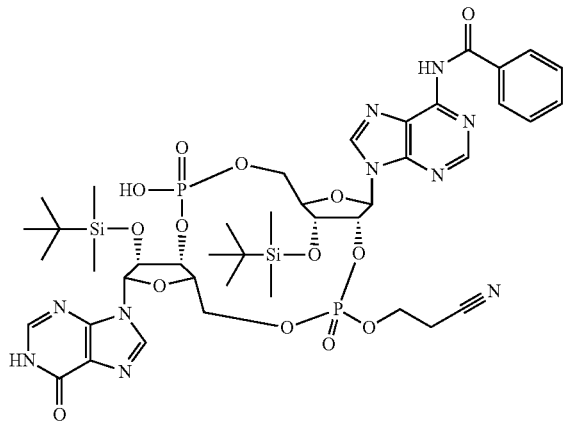 [SMILES: CC(C)(C)[Si](C)(C)O[C@@H]1C2COP(=O)(O)O[C@@H]3C(COP(=O)(OCCC#N)O[C@H]1C(n1cnc4c(NC(=O)c5ccccc5)ncnc41)O2)OC(n1cnc2c(=O)[nH]cnc21)[C@@H]3O[Si](C)(C)C(C)(C)C]

Intermediate 20 was prepared from intermediate 19 using a similar procedure to that described in Example 1.1 to provide 364 mg (89% yield) of intermediate 20. LC-MS: Rt=5.66 min, m/z=1046 [M+H]⁺, m/z=1044 [M−H]⁻.

Intermediate 21: [2'-O(TBDMS)-3'-O(CE)phosphorothioate-triester-Inosine]-(3',5')-[2'-O(TBDMS)-3'-O(H-phosphonate)-N⁶(Bz)Adenosine]

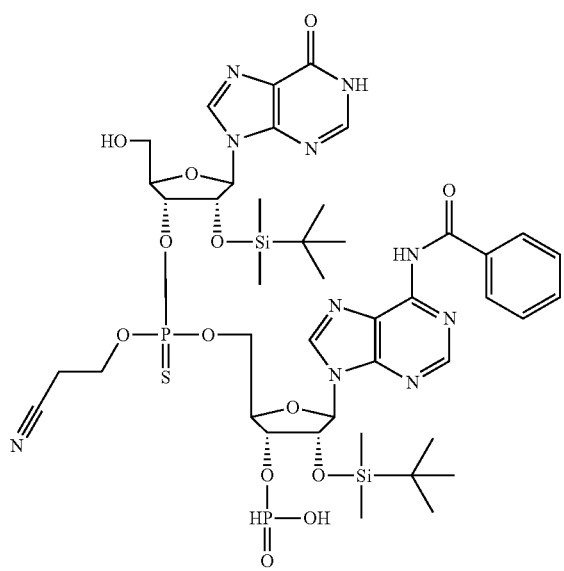

Intermediate 21 was prepared from intermediate 1 and the commercially available phosphoramidite of Inosine using a similar procedure to that described in Example 1.D to provide 1.05 g (65% yield) of intermediate 21. LC-MS: Rt=5.42 and 5.52 min, m/z=1064 [M+H]⁺, m/z=1062 [M−H]⁻.

Intermediate 22: (3',3')Cyclic-[2'-O(TBDMS)-3'-O(phosphorothioate-diester)-N⁶(Bz)Adenosine]-[2'-O(TBDMS)-3'-O(CE)phosphorothioate-triester-Inosine]

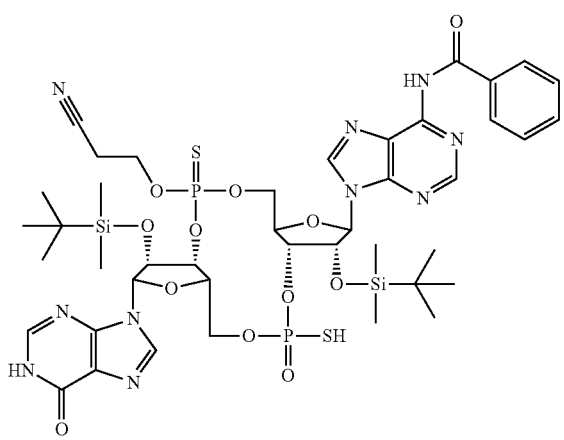 [SMILES: CC(C)(C)[Si](C)(C)O[C@H]1C(n2cnc3c(NC(=O)c4ccccc4)ncnc32)OC2COP(=S)(OCCC#N)O[C@@H]3C(COP(=O)(S)O[C@H]21)OC(n1cnc2c(=O)[nH]cnc21)[C@@H]3O[Si](C)(C)C(C)(C)C]

Intermediate 22 was prepared from intermediate 21 using a similar procedure to that described in Example 1.1 to provide 579 mg (55% yield) of intermediate 22. LC-MS: Rt=5.61 and 5.71 min, m/z=1078 [M+H]⁺, m/z=1076 [M−H]⁻.

Intermediate 23: 3'-O[(Allyl,CE)phosphotriester]-N⁶(Bz)-2'-deoxyAdenosine

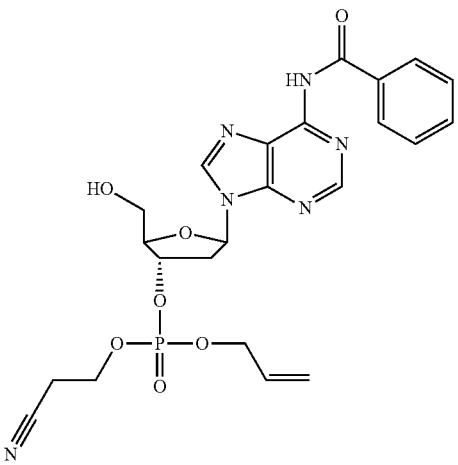 [SMILES: C=CCOP(=O)(OCCC#N)O[C@H]1CC(n2cnc3c(NC(=O)c4ccccc4)ncnc32)OC1CO]

Intermediate 23 was prepared from the commercially available phosphoramidite of 2'-deoxyadenosine using a similar procedure to that described in Example 1.A to provide 1.84 g (95% yield) of intermediate 23. LC-MS: Rt=4.31 min, m/z=529 [M+H]⁺, m/z=527 [M−H]⁻.

Intermediate 24: [3'-O(CE)phosphotriester-2'-deoxyInosine]-(3',5')-[3'-O(Allyl,CE)phosphotriester-N⁶(Bz)-2'-deoxyAdenosine]

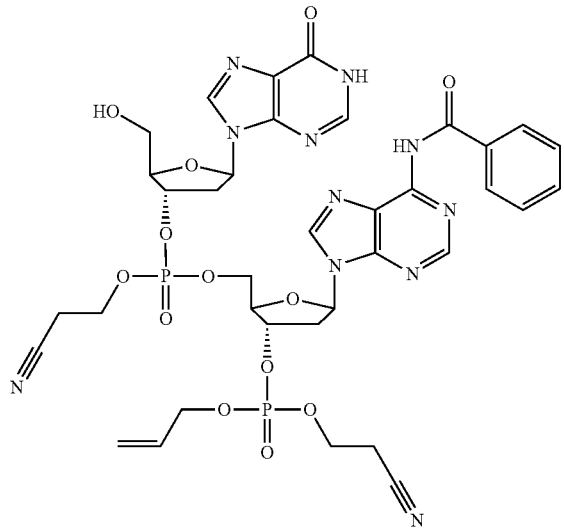 [SMILES: C=CCOP(=O)(OCCC#N)O[C@H]1CC(n2cnc3c(NC(=O)c4ccccc4)ncnc32)OC1COP(=O)(OCCC#N)O[C@H]1CC(n2cnc3c(=O)[nH]cnc32)OC1CO]

Intermediate 24 was prepared from intermediate 23 and commercially available phosphoramidite of 2'-deoxyinosine using a similar procedure to that described in Example 1.O to provide 500 mg (32% yield) of intermediate 24. Rt=5.28 min, m/z=896 [M+H]⁺, m/z=894 [M−H]⁻.

Intermediate 25: [3'-O(CE)phosphotriester-2'-deoxyInosine]-(3',5')-[3'-O(CE)phosphodiester-N⁶(Bz)-2'-deoxyAdenosine]

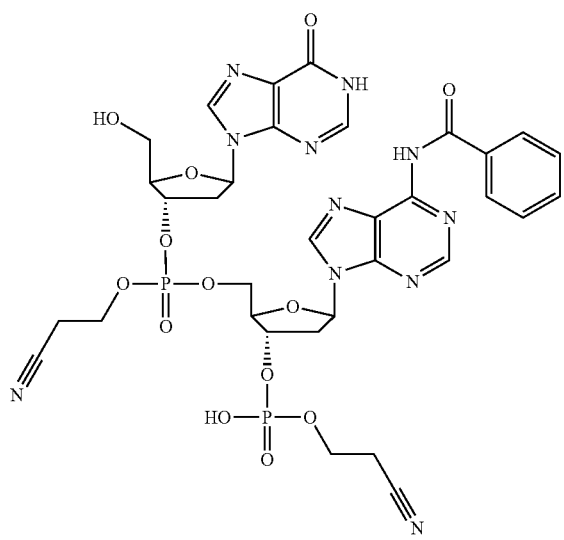 [SMILES: N#CCCOP(=O)(O)O[C@H]1CC(n2cnc3c(NC(=O)c4ccccc4)ncnc32)OC1COP(=O)(OCCC#N)O[C@H]1CC(n2cnc3c(=O)[nH]cnc32)OC1CO]

Intermediate 25 was prepared from intermediate 24 using a similar procedure to that described in Example 1.E to provide 390 mg (83% yield) of intermediate 25. LC-MS: Rt=3.35 min, m/z=856 [M+H]⁺, m/z=854 [M−H]⁻.

Intermediate 26: (3',3')Cyclic-[3'-O(CE)phosphotriester-N⁶(Bz)-2'-deoxyAdenosine]-[3'-O(CE)phosphotriester-2'-deoxyInosine]

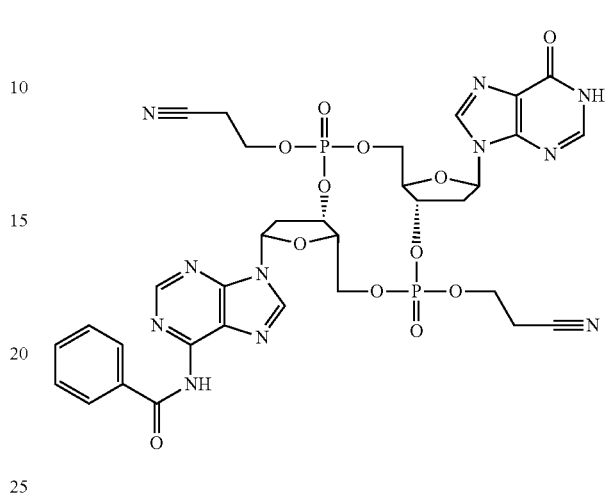

Intermediate 26 was prepared from intermediate 25 using a similar procedure to that described in Example 1.G to provide 0.38 g (99% yield) of intermediate 26. LC-MS: Rt=3.91 min, m/z=838 [M+H]⁺, m/z=836 [M−H]⁻.

Intermediate 27: [3'-O(CE)phosphotriester-2'-deoxy-2'-fluoroInosine]-(3',5')-[3'-O(Allyl,CE)phosphotriester-N⁶(Bz)-2'-deoxyAdenosine]

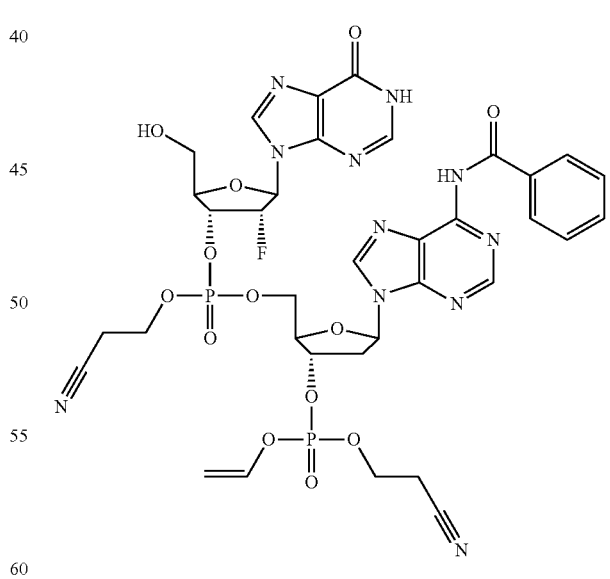

Intermediate 27 was prepared from intermediate 23 and commercially available phosphoramidite of 2'-deoxy-2'-fluoroInosine using a similar procedure to that described in Example 1.O to provide 3.16 g (62% yield) of intermediate 27. Rt=4.27 min, m/z=914 [M+H]⁺, m/z=912 [M−H]⁻.

Intermediate 28: [3'-O(CE)phosphotriester-2'-deoxy-2'-fluoroInosine]-(3',5')-[3'-O(CE)phosphodiester-N⁶(Bz)-2'-deoxyAdenosine]

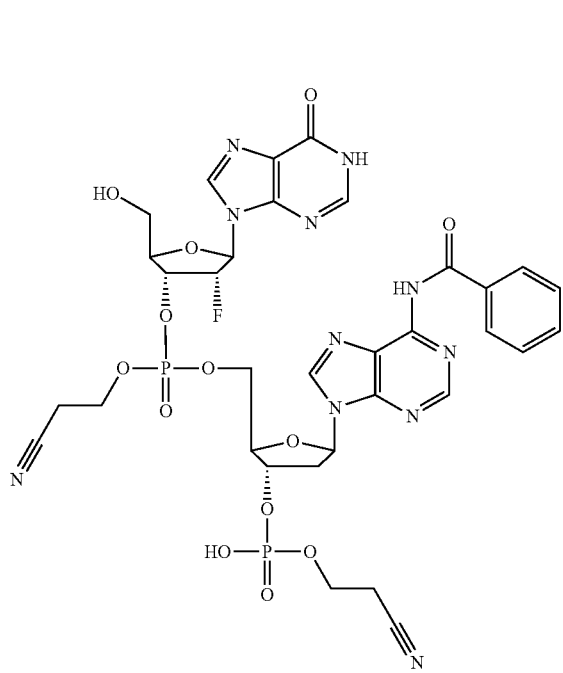 [SMILES: N#CCCOP(=O)(O)O[C@H]1CC(n2cnc3c(NC(=O)c4ccccc4)ncnc32)OC1COP(=O)(OCCC#N)O[C@@H]1C(CO)OC(n2cnc3c(=O)[nH]cnc32)[C@@H]1F]

Intermediate 28 was prepared from intermediate 27 using a similar procedure to that described in Example 1.E to provide 1.10 g (69% yield) of intermediate 28. LC-MS: Rt=3.52 min, m/z=874 [M+H]⁺, m/z=872 [M−H]⁻.

Intermediate 29: (3',3')Cyclic-[3'-O(CE)phosphotriester-N⁶(Bz)2'-deoxyAdenosine]-[3'-O(CE)phosphotriester-2'-deoxy-2'-fluoroInosine]

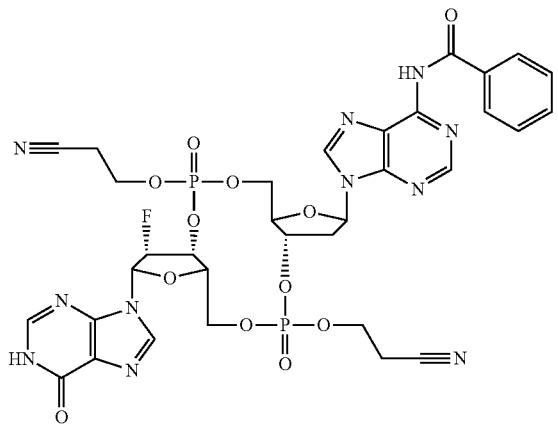 [SMILES: N#CCCOP1(=O)OCC2OC(n3cnc4c(=O)[nH]cnc43)[C@H](F)[C@@H]2OP(=O)(OCCC#N)OCC2OC(n3cnc4c(NC(=O)c5ccccc5)ncnc43)C[C@@H]2O1]

Intermediate 29 was prepared from intermediate 28 using a similar procedure to that described in Example 1.H to provide 1.01 g (99% yield) of intermediate 29. LC-MS: Rt=4.23 and 4.07 min, m/z=856 [M+H]⁺, m/z=854 [M−H]⁻.

Intermediate 30: 3'-O(Allyl,CE)phosphotriester-N⁶(Bz)-2'-deoxy-2'-fluoroAdenosine

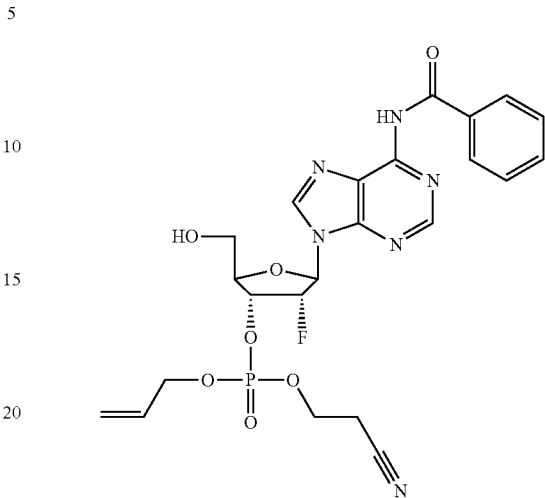

Intermediate 30 was prepared from the commercially available phosphoramidite of 2'-deoxy-2'-fluoroAdenosine using a similar procedure to that described in Example 1.A to provide 2.68 g (85% yield) of intermediate 30. LC-MS: Rt=4.50 min, m/z=547 [M+H]⁺, m/z=545 [M−H]⁻.

Intermediate 31: [3'-O(CE)phosphotriester-2'-deoxy-2'-fluoroInosine]-(3',5')-[3'-O(Allyl,CE)phosphotriester-N⁶(Bz)-2'-deoxy-2'-fluoroAdenosine]

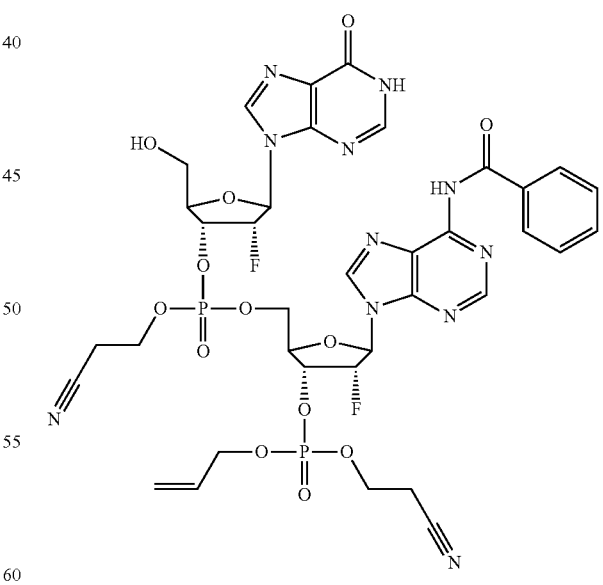

Intermediate 31 was prepared from intermediate 30 and commercial phosphoramidite of 2'-deoxy-2'-fluoroInosine using a similar procedure to that described in Example 1.0 to provide 2.53 g (55% yield) of intermediate 31. Rt=4.39 min, m/z=932 [M+H]⁺, m/z=930 [M−H]⁻.

Intermediate 32: [3'-O(CE)phosphotriester-2'-deoxy-2'-fluoroInosine]-(3',5')-[3'-O-(CE)phosphodiester-N⁶(Bz)-2'-deoxy-2'-fluoroAdenosine]

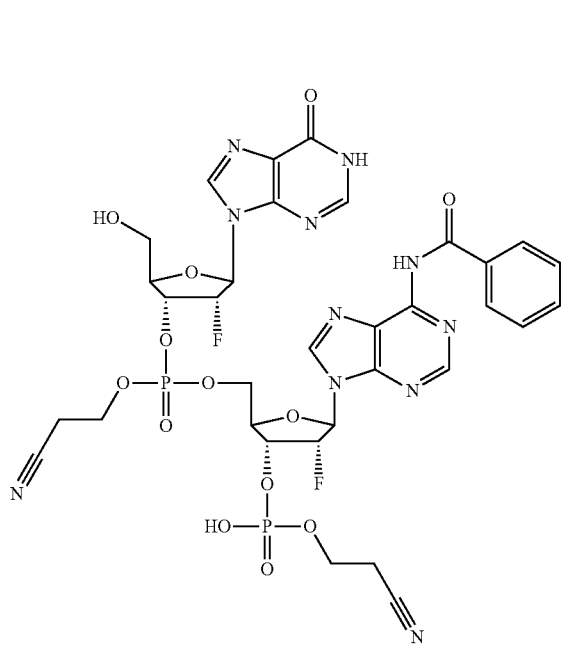 [SMILES: N#CCCOP(=O)(O)O[C@@H]1C(COP(=O)(OCCC#N)O[C@@H]2C(CO)OC(n3cnc4c(=O)[nH]cnc43)[C@@H]2F)OC(n2cnc3c(NC(=O)c4ccccc4)ncnc32)[C@@H]1F]

Intermediate 32 was prepared from intermediate 31 using a similar procedure to that described in Example 1.E to provide 4.4 g (92% yield) of intermediate 32. LC-MS: Rt=3.58 and 3.59 min, m/z=892 [M+H]⁺, m/z=891 [M−H]⁻.

Intermediate 33: (3',3')Cyclic-[3'-O(CE)phosphotriester-N⁶(Bz)2'-deoxy-2'-fluoroAdenosine]-[3'-O-(CE)phosphotriester-2'-deoxy-2'-fluoroInosine]

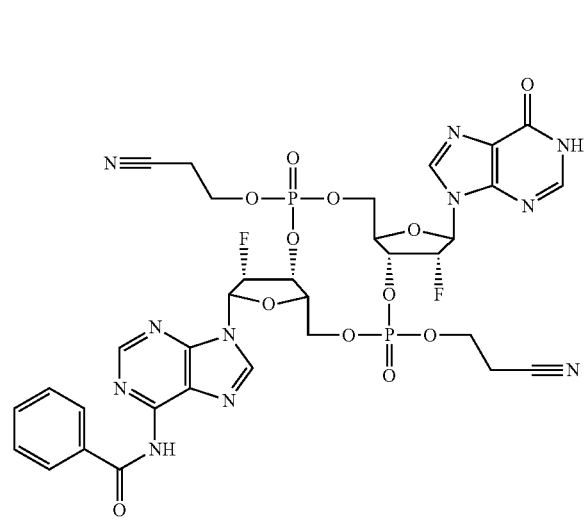 [SMILES: N#CCCOP1(=O)OCC2OC(n3cnc4c(=O)[nH]cnc43)[C@H](F)[C@@H]2OP(=O)(OCCC#N)OCC2OC(n3cnc4c(NC(=O)c5ccccc5)ncnc43)[C@H](F)[C@@H]2O1]

Intermediate 33 was prepared from intermediate 32 using a similar procedure to that described in Example 1.G to provide 1.40 g (99% yield) of intermediate 33. LC-MS: Rt=4.21 and 4.42 min, m/z=874 [M+H]⁺, m/z=872 [M−H]⁻.

Intermediate 34: 3'-O(Allyl,CE)phosphorothioate-triester-N⁶(Bz)-2'-deoxy-2'-fluoroAdenosine

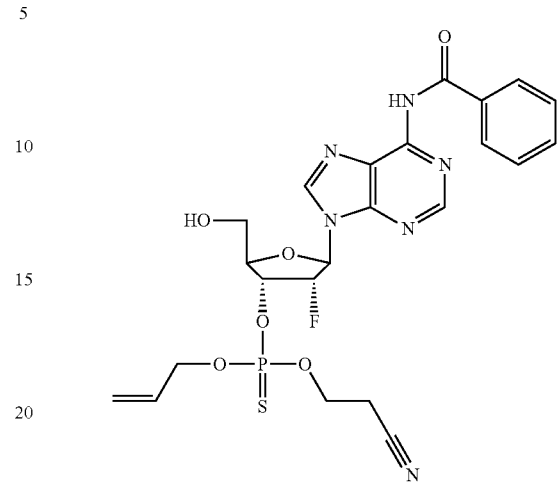

Intermediate 34 was prepared from the commercially available phosphoramidite of 2'-deoxy-2'-fluoroAdenosine using a similar procedure to that described in Example 1.A to provide 647 mg (55% yield) of intermediate 34. LC-MS: Rt=5.06 min, m/z=563 [M+H]⁺, m/z=561 [M−H]⁻.

Intermediate 35: [3'-O(CE)phosphorothioate-triester-2'-deoxy-2'-fluoroInosine]-(3',5')-[3'-O(Allyl,CE)phosphorothioate-triester-N⁶(Bz)-2'-deoxy-2'-fluoroAdenosine]

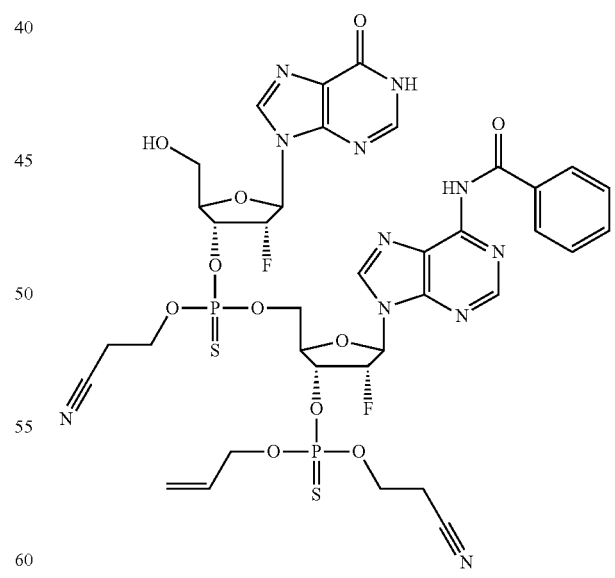

Intermediate 35 was prepared from intermediate 34 and commercially available phosphoramidite of 2'-deoxy-2'-fluoroInosine using a similar procedure to that described in Example 1.0 to provide 447 mg (35% yield) of intermediate 35. Rt=6.20 min, m/z=964 [M+H]⁺, m/z=962 [M−H]⁻.

Intermediate 36: [3'-O(CE)phosphorothioate-triester-2'-deoxy-2'-fluoroInosine]-(3',5')-[3'-O-(CE)phosphorothioate-diester-$N^6$(Bz)-2'-deoxy-2'-fluoro-Adenosine]

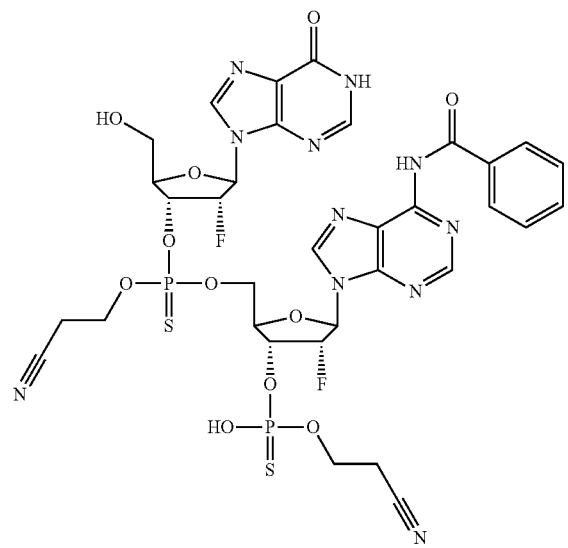 [SMILES: N#CCCOP(O)(=S)O[C@@H]1C(COP(=S)(OCCC#N)O[C@@H]2C(CO)OC(n3cnc4c(=O)[nH]cnc43)[C@@H]2F)OC(n2cnc3c(NC(=O)c4ccccc4)ncnc32)[C@@H]1F]

Intermediate 36 was prepared from intermediate 35 using a similar procedure to that described in Example 1.E to provide 232 mg (43% yield) of intermediate 36. LC-MS: Rt=4.25 and 4.55 min, m/z=924 [M+H]$^+$, m/z=922 [M−H]$^−$.

Intermediate 37: (3',3')Cyclic-[3'-O(CE)phosphorothioate-triester-$N^6$(Bz)2'-deoxy-2'-fluoroAdenosine]-[3'-O-(CE)phosphorothioate-triester-2'-deoxy-2'-fluoroInosine]

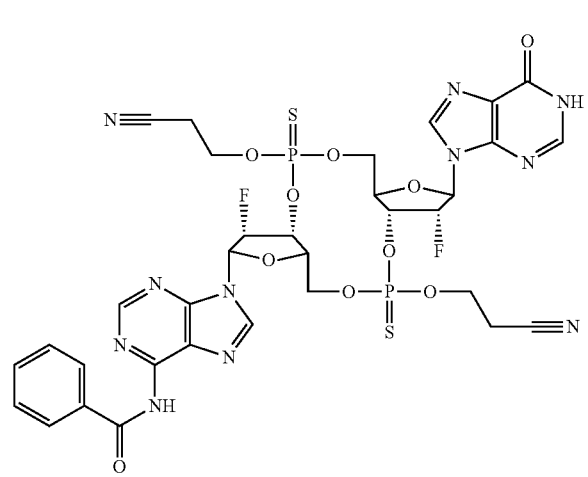 [SMILES: N#CCCOP1(=S)OCC2OC(n3cnc4c(=O)[nH]cnc43)[C@H](F)[C@@H]2OP(=S)(OCCC#N)OCC2OC(n3cnc4c(NC(=O)c5ccccc5)ncnc43)[C@H](F)[C@@H]2O1]

Intermediate 37 was prepared from intermediate 36 using a similar procedure to that described in Example 1.G to provide 35 mg (36% yield) of intermediate 37. LC-MS: Rt=5.00 and 5.32 min, m/z=906 [M+H]$^+$, m/z=904 [M−H]$^−$.

Intermediate 38: 2'-O—(H-phosphonate)-3'-O-TBDMS-$N^6$(Bz)-Adenosine

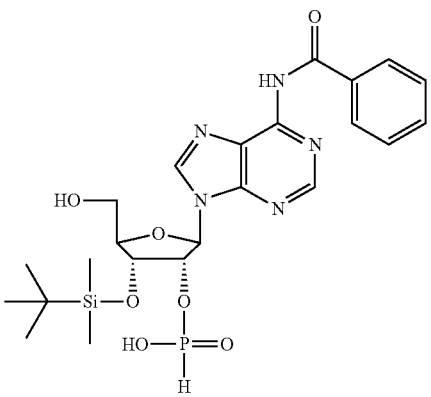 [SMILES: CC(C)(C)[Si](C)(C)O[C@@H]1C(CO)OC(n2cnc3c(NC(=O)c4ccccc4)ncnc32)[C@@H]1O[PH](=O)O]

Intermediate 38 was prepared from the commercially available 2'-phosphoramidite of Adenosine using a similar procedure to that described in Example 1.B to provide 1.81 g (95% yield) of intermediate 38. LC-MS: Rt=4.53 min, m/z=550 [M+H]$^+$, m/z=548 [M−H]$^−$.

Intermediate 39: [3'-O-(CE)phosphotriester-2'-deoxy-2'-fluoroInosine]-(3',5')-[2'-O-(H-phosphonate)-3'-O-TBDMS-$N^6$(Bz)-Adenosine]

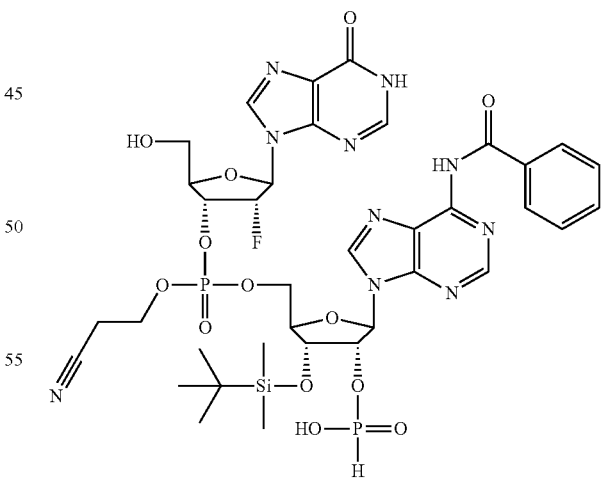

Intermediate 39 was prepared from intermediate 38 and commercially available phosphoramidite of 2'-deoxy-2'-fluoroInosine using a similar procedure to that described in Example 1.D to provide 340 mg (55% yield) of intermediate 39. Rt=4.28 min, m/z=935 [M+H]$^+$, m/z=933 [M−H]$^−$.

Intermediate 40: Cyclic-(2',3')-[2'-O-(CE)phosphotriester-3'-O-TBDMS-N⁶(Bz)Adenosine]-[3'-O-(CE)phosphotriester-2'-deoxy-2'-fluoroInosine]

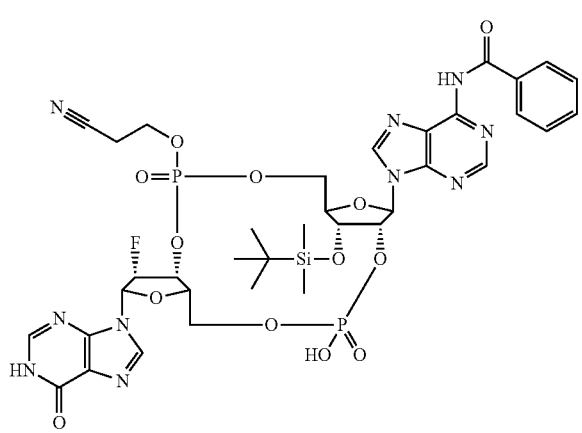 [SMILES: CC(C)(C)[Si](C)(C)O[C@@H]1C2COP(=O)(OCCC#N)O[C@@H]3C(COP(=O)(O)O[C@H]1C(n1cnc4c(NC(=O)c5ccccc5)ncnc41)O2)OC(n1cnc2c(=O)[nH]cnc21)[C@@H]3F]

Intermediate 40 was prepared from intermediate 39 using a similar procedure to that described in Example 1.1 to provide 340 mg (95% yield) of intermediate 40. LC-MS: Rt=4.44 min, m/z=933 [M+H]$^+$, m/z=931 [M−H]$^-$.

Intermediate 41: 3'-O-(Allyl,CE)phosphotriester-2'-deoxy-2'-fluoroInosine

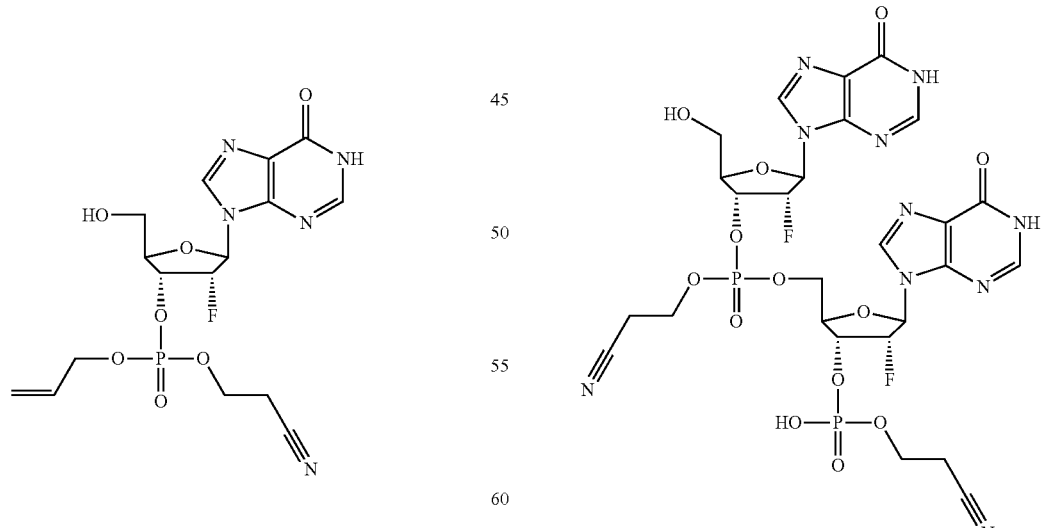

Intermediate 41 was prepared from the commercially available phosphoramidite of 2'-deoxy-2'-fluoroInosine using a similar procedure to that described in Example 1.A to provide 600 mg (98% yield) of intermediate 41. LC-MS: Rt=3.78 min, m/z=444 [M+H]$^+$, m/z=442 [M−H]$^-$.

Intermediate 42: [3'-O-(CE)phosphotriester-2'-deoxy-2'fluoroInosine]-(3',5')-[3'-O-(Allyl,CE)phosphotriester-2'-deoxy-2'-fluoroInosine]

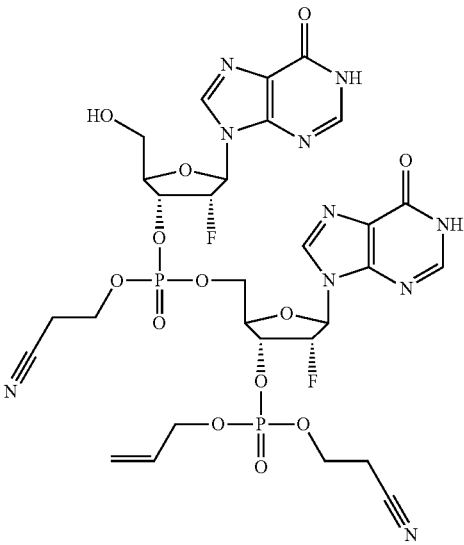 [SMILES: C=CCOP(=O)(OCCC#N)O[C@@H]1C(COP(=O)(OCCC#N)O[C@@H]2C(CO)OC(n3cnc4c(=O)[nH]cnc43)[C@@H]2F)OC(n2cnc3c(=O)[nH]cnc32)[C@@H]1F]

Intermediate 42 was prepared from intermediate 41 and commercially available phosphoramidite of 2'-deoxy-2'-fluoroInosine using a similar procedure to that described in Example 1.0 to provide 610 mg (55% yield) of intermediate 42. Rt=5.50 min, m/z=829 [M+H]$^+$, m/z=827 [M−H]$^-$.

Intermediate 43: [3'-O-(CE)phosphotriester-2'-deoxy-2'fluoroInosine]-(3',5')-[3'-O-(CE)phosphodiester-2'-deoxy-2'-fluoroInosine]

Intermediate 43 was prepared from intermediate 42 using a similar procedure to that described in Example 1.F to provide 580 mg (90% yield) of intermediate 43. LC-MS: Rt=3.40 min, m/z=789 [M+H]$^+$, m/z=787 [M−H]$^-$.

Intermediate 44: Cyclic-(3',3')-[3'-O-(CE)phosphotriester-2'-deoxy-2'-fluoroInosine]-[3'-O-(CE)phosphotriester-2'-deoxy-2'-fluoroInosine]

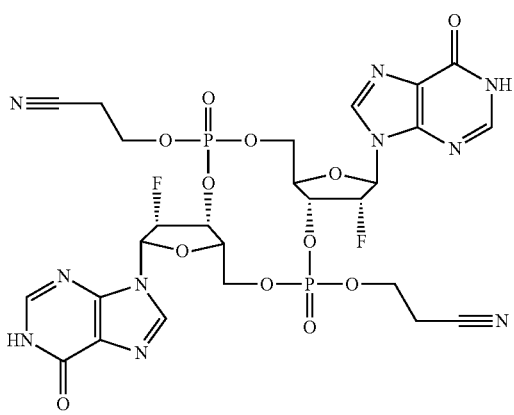 [SMILES: N#CCCOP1(=O)OCC2OC(n3cnc4c(=O)[nH]cnc43)[C@H](F)[C@@H]2OP(=O)(OCCC#N)OCC2OC(n3cnc4c(=O)[nH]cnc43)[C@H](F)[C@@H]2O1]

Intermediate 44 was prepared from intermediate 43 using a similar procedure to that described in Example 1.H to provide 500 mg (99% yield) of intermediate 44. LC-MS: Rt=3.86 min, m/z=771 [M+H]$^+$, m/z=769 [M−H]$^−$.

Intermediate 45: 3'-O-(Allyl,CE)phosphotriester-N$^2$(iB)-2'-deoxy-2'-fluoroGuanosine

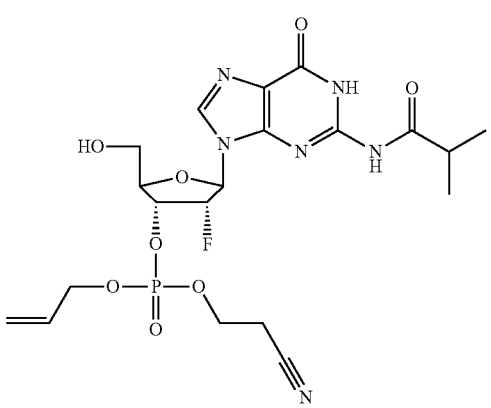 [SMILES: C=CCOP(=O)(OCCC#N)O[C@@H]1C(CO)OC(n2cnc3c(=O)[nH]c(NC(=O)C(C)C)nc32)[C@@H]1F]

Intermediate 45 was prepared from the commercially available phosphoramidite of 2'-deoxy-2'-fluoroGuanosine using a similar procedure to that described in Example 1.A to provide 3.75 g (60% yield) of intermediate 45. LC-MS: Rt=4.25 min, m/z=529 [M+H]$^+$, m/z=527 [M−H]$^−$.

Intermediate 46: [3'-O-(CE)phosphotriester-N$^2$(iB)-2'-deoxy-2'fluoroGuanosine]-(3',5')-[3'-O-(Allyl,CE) phosphotriester-N$^2$(iB)-2'-deoxy-2'-fluoroGuanosine]

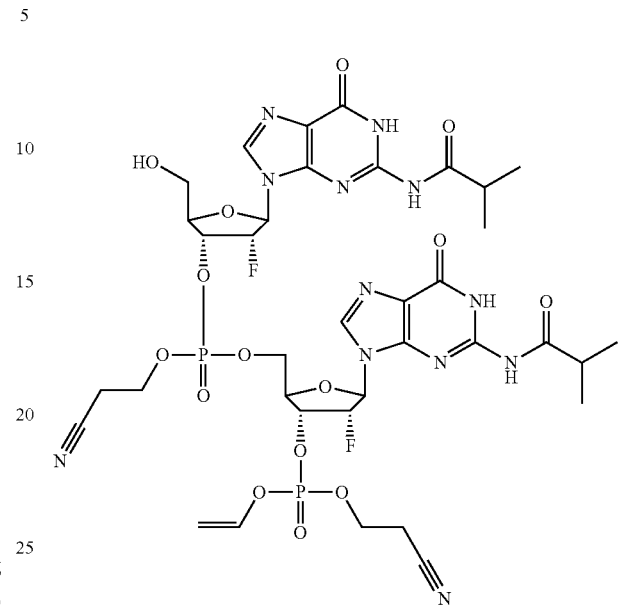

Intermediate 46 was prepared from intermediate 45 and commercially available phosphoramidite of 2'-deoxy-2'-fluoroGuanosine using a similar procedure to that described in Example 1.O to provide 1.07 g (67% yield) of intermediate 46. Rt=4.80 min, m/z=999 [M+H]$^+$, m/z=997 [M−H]$^−$.

Intermediate 47: [3'-O-(CE)phosphotriester-N$^2$(iB)-2'-deoxy-2'fluoroGuanosine]-(3',5')-[3'-O-(CE)phosphodiester-N$^2$(iB)-2'-deoxy-2'-fluoroGuanosine]

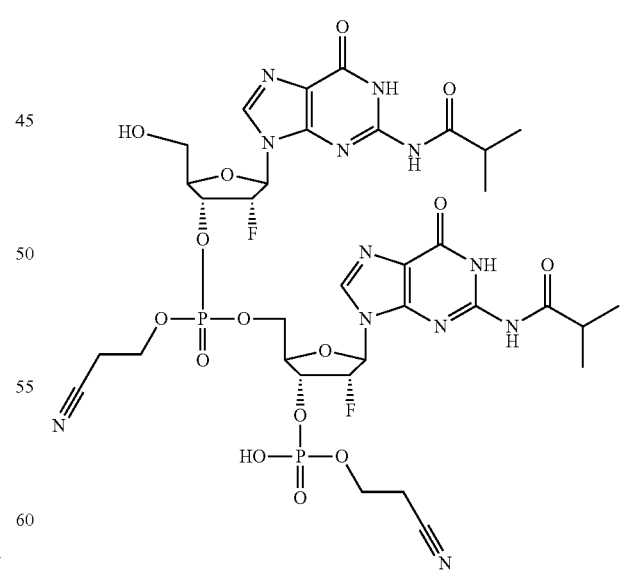

Intermediate 47 was prepared from intermediate 46 using a similar procedure to that described in Example 1.F to provide 610 mg (99% yield) of intermediate 47. LC-MS: Rt=4.05 min, m/z=959 [M+H]$^+$, m/z=957 [M−H]$^−$.

Intermediate 48: Cyclic-(3',3')-[3'-O-(CE)phosphotriester-N²(iB)-2'-deoxy-2'-fluoroGuanosine]-[3'-O-(CE)phosphotriester-N²(iB)-2'-deoxy-2'-fluoroGuanosine]

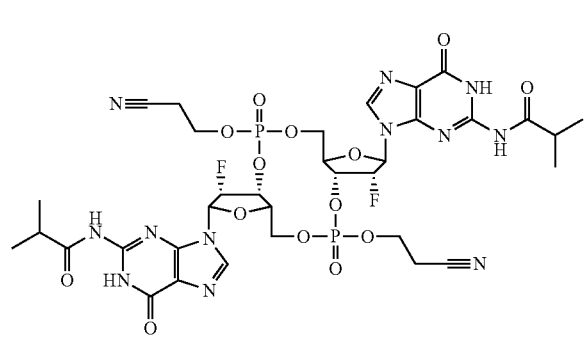 [SMILES: CC(C)C(=O)Nc1nc2c(ncn2C2OC3COP(=O)(OCCC#N)O[C@@H]4C(COP(=O)(OCCC#N)O[C@H]3[C@H]2F)OC(n2cnc3c(=O)[nH]c(NC(=O)C(C)C)nc32)[C@@H]4F)c(=O)[nH]1]

Intermediate 48 was prepared from intermediate 47 using a similar procedure to that described in Example 1.H to provide 580 mg (96% yield) of intermediate 48. LC-MS: Rt=4.77 min, m/z=941 [M+H]⁺, m/z=939 [M−H]⁻.

Intermediate 49: [3'-O-(CE)phosphotriester-N⁶(Bz) 2'-deoxy-2'fluoroAdenosine]-(3',5')-[3'-O-(Allyl, CE)phosphotriester-N²(iB)-2'-deoxy-2'-fluoroGuanosine]

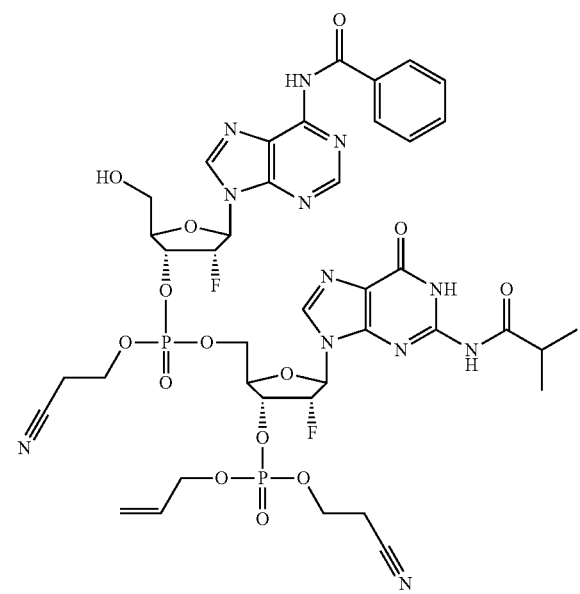 [SMILES: C=CCOP(=O)(OCCC#N)O[C@@H]1C(COP(=O)(OCCC#N)O[C@@H]2C(CO)OC(n3cnc4c(NC(=O)c5ccccc5)ncnc43)[C@@H]2F)OC(n2cnc3c(=O)[nH]c(NC(=O)C(C)C)nc32)[C@@H]1F]

Intermediate 49 was prepared from intermediate 45 and commercially available phosphoramidite of 2'-deoxy-2'-fluoroAdenosine using a similar procedure to that described in Example 1.O to provide 4.96 g (68% yield) of intermediate 49. Rt=4.98 min, m/z=1017 [M+H]⁺, m/z=1015 [M−H]⁻.

Intermediate 50: [3'-O-(CE)phosphotriester-N⁶(Bz) 2'-deoxy-2'fluoroAdenosine]-(3',5')-[3'-O-(CE)phosphodiester-N²(iB)-2'-deoxy-2'-fluoroGuanosine]

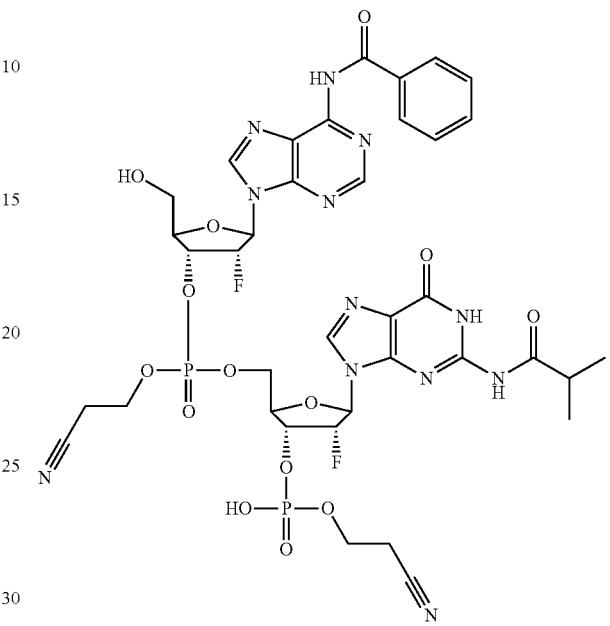

Intermediate 50 was prepared from intermediate 47 using a similar procedure to that described in Example 1.E to provide 4.4 g (92% yield) of intermediate 50. LC-MS: Rt=4.36 min, m/z=977 [M+H]⁺, m/z=975 [M−H]⁻.

Intermediate 51: Cyclic-(3',3')-[3'-O-(CE)phosphotriester-N⁶(Bz)2'-deoxy-2'fluoroAdenosine]-[3'-O-(CE)phosphotriester-N²(iB)-2'-deoxy-2'-fluoroGuanosine]

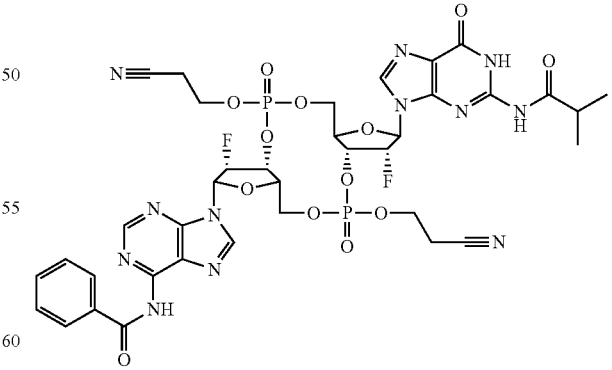

Intermediate 51 was prepared from intermediate 50 using a similar procedure to that described in Example 1.G to provide 4.30 g (99% yield) of intermediate 51. LC-MS: Rt=5.72 min, m/z=838 [M+H]⁺, m/z=836 [M−H]⁻.

Intermediate 52: 3'-O-(Allyl,CE)phosphorothioate-triester-N²(iB)-2'-deoxy-2'-fluoroGuanosine

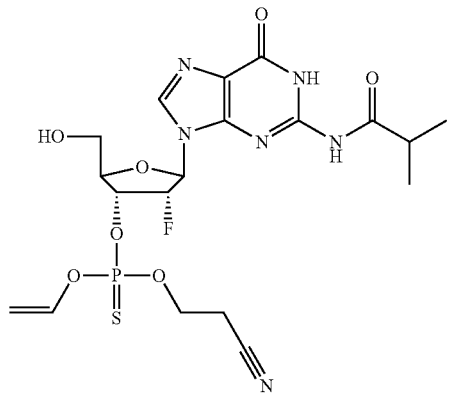 [SMILES: C=COP(=S)(OCCC#N)O[C@@H]1C(CO)OC(n2cnc3c(=O)[nH]c(NC(=O)C(C)C)nc32)[C@@H]1F]

Intermediate 52 was prepared from the commercially available phosphoramidite of 2'-deoxy-2'-fluoroGuanosine using a similar procedure to that described in Example 1.A to provide 632 mg (50% yield) of intermediate 52. LC-MS: Rt=5.86 min, m/z=545 [M+H]$^+$, m/z=543 [M−H]$^-$.

Intermediate 53: [3'-O-(CE)phosphorothioate-triester-N⁶(Bz)2'-deoxy-2'fluoroAdenosine]-(3',5')-[3'-O-(Allyl,CE)phosphorothioate-triester-N²(iB)-2'-deoxy-2'-fluoroGuanosine]

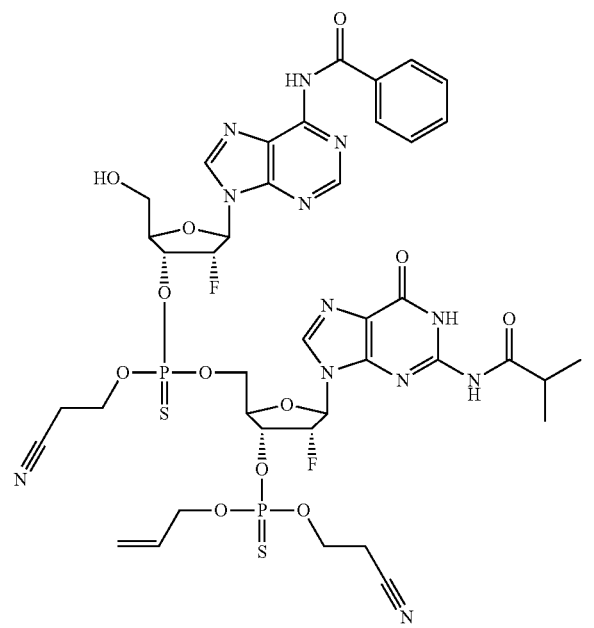 [SMILES: C=CCOP(=S)(OCCC#N)O[C@@H]1C(COP(=S)(OCCC#N)O[C@@H]2C(CO)OC(n3cnc4c(NC(=O)c5ccccc5)ncnc43)[C@@H]2F)OC(n2cnc3c(=O)[nH]c(NC(=O)C(C)C)nc32)[C@@H]1F]

Intermediate 53 was prepared from intermediate 52 and commercially available phosphoramidite of 2'-deoxy-2'-fluoroAdenosine using a similar procedure to that described in Example 1.O to provide 310 mg (25% yield) of intermediate 53. Rt=6.60 min, m/z=1049 [M+H]$^+$, m/z=1047 [M−H]$^-$.

Intermediate 54: [3'-O-(CE)phosphorothioate-triester-N⁶(Bz)2'-deoxy-2'fluoroAdenosine]-(3',5')-[3'-O-(CE)phosphorothioate-diester-N²(iB)-2'-deoxy-2'-fluoroGuanosine]

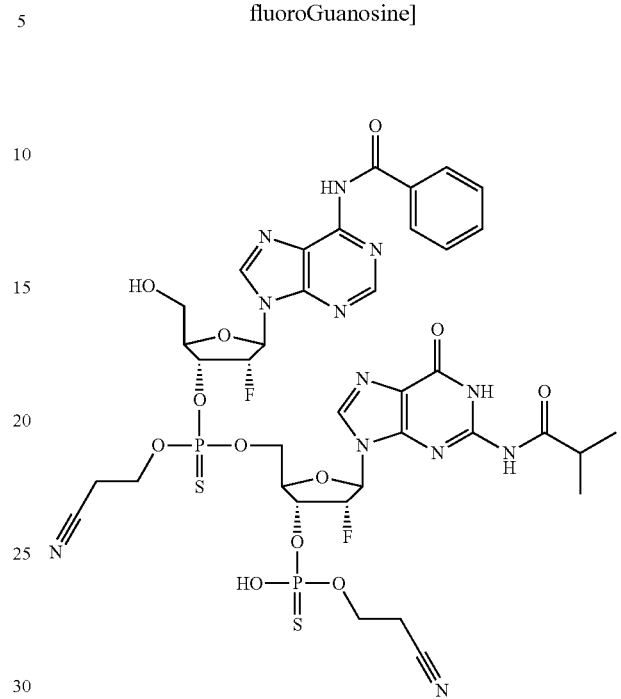

Intermediate 54 was prepared from intermediate 53 using a similar procedure to that described in Example 1.E to provide 100 mg (33% yield) of intermediate 54. LC-MS: Rt=4.58 and 4.70 min, m/z=1009 [M+H]$^+$, m/z=1007 [M−H]$^-$.

Intermediate 55: Cyclic-(3',3')-[3'-O-(CE)phosphorothioate-triester-N⁶(Bz)2'-deoxy-2'fluoroAdenosine]-[3'-O-(CE)phosphorothioate-triester-N²(iB)-2'-deoxy-2'-fluoroGuanosine]

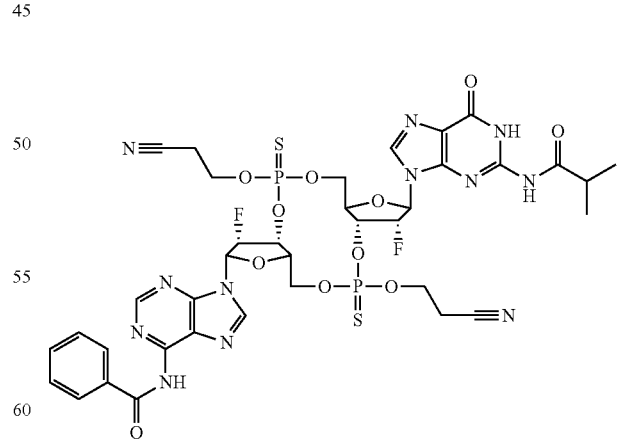

Intermediate 55 was prepared from intermediate 54 using a similar procedure to that described in Example 1.G to provide 75 mg (76% yield) of intermediate 55. LC-MS: Rt=5.32 and 5.54 min, m/z=991 [M+H]$^+$, m/z=989 [M−H]$^-$.

Intermediate 56: Iodomethyl Pivalate

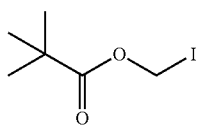

A solution of chloromethyl pivalate (1.0 g, 6.64 mmol) in dry ACN (15 mL) was treated with sodium iodide (1.9 g, 13.28 mmol). The mixture was stirred at RT overnight in the dark. Then the solvent was removed in vacuo and the residue was dissolved in DCM. The solution was washed with water, 5% NaHSO$_3$ solution and brine. The organic layer was dried over MgSO4, filtered and concentrated in vacuo to provide 1.22 g of crude intermediate 53 which was used for the next step without any further purification. $^1$H NMR (CDCl$_3$-d$_1$, 300 MHz) δ (ppm) 5.86 (s, 2H), 1.12 (s, 9H).

Example 1.1

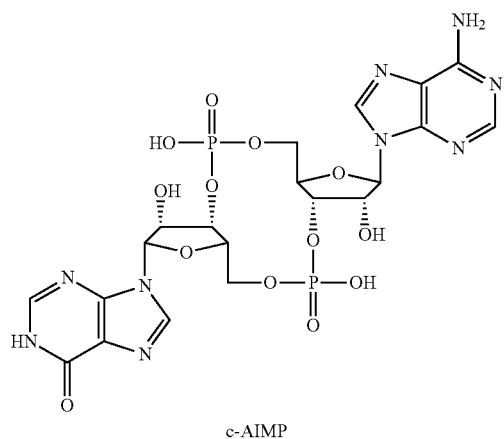 [SMILES: Nc1ncnc2c1ncn2C1OC2COP(=O)(O)O[C@@H]3C(COP(=O)(O)O[C@H]2[C@H]1O)OC(n1cnc2c(=O)[nH]cnc21)[C@@H]3O]

c-AIMP

Example 1.1 was prepared from intermediate 3 using a similar procedure to that described in Example 1.J to provide 2.4 g (60% yield) of example 1.1. LC-MS: Rt=2.72 min, m/z=660 [M+H]$^+$, m/z=658 [M−H]$^-$. $^1$H NMR (D$_2$O, 300 MHz) δ (ppm) 8.34 (s, 1H), 8.27 (s, 1H), 8.10 (s, 1H), 7.86 (s, 1H), 5.94 (s, 2H), 5.06-4.80 (m, 4H), 4.42 (m, 4H), 4.03 (m, 2H).

Example 1.2

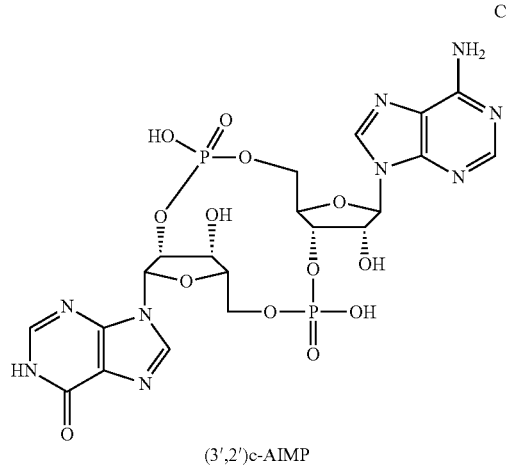

(3′,2′)c-AIMP

Example 1.2 was prepared from intermediate 13 using a similar procedure to that described in Example 1.J to provide 22.5 mg (21% yield) of example 1.2. LC-MS: Rt=2.46 min, m/z=660 [M+H]$^+$, m/z=658 [M−H]$^-$. $^1$H NMR (D$_2$O, 300 MHz) δ (ppm) 8.27 (s, 1H), 8.15 (s, 1H), 8.04 (s, 1H), 7.88 (s, 1H), 5.99 (s, 2H), 4.95 (m, 2H), 4.86 (m, 1H), 4.42 (m, 4H), 4.05 (m, 2H).

Example 1.3

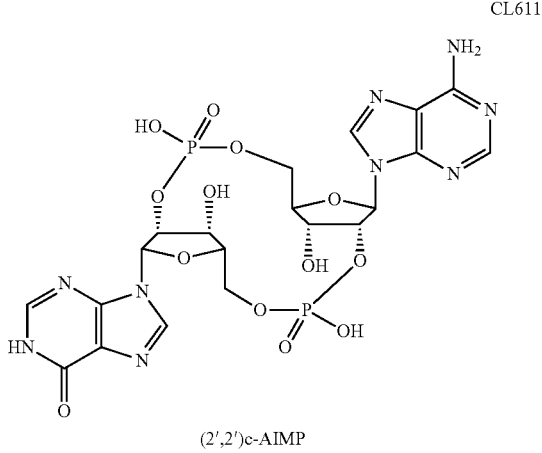 [SMILES: Nc1ncnc2c1ncn2C1OC2COP(=O)(O)O[C@H]3C(n4cnc5c(=O)[nH]cnc54)OC(COP(=O)(O)O[C@@H]1[C@@H]2O)[C@H]3O]

(2′,2′)c-AIMP

Example 1.3 was prepared from intermediate 17 using a similar procedure to that described in Example 1.J to provide 17.5 mg (22% yield) of example 1.3. LC-MS: Rt=1.35 min, m/z=660 [M+H]$^+$, m/z=658 [M−H]$^-$. $^1$H NMR (D$_2$O, 300 MHz) δ (ppm) 8.44 (s, 1H), 8.13 (s, 1H), 8.08 (s, 1H), 8.07 (s, 1H), 6.20 (d, 1H), 6.07 (d, 1H), 5.22 (m, 1H), 4.91 (m, 1H), 4.79 (m, 2H), 4.63 (m, 1H), 4.56 (m, 1H), 4.22 (m, 2H), 4.07 (m, 2H).

Example 1.4

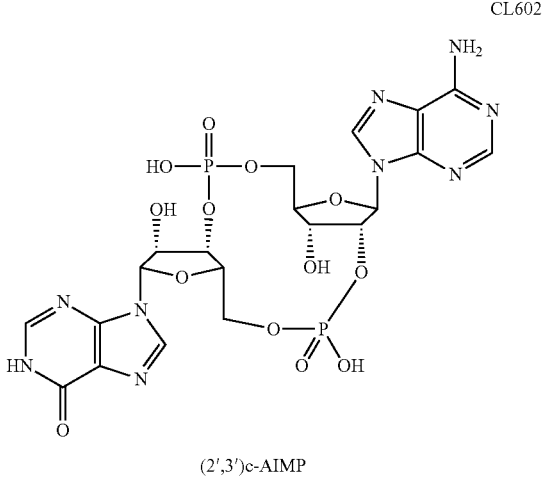 [SMILES: Nc1ncnc2c1ncn2C1OC2COP(=O)(O)O[C@@H]3C(COP(=O)(O)O[C@@H]1[C@@H]2O)OC(n1cnc2c(=O)[nH]cnc21)[C@@H]3O]

(2′,3′)c-AIMP

Example 1.4 was prepared from intermediate 20 using a similar procedure to that described in Example 1.J to provide 50 mg (19% yield) of example 1.4. LC-MS: Rt=1.53 min, m/z=660 [M+H]$^+$, m/z=658 [M−H]$^-$. $^1$H NMR (D$_2$O, 300 MHz) δ (ppm) 8.50 (s, 1H), 8.14 (s, 1H), 8.13 (s, 1H), 8.09

(s, 1H), 6.24 (d, 1H), 6.08 (s, 1H), 5.20 (m, 1H), 4.83-4.73 (m, 2H), 4.58 (d, 1H), 4.40 (m, 2H), 4.26 (m, 2H), 4.04 (m, 2H).

Example 1.5

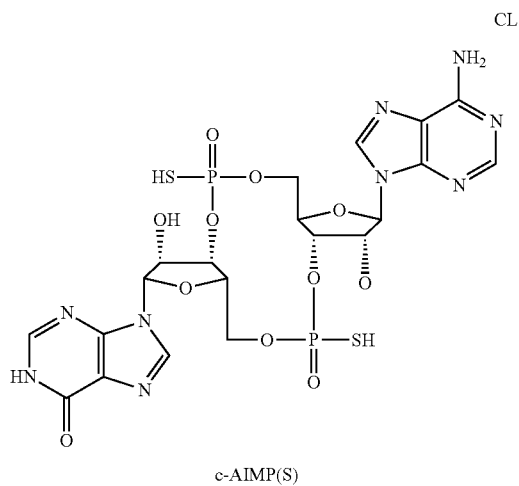

c-AIMP(S)

Example 1.5 was prepared from intermediate 22 using a similar procedure to that described in Example 1.J to provide 7 mg (20% yield) of example 1.5. LC-MS: Rt=3.45 min, m/z=692 [M+H]$^+$, m/z=690 [M−H]$^−$. $^1$H NMR (D$_2$O, 300 MHz) δ (ppm) 8.54 (s, 1H), 8.37 (s, 1H), 8.22 (s, 1H), 7.97 (s, 1H), 6.65 (dd, 1H), 6.15 (dd, 1H), 4.60-4.50 (m, 4H), 4.45 (m, 4H), 4.05 (m, 2H).

Example 1.6

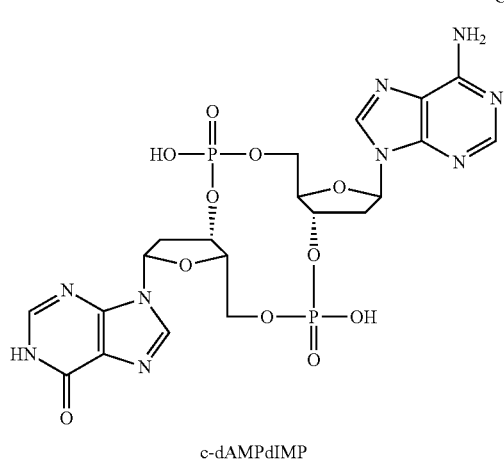

c-dAMPdIMP

Example 1.6 was prepared from intermediate 26 using a similar procedure to that described in Example 1.K to provide 90 mg (31% yield) of Example 1.6. LC-MS: Rt=2.47 min, m/z=628 [M+H]$^+$, m/z=626 [M−H]$^−$. $^1$H NMR (DMSO-d6, 300 MHz) δ (ppm) 8.37 (s, 1H), 8.32 (s, 1H), 8.13 (s, 1H), 8.05 (s, 1H), 7.26 (sl, 2H), 6.28 (m, 2H), 4.68 (m, 2H), 4.08 (m, 2H), 3.85 (m, 2H), 2.83 (m, 2H).

Example 1.7

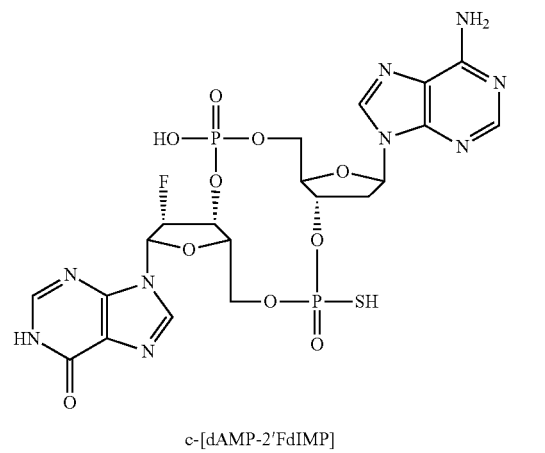

c-[dAMP-2'FdIMP]

Example 1.7 was prepared from intermediate 29 using a similar procedure to that described in Example 1.K to provide 40 mg (21% yield) of Example 1.7. LC-MS: Rt=1.97 min, m/z=646 [M+H]$^+$, m/z=644 [M−H]$^−$. $^1$H NMR (D$_2$O, 300 MHz) δ (ppm) 8.29 (s, 1H), 8.12 (s, 1H), 7.98 (s, 1H), 7.88 (s, 1H), 6.25 (m, 2H), 5.54 (m, 1H), 5.07 (m, 2H), 4.37 (m, 4H), 4.06 (m, 2H).

Example 1.8 c-(2'FdAMP)-(2'FdIMP)

Example 1.8 was prepared from intermediate 33 using a similar procedure to that described in Example 1.K to provide 104 mg (10% yield) of Example 1.8. LC-MS: Rt=2.78 min, m/z=664 [M+H]$^+$, m/z=662 [M−H]$^−$. $^1$H NMR (D$_2$O, 300 MHz) δ (ppm) 8.37 (s, 1H), 8.35 (s, 1H), 8.14 (s, 1H), 7.95 (s, 1H), 6.23 (m, 2H), 5.45 (m, 2H), 5.39 (m, 1H), 4.95 (m, 2H), 4.50 (m, 2H), 4.06 (m, 2H).

Example 1.9

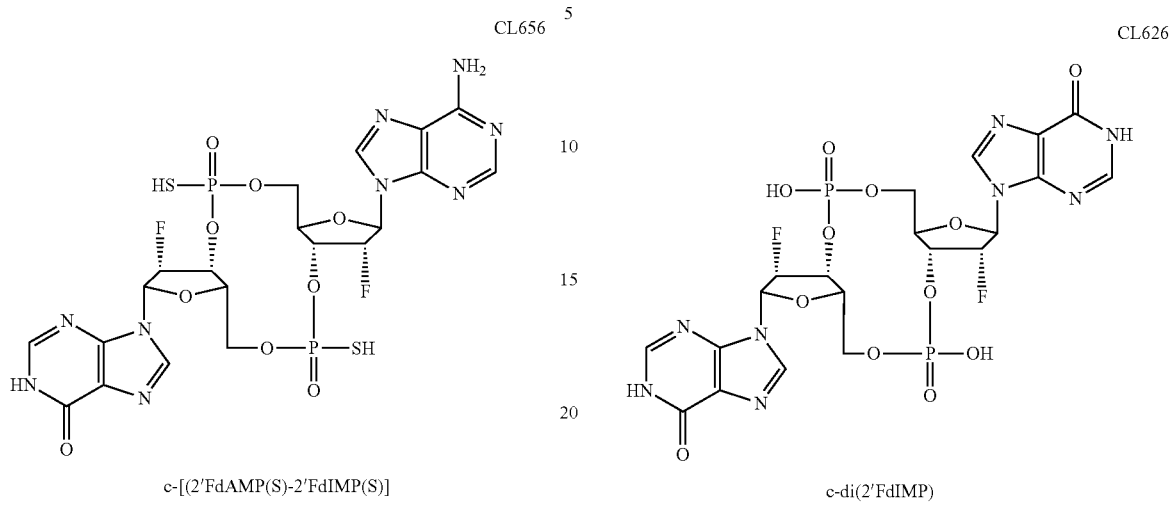

c-[(2'FdAMP(S)-2'FdIMP(S)]

Example 1.9 was prepared from intermediate 37 using a similar procedure to that described in Example 1.K to provide 10 mg (18% yield) of Example 1.9. LC-MS: Rt=3.41 min, m/z=696 [M+H]$^+$, m/z=694 [M−H]$^-$. $^1$H NMR (D$_2$O, 300 MHz) δ (ppm) 8.55 (s, 1H), 8.38 (s, 1H), 8.20 (s, 1H), 7.99 (s, 1H), 6.63 (dd, 1H), 6.15 (dd, 1H), 5.16-4.95 (m, 4H), 4.52 (m, 4H), 4.07 (m, 2H).

Example 1.10

(2',3')c-(AMP-2'FdIMP)

Example 1.10 was prepared from intermediate 40 using a similar procedure to that described in Example 1.J to provide 50 mg (19% yield) of Example 1.10. LC-MS: Rt=2.25 min, m/z=662 [M+H]$^+$, m/z=660 [M−H]$^-$. $^1$H NMR (D$_2$O, 300 MHz) δ (ppm) 8.58 (s, 1H), 8.35 (s, 1H), 8.12 (s, 1H), 7.97 (s, 1H), 6.65 (d, 1H), 6.16 (d, 1H), 4.50 (m, 2H), 5.15 (m, 2H), 4.41 (m, 4H), 4.02 (m, 1H), 3.73 (m, 1H).

Example 1.11

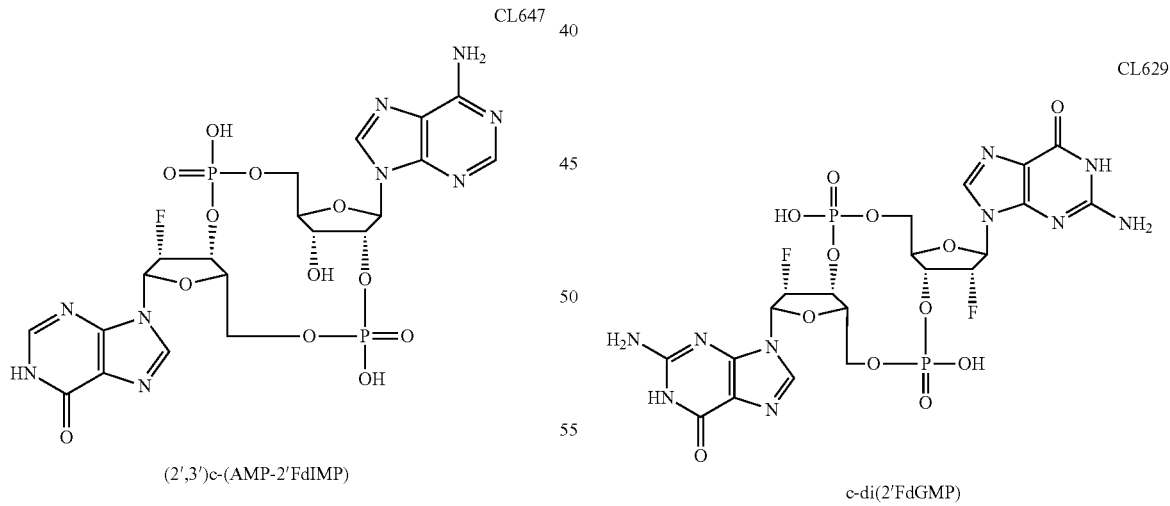

c-di(2'FdIMP)

Example 1.11 was prepared from intermediate 44 using a similar procedure to that described in Example 1.K to provide 157 mg (35% yield) of Example 1.11. LC-MS: Rt=1.48 min, m/z=665 [M+H]$^+$, m/z=663 [M−H]$^-$. $^1$H NMR (D$_2$O, 300 MHz) δ (ppm) 8.34 (s, 2H), 8.08 (s, 2H), 7.85 (s, 2H), 6.21 (m, 2H), 5.66 (m, 1H), 5.49 (m, 1H), 5.20 (m, 2H), 4.97 (m, 4H), 4.06 (m, 2H).

Example 1.12 c-di(2'FdGMP)

Example 1.12 was prepared from intermediate 48 using a similar procedure to that described in Example 1.K to provide 15 mg (5% yield) of Example 1.12. LC-MS: Rt=1.58 min, m/z=695 [M+H]$^+$, m/z=693 [M−H]$^-$. $^1$H NMR (D$_2$O, 300 MHz) δ (ppm) 8.70 (s, 2H), 6.05 (d, 2H), 5.06-4.05 (m, 8H), 4.08 (m, 2H).

Example 1.13

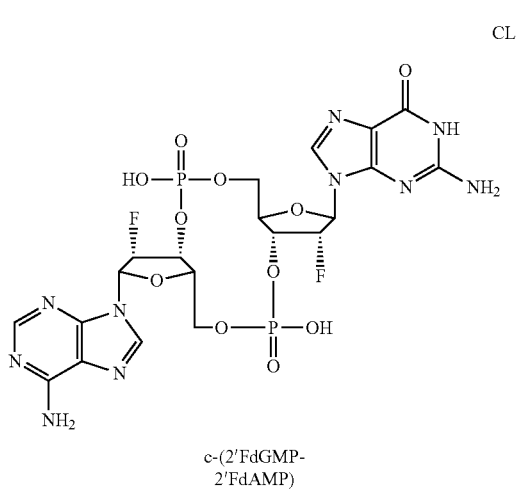

c-(2'FdGMP-2'FdAMP)

Example 1.13 was prepared from intermediate 51 using a similar procedure to that described in Example 1.K to provide 320 mg (31% yield) of Example 1.13. LC-MS: Rt=2.48 min, m/z=679 [M+H]$^+$, m/z=677 [M−H]$^-$. $^1$H NMR (D$_2$O, 300 MHz) δ (ppm) 8.17 (s, 1H), 7.83 (s, 1H), 7.63 (s, 1H), 6.09 (d, 1H), 5.94 (d, 1H), 5.62 (m, 1H), 5.50 (m, 1H), 5.15 (m, 2H), 4.42 (m, 4H), 4.03 (m, 2H).

Example 1.14

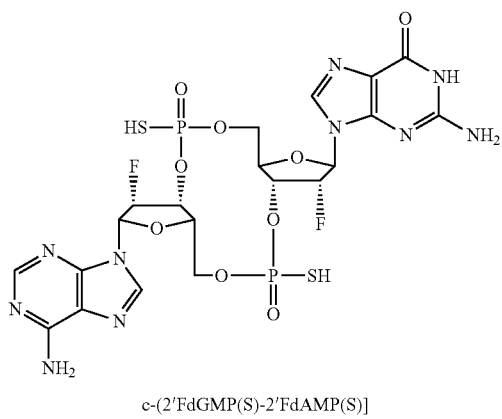

c-(2'FdGMP(S)-2'FdAMP(S)]

Example 1.14 was prepared from intermediate 55 using a similar procedure to that described in Example 1.K to provide 15 mg (28% yield) of Example 1.14. LC-MS: Rt=2.66 min, m/z=711 [M+H]$^+$, m/z=709 [M−H]$^-$. $^1$H NMR (D$_2$O, 300 MHz) δ (ppm) 8.58 (s, 1H), 8.35 (s, 1H), 7.97 (s, 1H), 6.65 (d, 1H), 6.19 (d, 1H), 4.94 (d, 1H), 4.62-4.50 (m, 4H), 4.42 (m, 4H), 4.03 (m, 2H).

Example 1.15

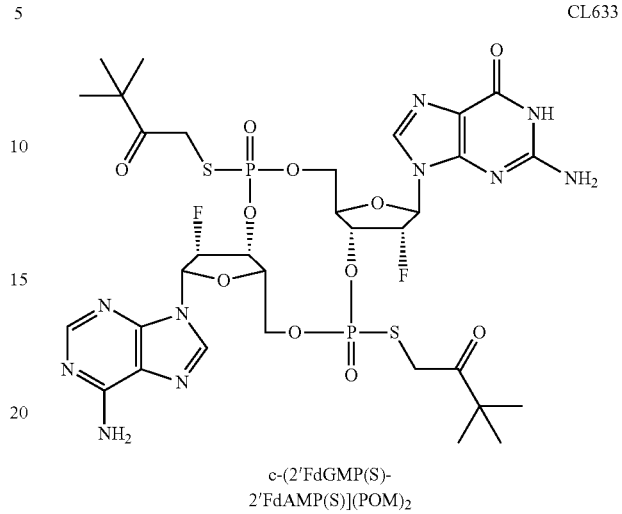

c-(2'FdGMP(S)-2'FdAMP(S)](POM)$_2$

To a solution of Example 1.14 (7 mg, 9.85 μmol) in water (200 μL) was added dropwise a solution of intermediate 56 (19 mg, 79.0 μmol) in acetone (500 μL). The mixture was stirred overnight in the dark. Then the mixture was neutralized with a saturated solution of Na$_2$S$_2$O$_3$ (15 μL) and subsequently diluted with water (10 mL). The aqueous layer was extracted three times with EtOAc (3×10 mL). The organic layers were pooled, dried over MgSO$_4$, filtered and concentrated in vacuo to provide 4 mg (45% Yield) of Example 1.15. LC-MS: Rt=4.11 min, m/z=907 [M+H]$^+$, m/z=905 [M−H]$^-$. $^1$H NMR (DMSO-d$_6$, 300 MHz) δ (ppm) 8.61 (s, 1H), 8.37 (s, 1H), 8.00 (s, 1H), 6.70 (d, 1H), 6.22 (d, 1H), 4.70-4.50 (m, 4H), 4.42 (m, 4H), 4.03 (m, 2H), 3.77 (s, 4H), 1.20 (s, 18H).

Example 1.16

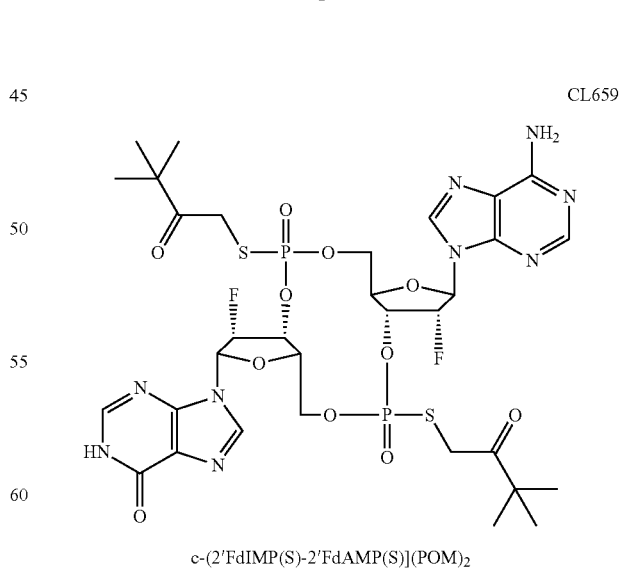

c-(2'FdIMP(S)-2'FdAMP(S)](POM)$_2$

To a solution of Example 1.9 (5 mg, 7.19 μmol) in water (200 μL) was added dropwise a solution of intermediate 56 (17 mg, 70 μmol) in acetone (500 μL). The mixture was stirred overnight in the dark. Then the mixture was neutralized with a saturated solution of $Na_2S_2O_3$ (15 μL) and subsequently diluted with water (10 mL). The aqueous layer was extracted three times with EtOAc (3×10 mL). The organic layers were pooled, dried over $MgSO_4$, filtered and concentrated in vacuo to provide 5 mg (78% Yield) of Example 1.16. LC-MS: Rt=4.55 min, m/z=892 $[M+H]^+$, m/z=890 $[M-H]^-$. $^1H$ NMR (DMSO-$d_6$, 300 MHz) δ (ppm) 8.61 (s, 1H), 8.37 (s, 1H), 8.00 (s, 1H), 6.70 (d, 1H), 6.22 (d, 1H), 4.70-4.50 (m, 4H), 4.42 (m, 4H), 4.03 (m, 2H), 3.77 (s, 4H), 1.20 (s, 18H).

Example 2: Biological Assays

We have determined that several cyclic dinucleotides of the present invention induce the production of multiple cytokines in human or animal cells. Specifically, these cyclic dinucleotides induce the production of Type I interferons and/or pro-inflammatory cytokines. The in vitro cytokine-induction activity of a representative set of these cyclic dinucleotides is reported here to require the presence of the eukaryotic cellular receptor stimulator of interferon genes (STING).

In Vitro Cytokine Induction

The cytokine-induction activities of non-fluorinated vs. fluorinated cyclic dinucleotides disclosed in this invention have been demonstrated by using different reporter cell lines. The cell lines and experiments are explained below.

Cell Lines

All the cell lines were obtained from InvivoGen. They are described here and provided with their corresponding InvivoGen catalog code.

THP1-Dual™ (InvivoGen Catalog Code: thpd-nfis):

These cells were derived from the human monocytic cell line THP-1 by stable integration of two inducible reporter constructs. They enable simultaneous study of the two main signaling pathways for STING: the NF-κB pathway, by monitoring the activity of secreted embryonic alkaline phosphatase (SEAP); and the IRF pathway, by assessing the activity of a secreted luciferase (Lucia).

Both reporter proteins are readily measurable in the cell culture supernatant when using QUANTI-Blue™ (InvivoGen catalog code: rep-qb1), a SEAP detection reagent that turns purple/blue in the presence of SEAP (quantified by measuring the optical density from 620 nm to 655 nm), and QUANTI-Luc™ (InvivoGen; catalog code: rep-qlc1), a luminometric enzyme assay that measures luciferase expression to report on ISG54 expression (as an indicator of IFN-α/β production).

Lucia ISG Cell Lines:

Each of the following two cell lines expresses a secreted luciferase (Lucia) reporter gene under control of an IRF-inducible promoter. This composite promoter comprises five IFN-stimulated response elements (ISREs) fused to a minimal promoter of the human ISG54 gene, which is unresponsive to activators of the NF-κB or AP-1 pathways. Hence, these cells enable monitoring of the IRF pathway based on luciferase (Lucia) activity. In the present invention, monitoring of the IRF pathway is used to measure the STING agonist activity of the subject cyclic dinucleotides.

1. RAW-Lucia™ ISG (InvivoGen catalog code: rawl-isg): These cells were generated from the murine RAW 264.7 macrophage cell line.
2. RAW-Lucia™ ISG-KO-STING (InvivoGen catalog code: rawl-kostg): These cells were generated from the RAW-Lucia™ ISG54 cell line (see above), through stable homozygous knockout of the STING gene.

B16 Blue™ ISG54 Cell Lines:

Each of the following two cell lines expresses a SEAP reporter gene under a promoter: the I-ISG54 reporter, which comprises the IFN-inducible ISG54 promoter enhanced by a multimeric ISRE. Stimulation of these cells with interferons, or inducers of type I interferons or of the NF-κB pathway, triggers activation of the I-ISG54 promoter (and consequently, production of SEAP) or of the IFN-β minimal promoter (and consequently, production of TNF-α). The levels of SEAP in the supernatant can be easily determined using QUANTI-Blue™ (InvivoGen catalog code: rep-qb1), a reagent that turns purple/blue in the presence of SEAP, by measuring the optical density from 620 nm to 655 nm.

1. B16-Blue™ ISG (InvivoGen catalog code: bb-ifnabg): These cells are derived from the murine B16 F1 melanoma cell line. Production of Type I interferons in these cells is measured using QUANTI-Blue™.
2. B16-Blue™ ISG-KO-STING (InvivoGen catalog code: bb-kostg): These cells were generated from the B16-Blue™ ISG cell line (see above), through stable homozygous knockout of the STING gene. Production of Type I interferons in these cells is measured using QUANTI-Blue™.

HEK-Blue™ Cell Lines:

The following three cell lines also were used for biological evaluation of the CDNs.

1. HEK-Blue™ IFN-α/β-KO-STING: These cells are derived from HEK-Blue™ IFN-α/β cells (InvivoGen catalog code: hkb-ifnab), in which the STING gene has been inactivated. HEK-Blue™ IFN-α/β cells enable detection of bioactive human type I IFNs through monitoring of activation of the ISGF3 pathway. These cells were generated by stable transfection of HEK293 cells with the human STAT2 and IRF9 genes to obtain a fully active type I IFN signaling pathway. The other genes of the pathway (IFNAR1, IFNAR2, JAK1, TyK2 and STAT1) are naturally expressed in sufficient amounts. The cells were further transfected with a SEAP reporter gene under control of an IFN-α/β-inducible ISG54 promoter. Stimulation of HEK-Blue™ IFN-α/β cells with human IFN-α or IFN-β activates the JAK/STAT/ISGF3 pathway and subsequently induces production of SEAP. Production of Type I interferons in these cells is measured using QUANTI-Blue™
2. HEK-Blue™ IL-1R (InvivoGen catalog code: hkb-il1r): HEK-Blue™ IL-1R cells were designed to detect bioactive human and murine IL-1β through monitoring of activation of the NF-κB and AP-1 pathways. Additionally, these cells detect bioactive IL-1β from cynomolgus monkeys, dogs and rats. In fact, HEK-Blue™ IL-1R cells can detect IL-1α and IL-1β, as these cytokines bind to the same receptor, IL-1R. These cells derive from HEK-Blue™ IL-1β cells (InvivoGen catalog code: hkb-il1b), in which the TNF-α response is blocked. Therefore, HEK-Blue™ IL-1R cells respond specifically to IL-1. These cells endogenously express the human IL-1 receptor and were stably transfected with the murine IL-1 receptor, rendering them very sensitive to both human and murine IL-1β. HEK-Blue™ IL-1R cells express a SEAP reporter gene under control of an IFN-1β minimal promoter fused to five NF-κB and five AP-1 binding sites. Binding of IL-1β to IL-1R on the surface of HEK-Blue™ IL-1R cells triggers a signaling cascade that leads to the activation of NF-κB and subsequent production of SEAP. Production of IL-1β in these cells is measured using QUANTI-Blue™.

3. HEK-Blue™ TNF-α (InvivoGen catalog code: hkb-tnfdmyd): HEK-Blue™ TNF-α cells enable detection of bioactive human and murine TNF-α through monitoring of activation of the NF-κB pathway. These cells were generated by stable transfection of HEK293 cells with a SEAP reporter gene under control of an IFN-1β minimal promoter fused to five NF-κB and five AP-1 binding sites. They were further rendered unresponsive to IL-1β by knocking out the MyD88 gene. Stimulation of HEK-Blue™ TNF-α cells with TNF-α triggers activation of the NF-κB-inducible promoter and production of SEAP. Production of TNF-α in these cells is measured using QUANTI-Blue™.

Quantification of IL-6 in Experiments

Interleukin-6 was quantified using an enzyme-linked immunoassay (ELISA) according to the manufacturer's instructions (R&D Systems).

In Cell Cultures

In various experiments in which different cell cultures were separately incubated with a cyclic dinucleotide, the cyclic dinucleotide induced production of Type I interferons and/or pro-inflammatory cytokines in those cells, as indirectly determined by an ISG54 (interferon-stimulated gene) reporter assay (Fensterl, White, Yamashita, & Sen, 2008). These experiments were performed as described below.

Example 2.1: Measuring Cytokine Induction in Treated Cell Cultures

Cytokine reporter cell lines used: THP1-Dual™
Cyclic dinucleotides tested: CL609, CL614, CL656, CL647, CL629, CL626, CL603, CL632 and CL633
Reference compound: c-AIMP (manufactured by InvivoGen), c-diGMP (InvivoGen catalog code: tlrl-cdg), c-diIMP (InvivoGen catalog code: tlrl-cdi) and c-GAMP (InvivoGen catalog code: tlrl-cga)
Activities evaluated: Type I IFN induction and NF-κB pathway induction.

To each well of a flat-bottom 96-well plate were added 20 μL of a solution a cyclic dinucleotide (100 μg/mL in sterile water), followed by 180 μL of a suspension of a single cell line (THP1-Dual™: ca. 100,000 cells per well). The plate was incubated for 18 h to 24 h at 37° C. in 5% $CO_2$. The level of IFN-α/β was indirectly quantified using QUANTI-Luc™, which was prepared and used according to the manufacturer's instructions. The NF-κB activity was indirectly quantified using QUANTI-Blue™, which was prepared and used according to the manufacturer's instructions.

Figure 2:
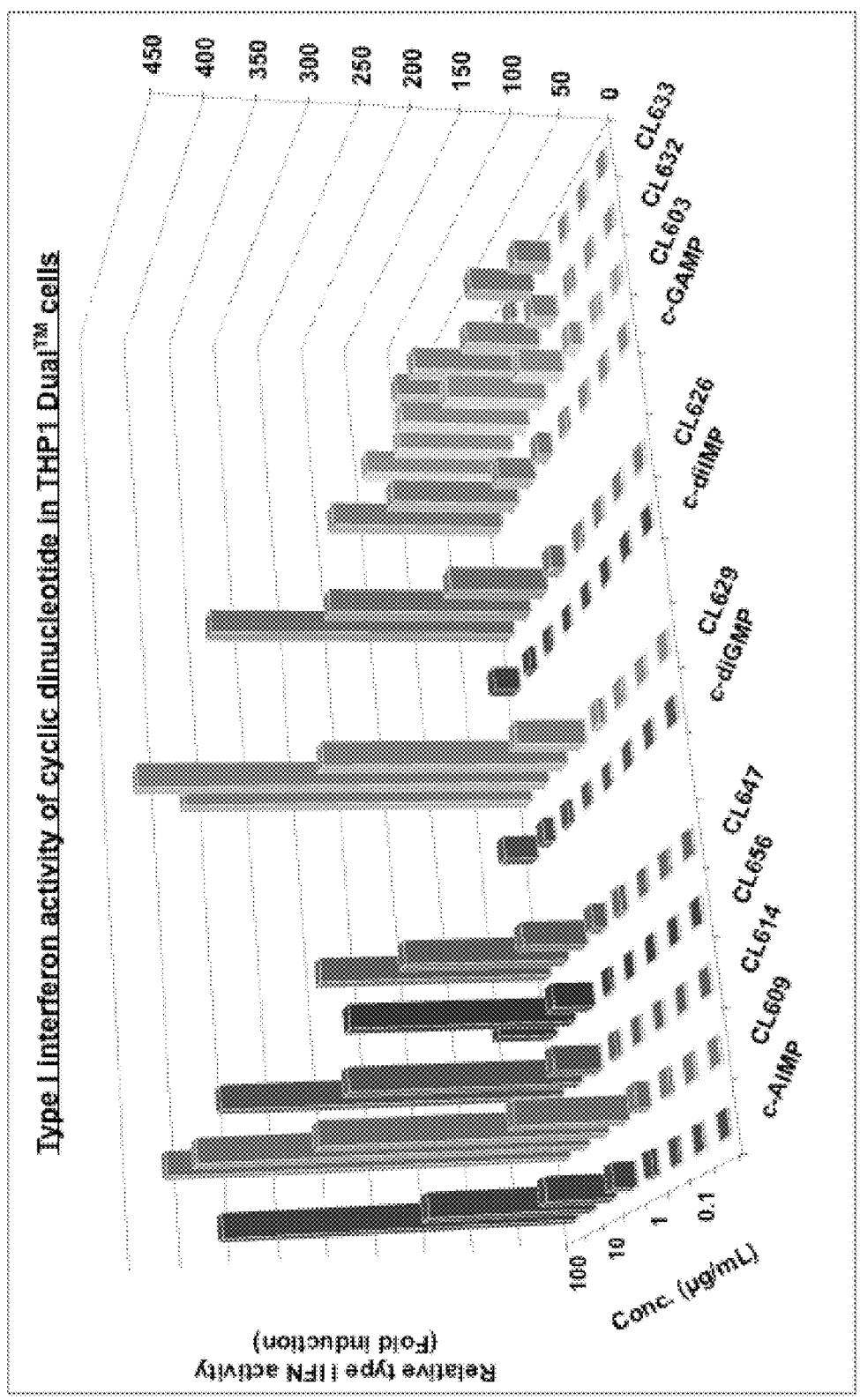
FIG. 2. In vitro Type I interferon induction activity in THP1-Dual™ cell cultures: non-fluorinated vs. fluorinated cyclic dinucleotides.
Figure 3:
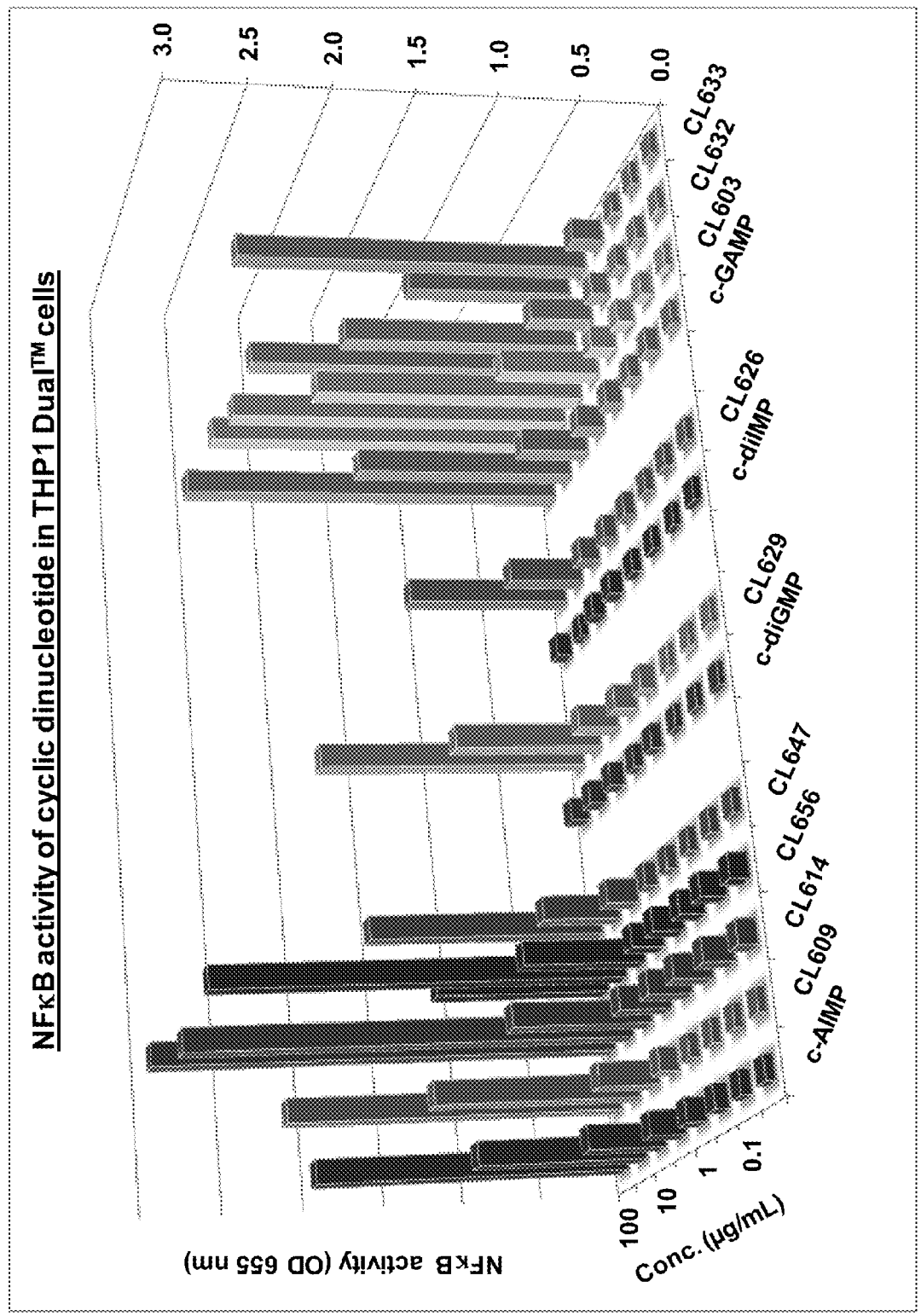
FIG. 3. In vitro NF-κB pathway induction in THP1-Dual™ cell cultures: non-fluorinated vs. fluorinated cyclic dinucleotides.

The results from this experiment are shown in FIGS. 2 and 3, which reveal three important findings: firstly, that all of the tested cyclic dinucleotides induce Type I interferons in THP1-Dual™ cells (FIG. 2); secondly, that all of them induce the NF-κB pathway in these cells (FIG. 3); and lastly, that for both of these activities the majority of the fluorinated cyclic dinucleotides are more active than are the corresponding reference compounds (c-AIMP, c-diGMP, c-diIMP and c-GAMP).

Cytokine Induction Activity is STING-Dependent

The cyclic dinucleotides disclosed in the present invention do not induce cytokine production in vitro in the supernatant of cells that lack the receptor STING.

In an experiment in which wild-type (WT) reporter cells and homozygous STING knockout (STING KO) reporter cells were each separately incubated with the cyclic dinucleotide for 18 h to 24 h, the cyclic dinucleotide induced production of Type I interferons in the WT cells but not in the STING KO cells. This finding demonstrated that STING is required for the cytokine-induction activity of the cyclic dinucleotide in vitro in cells. These experiments were performed as described below:

Example 2.2: Measuring Cytokine Induction in CDN-Treated Wild-Type or STING Knockout Cells Cytokine reporter cell lines used: B16-Blue™ ISG and RAW-Lucia™ ISG
Cyclic dinucleotides tested: CL609, CL614, CL656, CL647, CL629, CL626, CL603, CL632 and CL633
Reference compound c-AIMP (manufactured by InvivoGen), c-diGMP (InvivoGen catalog code: tlrl-cdg), c-diIMP (InvivoGen catalog code: tlrl-cdi) and c-GAMP (InvivoGen catalog code: tlrl-cga)
Cell lines used: RAW-Lucia™ ISG, RAW-Lucia™ ISG-KO-STING, B16-Blue™ ISG, and B16-Blue™ ISG-KO-STING (depending on experiment).

These Experiments were performed as described in Example 2.1.

Figure 4:
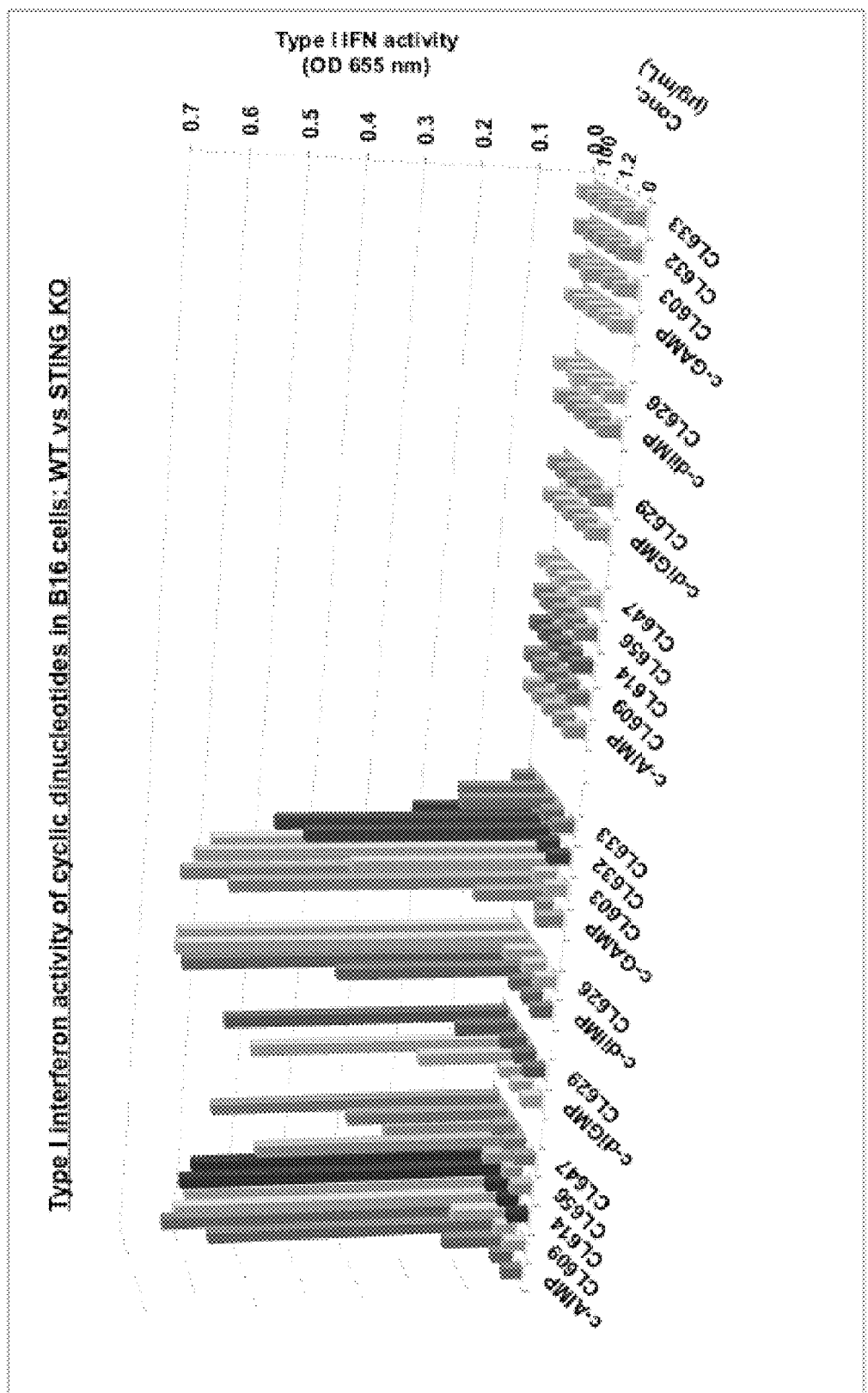
FIG. 4. In vitro Type I interferon induction activity in wild-type vs. STING knockout B16 cells. It shows relative ISG54 activity (as an indirect measurement of Type I interferon induction) of non-fluorinated vs. fluorinated cyclic dinucleotides incubated in cultures of wild-type (left-side of graph) or STING-knockout (right-side of graph) B16 cells for 24 h. WT: wild-type; SKO: STING knockout (homozygous).
Figure 5:
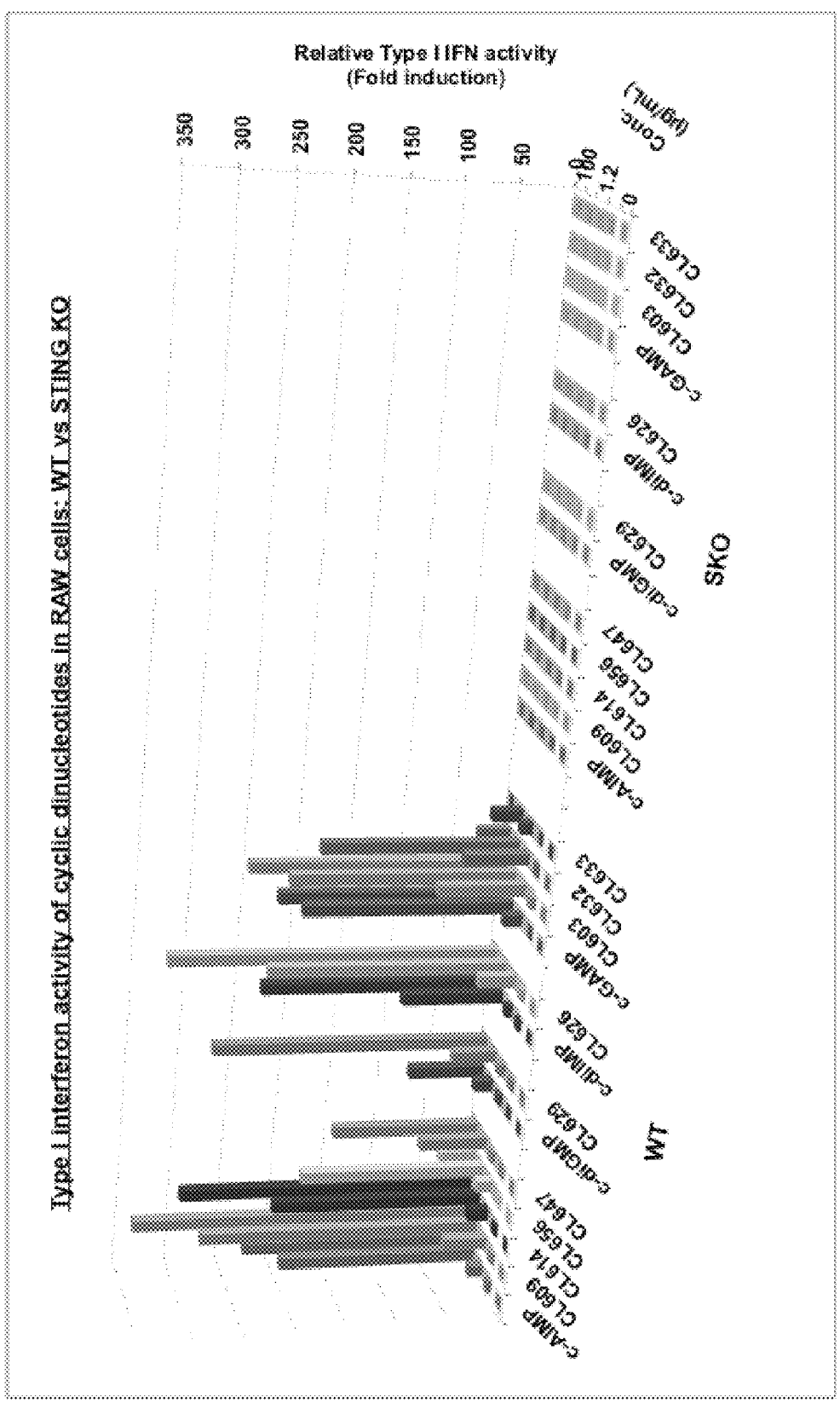

The results from this experiment are shown in FIGS. 4 and 5, which reveal three important findings. Firstly, each one of the tested cyclic dinucleotides induces production of Type I interferons in WT B16 (FIG. 4) and WT RAW (FIG. 5) cells. Secondly, none of the compounds exhibits this activity in STING knockout B16 (FIG. 4) or STING knockout RAW (FIG. 5) cells, thereby indicating that this activity requires the presence of STING.

Lastly, the majority of the fluorinated cyclic dinucleotides are more active than are the corresponding reference compounds (c-AIMP, c-diGMP, c-diIMP and c-GAMP).

In Vivo Cytokine Induction

The cyclic dinucleotides disclosed in the present invention induce cytokines in vivo in mice.

Example 2.3: Measuring Cytokine Induction in CDN-Treated Mice

Species Evaluated: Mouse
Cyclic dinucleotides tested: CL604, CL606, CL609, CL611 and CL614
Reference compound: c-AIMP and saline
Cytokines evaluated: IFN-α/β (using RAW ISG54 reporter cells) and IL-6 (by ELISA).

Twenty-one mice (Swiss; female; mean age: 8 weeks) were divided into seven groups of three: one group served as control (saline) and the other six groups were each treated with a cyclic dinucleotide (either c-AIMP, CL604, CL606, CL609, CL611 or CL614). On Day −7, blood samples for basal cytokine levels were collected from all mice and stored at −20° C. until analysis. On Day 1, the mice were treated with either 200 μL of physiologic serum (containing 0.9% NaCl) or 200 μL of a solution of a cyclic dinucleotide (dose: 10 mg/kg) in physiologic serum (containing 0.9% NaCl), by intravenous (i.v.) injection. Blood samples were collected from the mice at 4 h post-injection, and then stored at −20° C. until analysis. Cytokine induction was measured in the sera from the blood samples.

Figure 6:
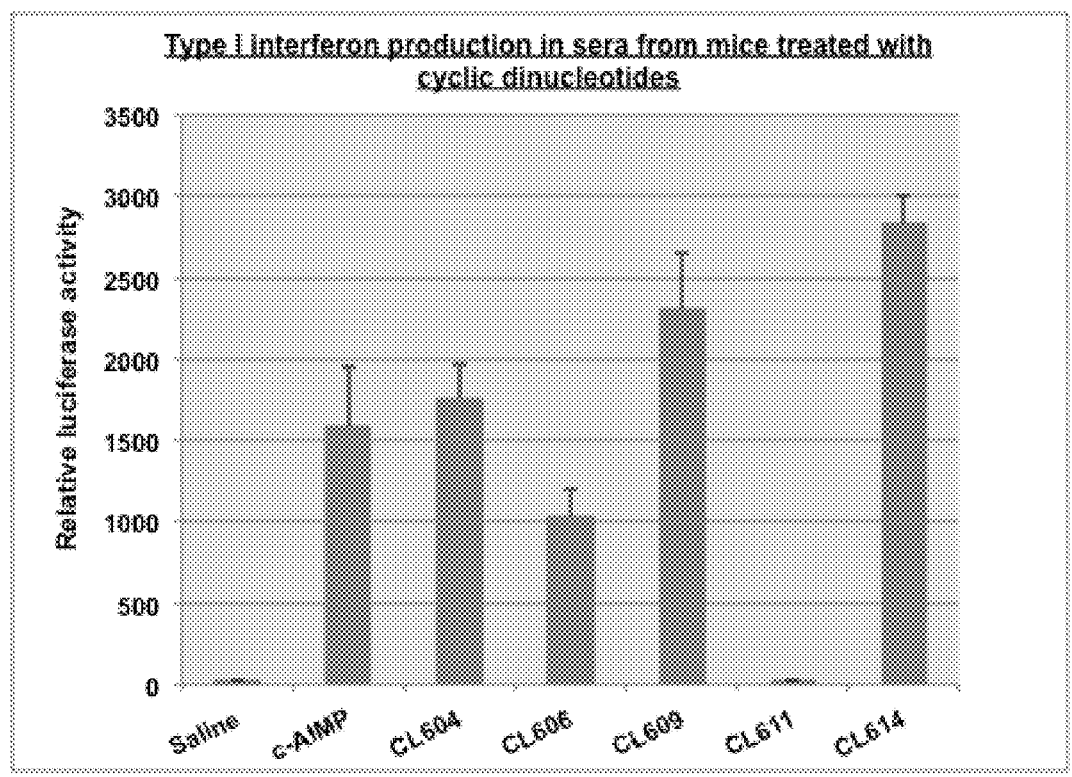
Figure 7:
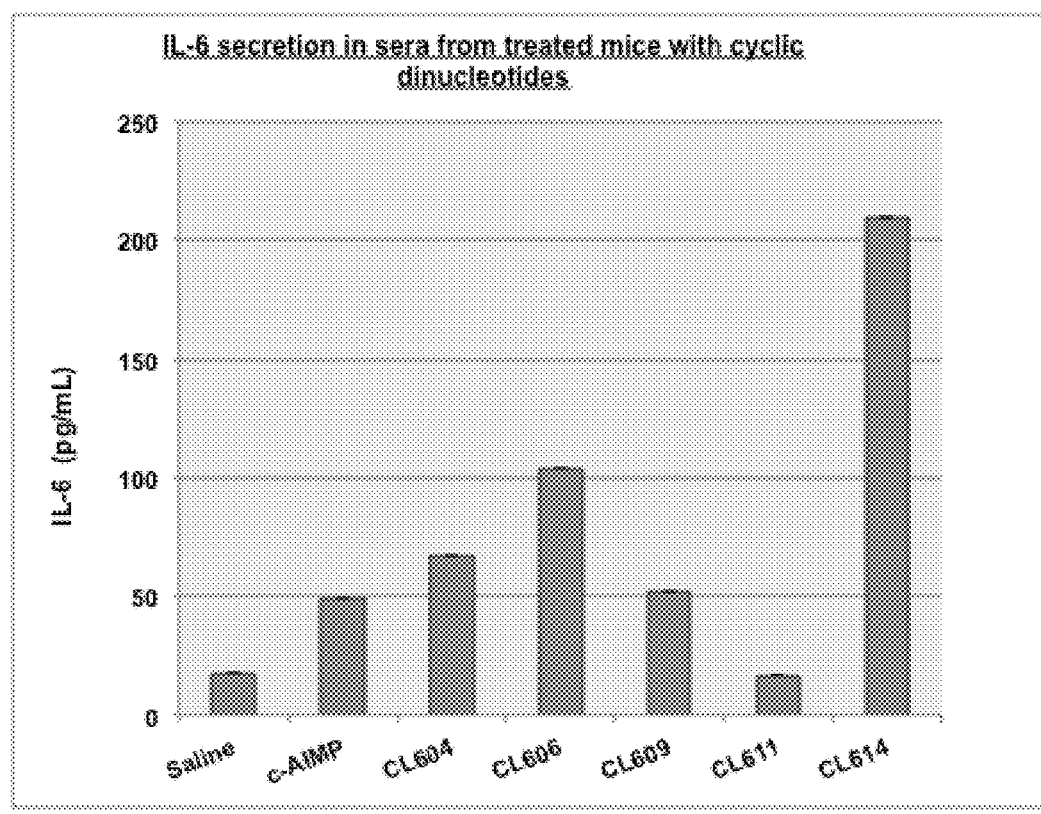

The results from this experiment are shown in FIGS. 6 and 7, which reveal two important findings: firstly, at the indicated dose, within 4 h post-treatment, all of the tested cyclic dinucleotides except CL611 strongly induced Type I interferons (FIG. 6) in mice; and secondly, all of the cyclic dinucleotides except CL611 induced IL-6 (FIG. 7).

Example 2.4: Measuring In Vivo Elimination of CDNs in Mice

We have measured the in vivo elimination of representative cyclic dinucleotides of the present invention in mice.

Cyclic dinucleotides tested: CL603, CL609, CL614, CL626 and CL656

Reference compounds: c-AIMP (manufactured by InvivoGen).

Thirty mice (C57BL/6) were divided into six groups of five. Within each group, each mouse was treated with a different cyclic dinucleotide (50 mg/kg; i.v. bolus). Each group of mice was sacrificed at a different time point post-treatment: either 2 min, 5 min, 15 min, 30 min or 1 h. Just before sacrifice, a sample of blood (500 µL) was collected. The blood samples were collected in heparin tubes, and then centrifuged. The supernatant (plasma) was stored at −20° C. until analysis. Before analysis by high performance liquid chromatography-mass spectrometry (HLPC/MS), the plasma samples were processed as follows:

Plasma: each sample was treated with methanol at a ratio of 1:4, shaken and filtered (0.22 µm). One µL of the processed sample was injected onto the HPLC/MS column.

The following HPLC gradient was used (A: 10 mM ammonium formate; B: acetonitrile; total time: 6 min): 100% A for 1 min; followed by 100% A to 100% B in 4 min; followed by 100% B for 1 min. Each cyclic dinucleotide eluted at a different time and was detected by measuring the absorbance at 254 nm.

Figure 8:
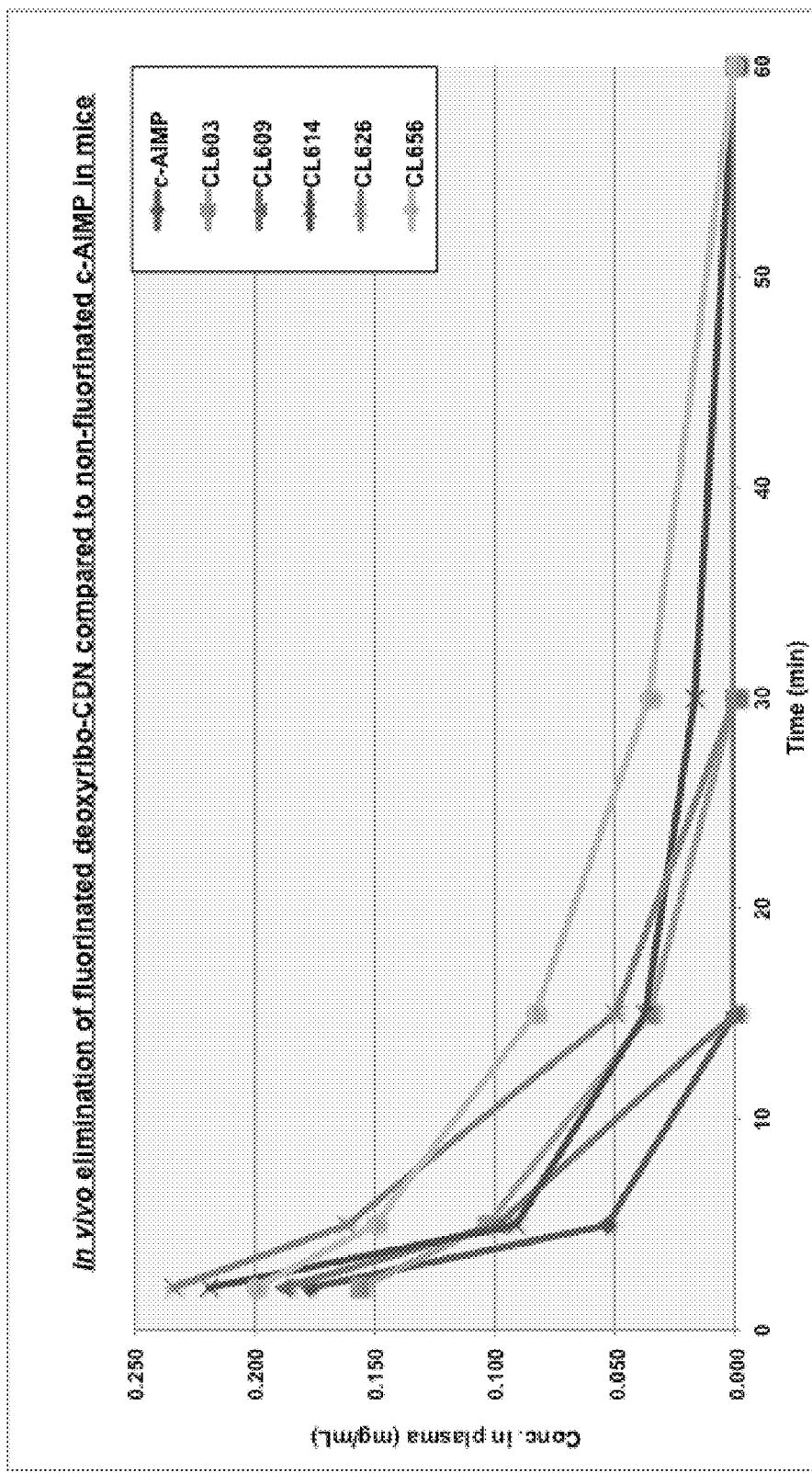

The results of this experiment are shown in FIG. 8, which reveals that the fluorinated cyclic dinucleotides were retained in the blood of mice longer than were the non-fluorinated cyclic dinucleotides.

Example 2.5: Comparison of Fluorinated and Non-Fluorinated CDNs for Their Ability to Induce Cytokines In Vitro in Whole Blood From Healthy Human Donors Reporter cell lines used: HEK-Blue™ IFN-α/β-KO-STING, HEK-Blue™ IL-1R and HEK-Blue™ TNF-α
Subject CDNs tested: CL603, CL632, CL614 and CL656
Reference (non-fluorinated) CDNs tested: c-GAMP, 2',3'-c-GAMP, c-AIMP and c-AIMP(S)
Activities evaluated: Type I IFN induction (HEK-Blue™ IFN-α/β-KO-STING), IL-1 induction (HEK-Blue IL-1R) and TNF-α induction (HEK-Blue TNF-α).

Acquisition and Handling of Human Blood Samples

Twenty human blood samples were acquired from healthy donors at the San Diego Blood Bank (3636 Gateway Center Ave, Suite 100; San Diego, Calif. 92102; U.S.A.; www.sandiegobloodbank.org). Briefly, the samples were collected by venipuncture into sodium heparin (green-cap) tubes at the time of donation, and then stored at 4° C. until pick-up. The tubes were picked up on the day of collection, stored on ice during transport, and subsequently tested with the CDNs on the same day.

Treatment and Testing of Human Blood Samples

Each blood sample was diluted (1:1) in RPMI medium and aliquoted into 96-well plates (180-µL wells) containing each CDN at six different concentrations (30 µg/mL, 10 µg/mL, 3 µg/mL, 1 µg/mL, 0.3 µg/mL and 0.1 µg/mL). The plates were incubated at 37° C. in a $CO_2$ incubator for 18 to 20 hours. The next day the supernatants were collected, transferred into the corresponding wells of round-bottom 96-well plates, and stored at −80° C. On the following day, a new 96-well plate was prepared for each of the three reporter cell lines tested, as follows: 10 µL of supernatant from the previous plate (containing the incubated CDNs and plasma) were added to the corresponding well in the new reporter cell plate. Then, a 180-µL aliquot of cells of the desired reporter cell line, previously harvested in medium containing heat-inactivated serum and counted, was added to each well (approximately 50,000 cells/well), and the plate was incubated for approximately 20 hours. The desired cytokine induction activity was determined using the QUANTI-Blue™ Assay, as previously described. Briefly, 20 µL of supernatant from the previously incubated plate was transferred to the corresponding well of a new 96-well plate in which 180 µL of QUANTI-Blue™ reagent had previously been added.

Figure 9:
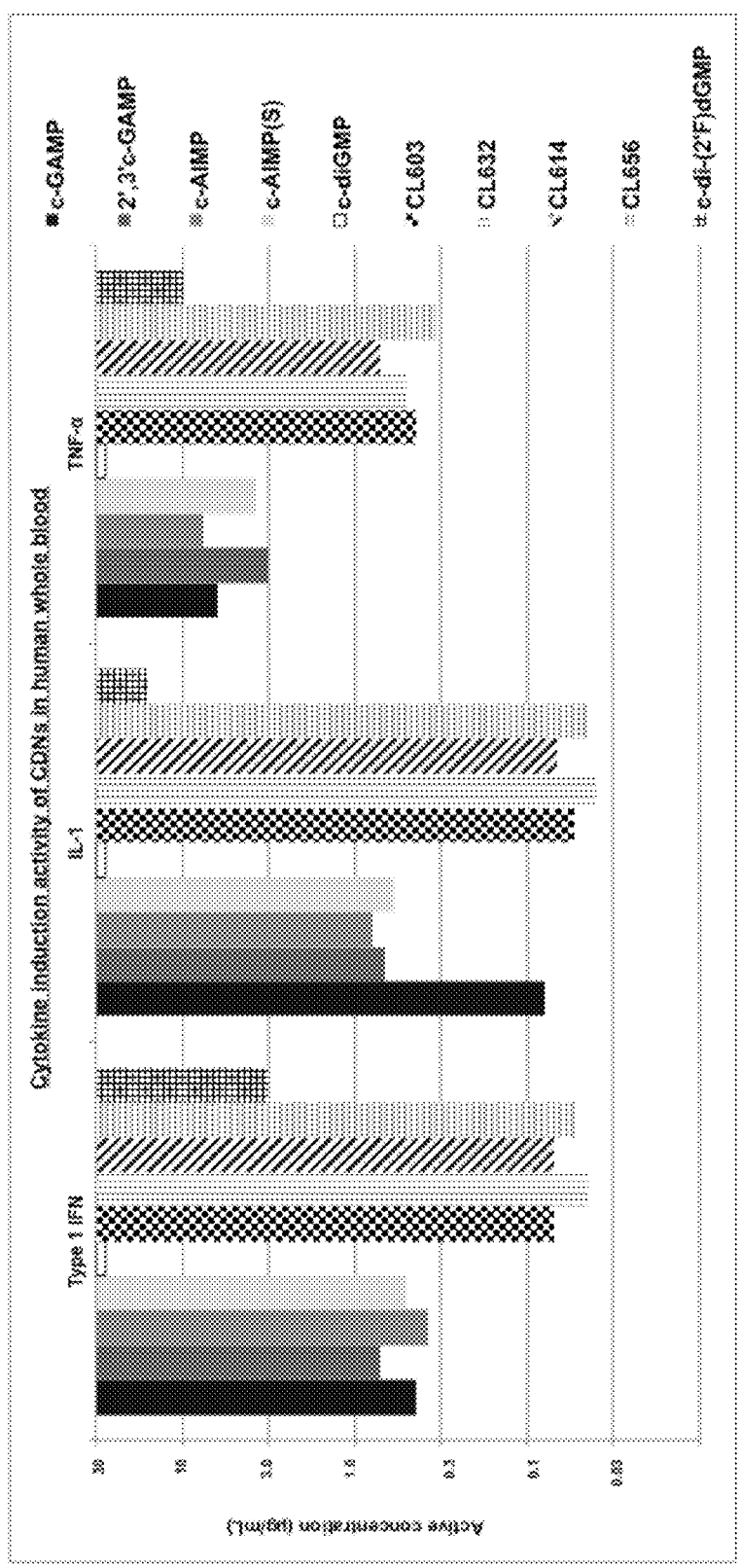
FIG. 9. Cytokine induction activity of CDNs in human whole blood.

The results from this experiment are summarized in FIG. 9, which illustrates three cytokine induction activities (Type I IFN, IL-1 and TNF-α) for representative fluorinated CDNs of the present invention and for related reference CDNs. The values shown are total averages for all 20 donors over the full concentration range tested (30 µg/mL, 10 µg/mL, 3 µg/mL, 1 µg/mL, 0.3 µg/mL, 0.1 µg/mL and 0.03 µg/mL). The activity of the CDNs is expressed in terms of "active concentration" (defined here as the CDN giving a SEAP intensity value of at least 0.5 at the indicated concentration), from the lowest of the seven tested concentrations (0.03 µg/mL) up to the highest tested concentration (30 µg/mL). The Figure reveals two principal findings: firstly, that within the tested concentration range, each one of the CDNs tested induces each one of the cytokines assessed; and secondly, that for each cytokine induction activity, each fluorinated CDN is more active than is its corresponding non-fluorinated analog (compare CL603 with c-GAMP; CL614 with c-AIMP; and CL656 with c-AIMP[s]).

Example 2.6: Comparison of Fluorinated Deoxyribo-CDNs and Non-Fluorinated Ribo-CDNs for their Resistance to Enzymatic Cleavage by SVPD or NP1, as Monitored by UHPLC-MS Enzymes used: snake-venom phosphodiesterase (SVPD) and nuclease P1 (NP1)
Subject CDNs tested: CL603, CL632, CL614 and CL656
Reference (non-fluorinated) CDNs tested: c-GAMP and c-AIMP
Property evaluated: resistance to enzymatic cleavage We incubated each CDN with either of two enzymes known to cleave nucleic acids and CDNs, and then looked for signs of degradation by UHPLC over time, by measuring the decrease in the area of the peak corresponding to the CDN (identified according to MS). Specifically, we assessed the resistance of the CDNs to snake-venom phosphodiesterase (SVPD) and nuclease P1 (NP1), both of which can degrade CDNs by cleaving the phosphodiester nucleotide linkages. The experiment was performed as follows:

Each CDN (7 µg) was separately incubated with a solution (21 µL) of either enzyme (either 160 µg SVPD in PBS buffer containing 0.6 mM $MgCl_2$; or 2.5 mU NP1 in 30 mM acetate buffer containing 2 mM $ZnCl_2$ [pH 5.3]), or with water (as control) in a water bath at 37° C. Aliquots of the reaction mixture were collected at various time points from 0 to 120 hours, heated at 100° C. for 2 min, and then frozen at 0° C. Finally, 10 µL of each aliquot was injected directly into the HPLC (Agilent 1290 Infinity UHPLC equipped with a UV-detector; column: Waters Acquity UPLC CSH $C_{18}$ 1.7 µm [2.1 mm×50 mm; flow rate: 0.3 mL/min]; detection at 254 nm; autosampler temperature: 25° C.) for analysis. The following gradient was used: 100% A (10 mM aq. ammonium formate) for 1 minute; then 100% A to 100% B (acetonitrile) over 5 minutes.

The percentage of absorbance of CDNs at each time point was calculated by dividing the peak area corresponding to the parent CDN, by the sum of all the peak areas in the chromatogram, and then multiplying by 100.

Figure 10A:
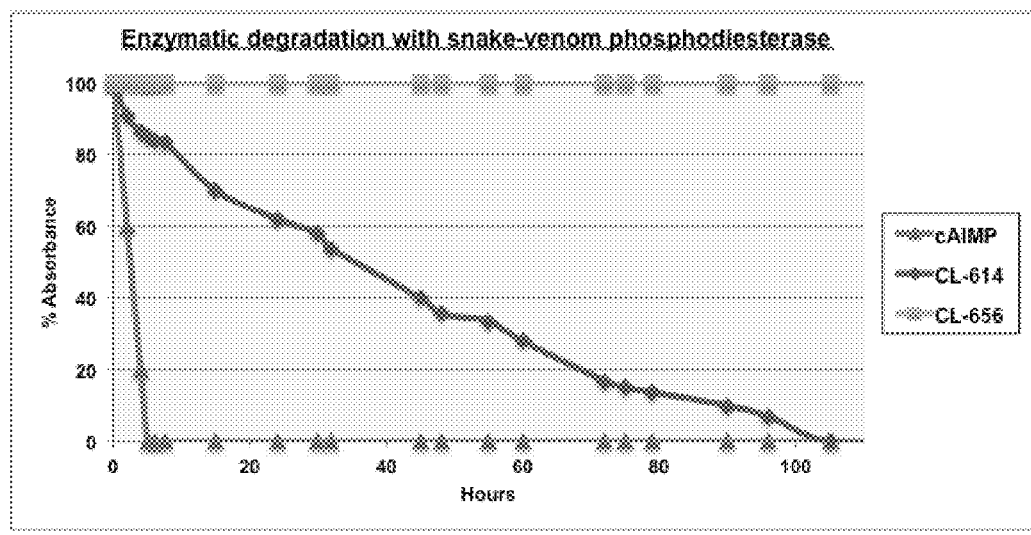
FIGS. 10 A-D. Resistance of distinct CDNs to cleavage by the enzymes SVPD and NP1 over time, as monitored by HPLC. Compare CL614 and CL656 to c-AIMP, for resistance to SVPD (A) or NP1 (B). Compare CL603 and CL656 to c-GAMP, for resistance to SVPD (C) or NP1 (D).
Figure 10B:
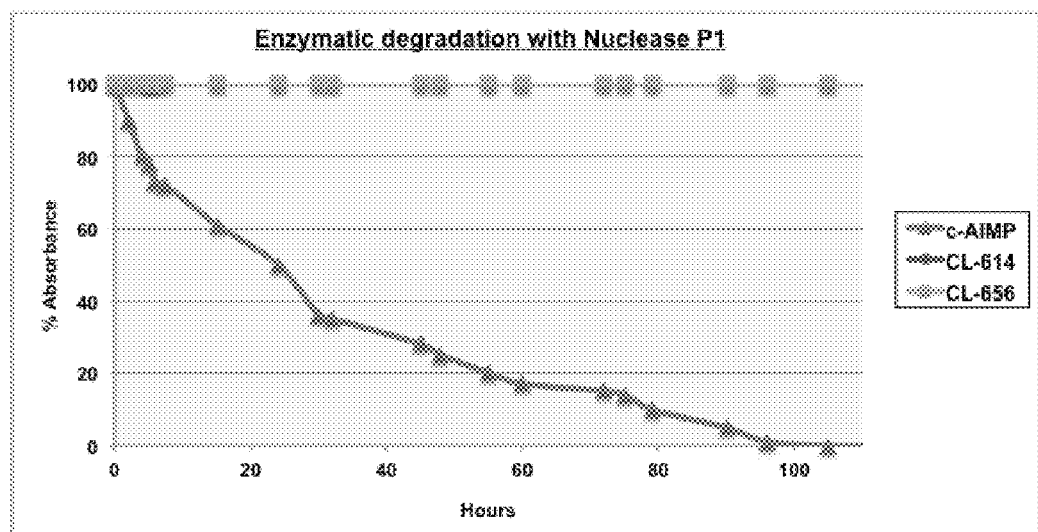
Figure 10C:
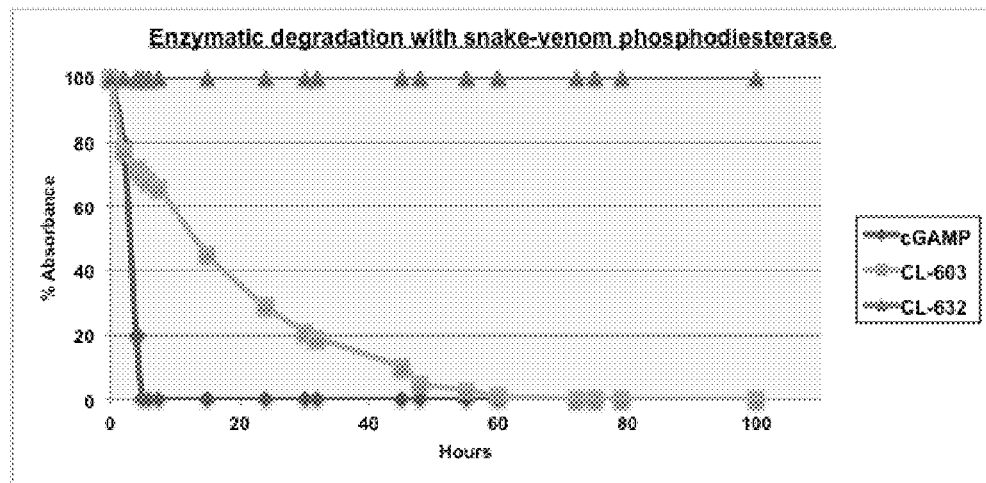
Figure 10D:
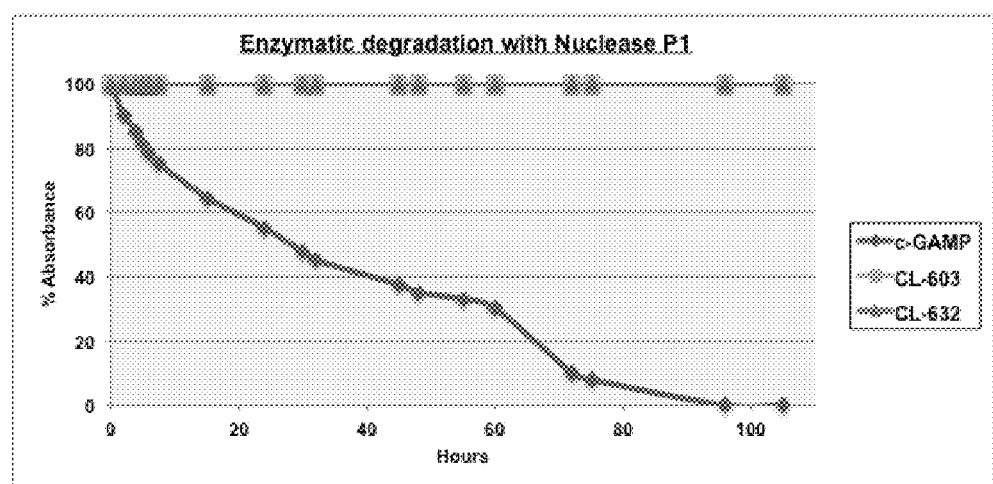

The results from this experiment are shown in FIGS. 10 A-D, which reveal two important findings: firstly, that the fluorinated deoxyribo-CDNs of the present invention are more resistant to enzymatic degradation by either enzyme than are their corresponding non-fluorinated ribo-CDN analogs (in FIGS. 10A and 10B compare CL656 or CL614 to c-AIMP, and in FIGS. 10C and 10D compare CL603 or CL632 to c-GAMP); secondly; that among the fluorinated deoxyribo-CDNs of the present invention, those containing two phosphorothioate diester linkages (CL656 and CL632) are more resistant to SVPD than are their corresponding analogs containing two phosphodiester linkages (CL614 and CL603, respectively).

Example 2.7: Comparison of the In Vitro Activity of Fluorinated Deoxyribo-CDNs and Non-Fluorinated Ribo-CDNs Before and After Exposure of These CDNs to SVPD or NP1

Reporter cell lines used: THP1-Dual™
Subject CDNs tested: CL603, CL632, CL614 and CL656
Reference (non-fluorinated) CDNs tested: c-GAMP and c-AIMP
Activities evaluated: Type I IFN induction In this experiment four representative fluorinated deoxyribo-CDNs of the present invention (CL603, CL632, CL614 and CL656) and their corresponding non-fluorinated ribo-CDN analogs (c-GAMP and c-AIMP, respectively) were compared for their relative stability to cleavage by two known CDN-cleaving enzymes: snake-venom phosphodiesterase (SVPD) and nuclease P1 (NP1). It was performed as described below.

Each CDN (7 µg) was incubated with SVPD, NP1 or water (as control), as described in Example 2.6, in a water bath at 37° C. for 2 hours, and then for 10 min at 100° C. The resulting solutions were cooled down to room temperature. An aliquot (20 µL) of each solution was then separately incubated with THP1-Dual™ cells (180 µL; concentration: 100,000 cells/well), as described in Example 2.1. ISG54 expression (as an indicator of IFN-α/β production) was quantified with QUANTI-Luc™, as explained above.

Figure 11:
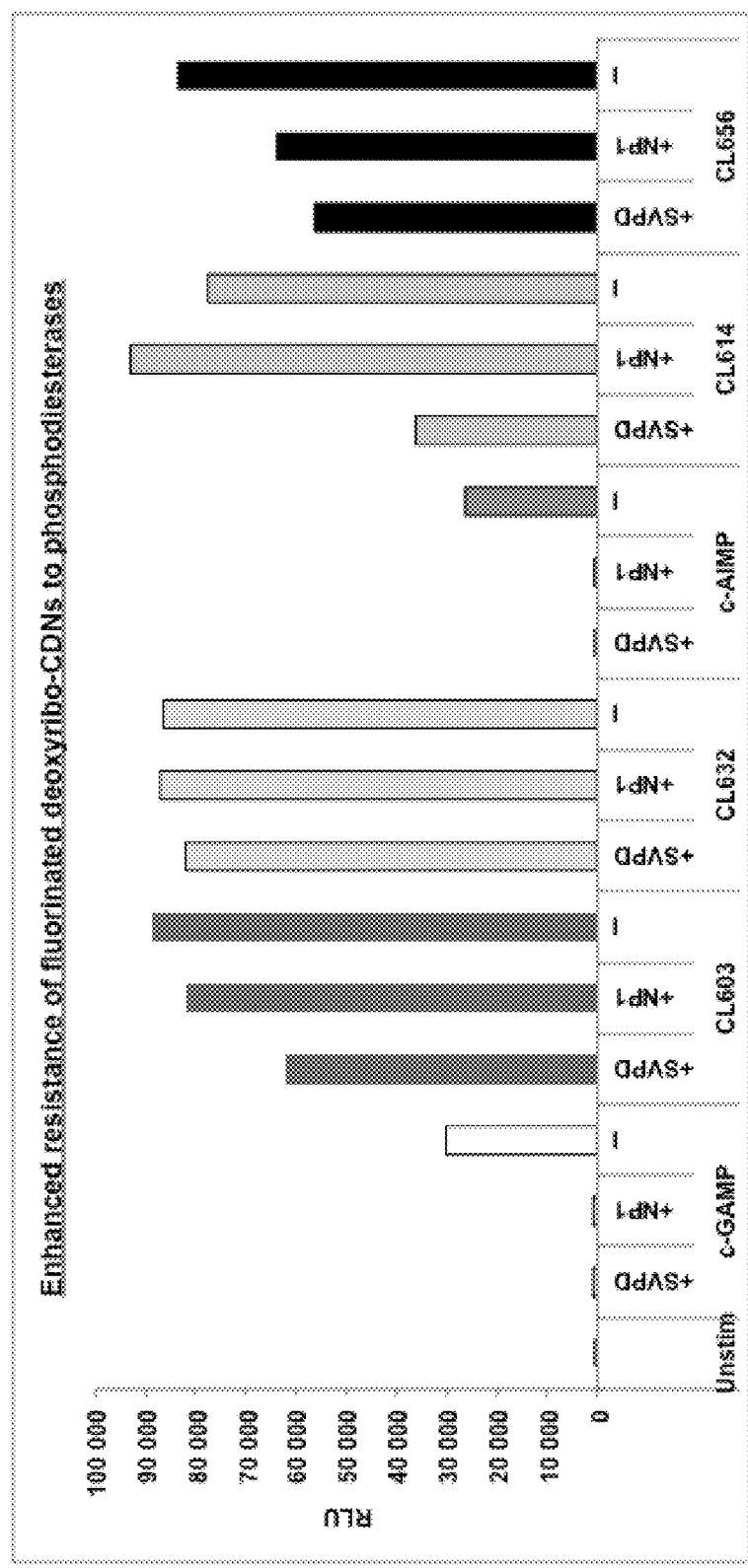
FIG. 11. In vitro activity of distinct CDNs in THP-1 Dual™ cells before and after incubation with the enzymes SVPD and NP1.

The results from this experiment are shown in FIG. 11, which reveals two important findings: firstly, before incubation with either enzyme, or after incubation with water alone (control), all of the CDNs induced ISG54 expression in the cells; and secondly, after incubation with either enzyme, the solutions corresponding to the non-fluorinated ribo-CDNs completely lost this activity, whereas those corresponding to the fluorinated deoxyribo-CDNs greatly retained this activity. These findings indicates that the fluorinated deoxyribo-CDNs are more resistant to enzymatic cleavage by SVPD or NP1 than are their corresponding non-fluorinated ribo-analogs.

Class Effects of Fluorinated Deoxyribo-Cyclic Dinucleotides

We determined that, compared to their corresponding non-fluorinated ribo-CDNs, the fluorinated deoxyribo-CDNs of the present invention surprisingly exhibit unique, unobvious and previously unreported class effects that could be exploited for therapeutic, diagnostic and research applications that involve manipulation of STING activity. For example, the fluorinated CDNs are more active, as we have ascertained in vitro by measuring cytokine induction in different cell lines and in whole blood. Moreover, they are eliminated more slowly in vivo, as we have determined in mice. Lastly, they exhibit superior resistance to enzymatic cleavage.

REFERENCES

Patent References

1. US 2015/0056224 A1
2. US 2014/0329889 A1
3. WO 2015/077354 A1
4. WO 2014/189805 A1

Non-Patent References

1. Ablasser, A., Goldeck, M., Cavlar, T., Deimling, T., Witte, G., Rohl, I., Hornung, V. (2013). cGAS produces a 2'-5'-linked cyclic dinucleotide second messenger that activates STING. *Nature,* 498(7454), 380-384.
2. Chen, H., Sun, H., You, F., Sun, W., Zhou, X., Chen, L., Jiang, Z. (2011). Activation of STAT6 by STING is critical for antiviral innate immunity. *Cell,* 147(2), 436-446.
3. Chu, C. K. (2002). *Recent Advances in Nucleosides: Chemistry and Chemotherapy*: Elsevier.
4. Danilchanka, O., & Mekalanos, J. J. (2013). Cyclic dinucleotides and the innate immune response. *Cell,* 154 (5), 962-970.
5. Diner, E. J., Burdette, D. L., Wilson, S. C., Monroe, K. M., Kellenberger, C. A., Hyodo, M., Vance, R. E. (2013). The innate immune DNA sensor cGAS produces a noncanonical cyclic dinucleotide that activates human STING. *Cell Rep,* 3(5), 1355-1361.
6. Dubensky, T. W., Jr., Kanne, D. B., & Leong, M. L. (2013). Rationale, progress and development of vaccines utilizing STING-activating cyclic dinucleotide adjuvants. *Ther Adv Vaccines,* 1(4), 131-143.
7. Fensterl, V., White, C. L., Yamashita, M., & Sen, G. C. (2008). Novel characteristics of the function and induction of murine p56 family proteins. *J Virol,* 82(22), 11045-11053.
8. Gomelsky, M. (2011). cAMP, c-di-GMP, c-di-AMP and now cGMP: bacteria use them all! *Mol Microbiol,* 79(3), 562-565.
9. Hecker, S. J., & Erion, M. D. (2008). Prodrugs of phosphates and phosphonates. *J Med Chem,* 51(8), 2328-2345.
10. Herdewijna, P. V. A. A. a. K. L. (1989). Synthesis of Nucleosides Fluorinated in the Sugar Moiety. The Application of Diethylaminosulfur Trifluoride to the Synthesis of Fluorinated Nucleosides. *Nucleosides and Nucleotides,* 8(1), 65-96.
11. Jones, R. B., N. (1995). Nucleotide prodrugs. *Antiviral Research,* 27(1-2), 1-17.
12. Li, L., Yin, Q., Kuss, P., Maliga, Z., Millan, J. L., Wu, H., & Mitchison, T. J. (2014). Hydrolysis of 2'3'-cGAMP by ENPP1 and design of nonhydrolyzable analogs. *Nat Chem Biol,* 10(12), 1043-1048.
13. Rajagopalan, P. B., F. D; Chu, C. K.; Tennant, B. C; Baldwin, B. H. (2003). *Antiviral Nucleosides: Chiral Synthesis and Chemotherapy*: Elsevier.
14. Rautio, J., Kumpulainen, H., Heimbach, T., Oliyai, R., Oh, D., Jarvinen, T., & Savolainen, J. (2008). Prodrugs: design and clinical applications. *Nat Rev Drug Discov,* 7(3), 255-270.
15. Ross, B. S. S., R. H.; Sprankle, K. G.; & Vasquez, G. (1997). An Efficient and Scalable Synthesis of Arabinosylguanine and 2'-Deoxy-2'-Fluoro-guanosine. *Nucleosides and Nucleotides*, 16(7-9), 1645-1647.
16. Schinazi, R. F. L. D. C. (2004). *Frontiers in Nucleosides & Nucleic Acids*: IHL Press.
17. Shanahan, C. A., Gaffney, B. L., Jones, R. A., & Strobel, S. A. (2013). Identification of c-di-GMP derivatives resistant to an EAL domain phosphodiesterase. *Biochemistry*, 52(2), 365-377.
18. Simm, R., Morr, M., Kader, A., Nimtz, M., & Romling, U. (2004). GGDEF and EAL domains inversely regulate cyclic di-GMP levels and transition from sessility to motility. *Mol Microbiol*, 53(4), 1123-1134.
19. Thomas, H. J., Tiwaria, K. N.; Claytona, S. J.; Secrist J. A.; & Montgomery J. A. (1994). Synthesis and Biologic Activity of Purine 2'-Deoxy-2'-fluoro-ribonucleosides. *Nucleosides and Nucleotides*, 13(1-3), 309-323.
20. Vorbrüggen, H., & Ruh-Pohlenz, C. (2001). *Handbook of Nucleoside Synthesis*. New York: Wiley.
21. Wuts, P. G. M., Greene, T. W., & Greene, T. W. (2014). *Greene's protective groups in organic synthesis* (Fifth edition/ed.). Hoboken, N.J.: John Wiley & Sons, Inc.
22. Zhang, X., Shi, H., Wu, J., Zhang, X., Sun, L., Chen, C., & Chen, Z. J. (2013). Cyclic GMP-AMP containing mixed phosphodiester linkages is an endogenous high-affinity ligand for STING. *Mol Cell*, 51(2), 226-235.

The invention claimed is:

1. A cyclic dinucleotide compound of Formula (I):

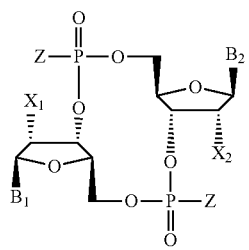

Formula (I)

wherein:

$X_1$ is H or F;

$X_2$ is H or F;

At least one among $X_1$ and $X_2$ is a fluorine atom;

Z is OH, $OR_1$, SH or $SR_1$, wherein:

i) $R_1$ is Na or $NH_4$, or ii) $R_1$ is an enzyme-labile group which provides OH or SH in vivo such as pivaloyloxymethyl;

$B_1$ and $B_2$ are bases chosen from:

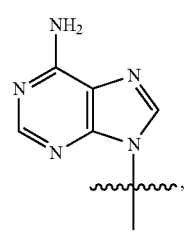

Adenine

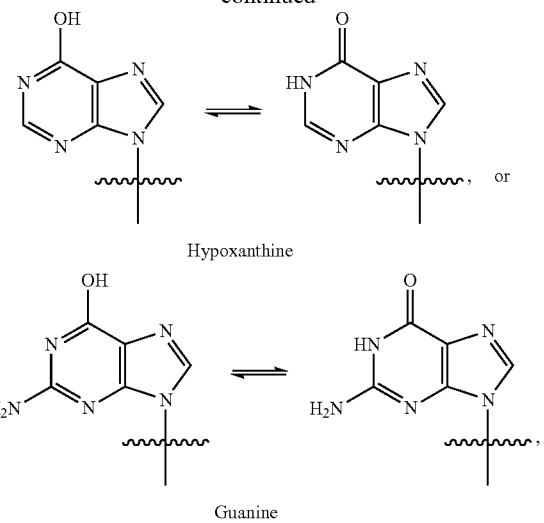

Hypoxanthine

Guanine and $B_1$ is a different base than $B_2$, or a pharmaceutically acceptable salt thereof.

2. The cyclic dinucleotide of Formula (I) according to claim 1, wherein said cyclic dinucleotide is chosen from the following compounds:

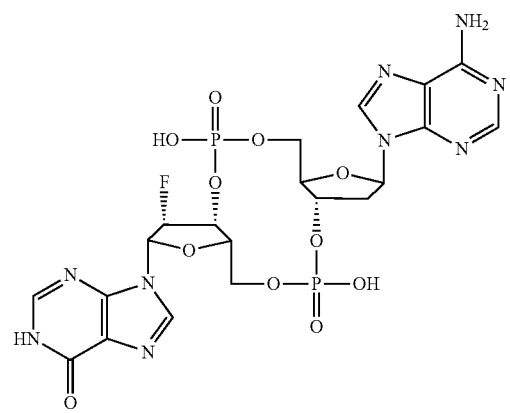

c-(dAMP-2'FdIMP)

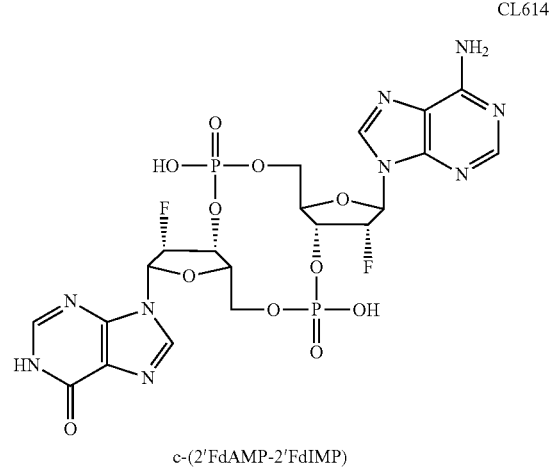

c-(2'FdAMP-2'FdIMP)

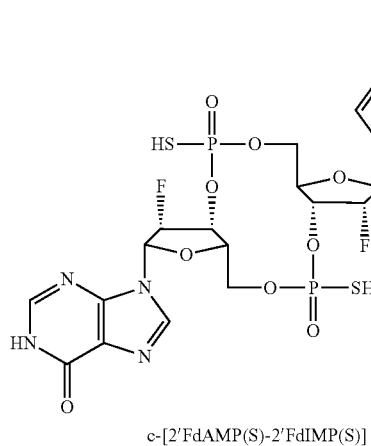

c-[2'FdAMP(S)-2'FdIMP(S)]

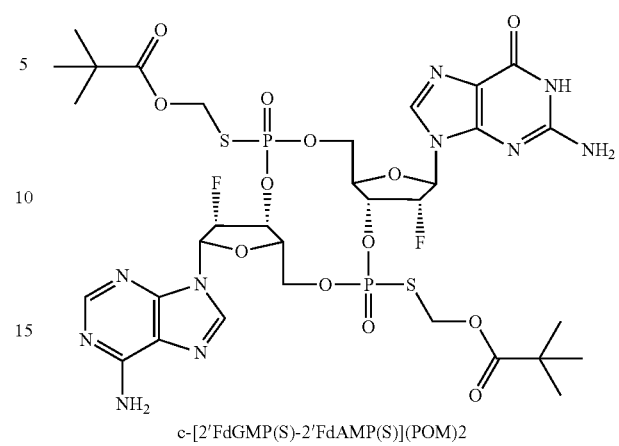

c-[2'FdGMP(S)-2'FdAMP(S)](POM)2

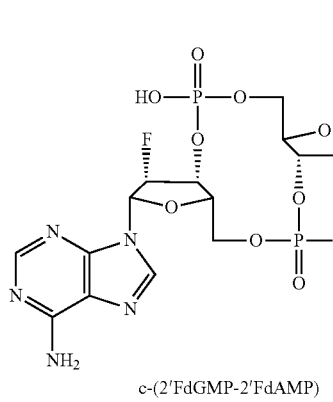

c-(2'FdGMP-2'FdAMP)

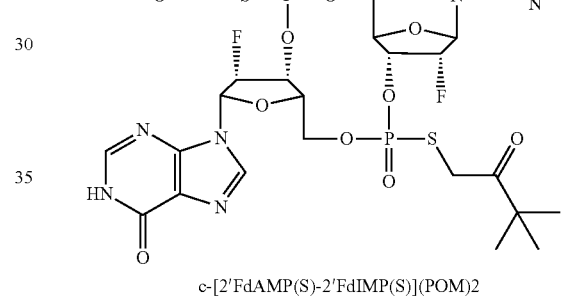

c-[2'FdAMP(S)-2'FdIMP(S)](POM)2

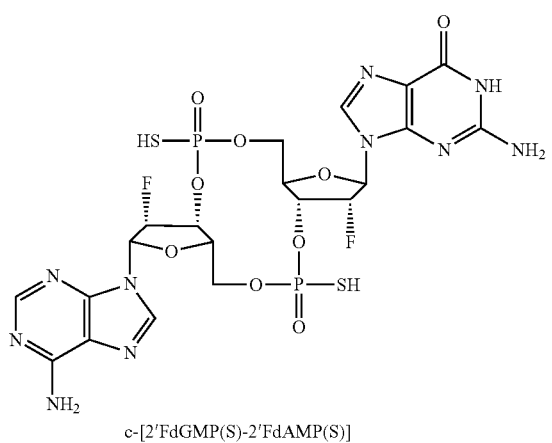

c-[2'FdGMP(S)-2'FdAMP(S)]

3. The cyclic dinucleotide of Formula (I) according to claim 1, wherein said cyclic dinucleotide is an agonist of the receptor called "stimulator of interferon genes" (STING).

4. A pharmaceutical composition comprising a cyclic dinucleotide of Formula (I) according to claim 1, and a pharmaceutically acceptable excipient.

5. A method for treating cancer comprising administering to a patient in need thereof a cyclic dinucleotide of Formula (I) according to claim 1.

6. A method for treating a bacterial infection comprising administering to a patient in need thereof a cyclic dinucleotide of Formula (I) according to claim 1.

7. A method for treating a viral infection comprising administering to a patient in need thereof a cyclic dinucleotide of Formula (I) according to claim 1.

8. A method for treating a pathology that may be alleviated by the induction of an immune response via the STING pathway comprising administering to a patient in need thereof a cyclic dinucleotide of Formula (I) according to claim 1.

9. A cyclic dinucleotide of the following formula:

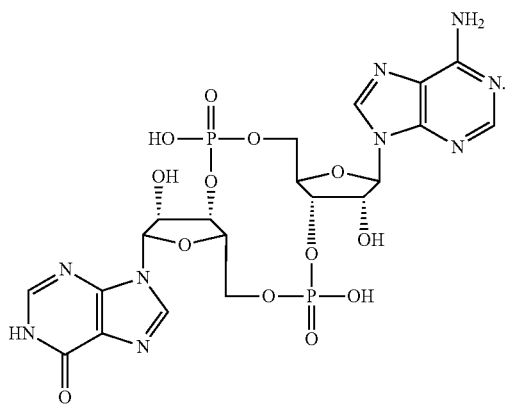 [SMILES: Nc1ncnc2c1ncn2C1OC2COP(=O)(O)O[C@@H]3C(COP(=O)(O)O[C@H]2[C@H]1O)OC(n1cnc2c(=O)[nH]cnc21)[C@@H]3O]

10. A pharmaceutical composition comprising the cyclic dinucleotide of claim 9 and a pharmaceutically acceptable excipient.

11. A method for treating cancer comprising administering to a patient in need thereof the cyclic dinucleotide of claim 9.

12. A method for treating a bacterial infection comprising administering to a patient in need thereof the cyclic dinucleotide of claim 9.

13. A method for treating a viral infection comprising administering to a patient in need thereof the cyclic dinucleotide of claim 9.

14. A method for treating a pathology that may be alleviated by the induction of an immune response via the STING pathway comprising administering to a patient in need thereof the cyclic dinucleotide of claim 9.

* * * * *

UNITED STATES PATENT AND TRADEMARK OFFICE
CERTIFICATE OF CORRECTION

PATENT NO. : 10,011,630 B2
APPLICATION NO. : 15/034335
DATED : July 3, 2018
INVENTOR(S) : Fabienne Vernejoul, Gerard Tiraby and Thierry Lioux Page 1 of 5

It is certified that error appears in the above-identified patent and that said Letters Patent is hereby corrected as shown below:

In the Specification

In Column 10, beginning at Line 38, delete:

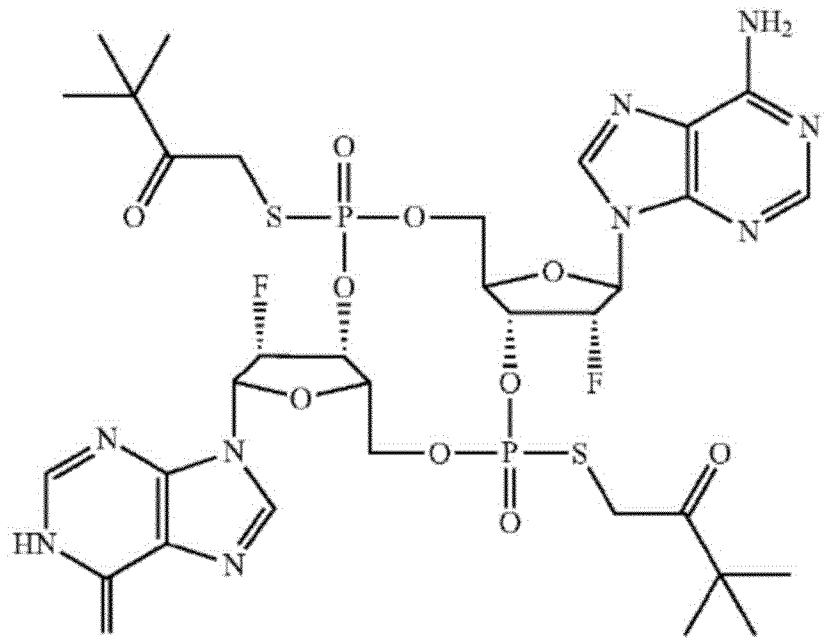

" c-[2'FdAMP(S)- 2'FdIMP(S)] (POM)$_2$ "

Signed and Sealed this
Nineteenth Day of May, 2020

Andrei Iancu
*Director of the United States Patent and Trademark Office*

And replace with:
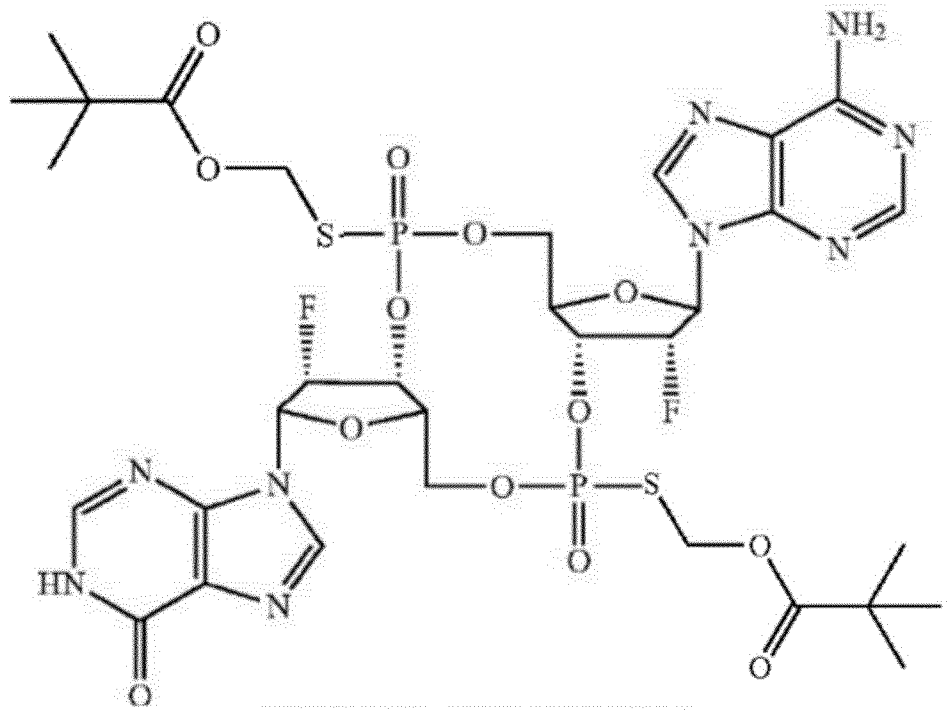
c-[2'FdAMP(S)- 2'FdIMP(S)] (POM)$_2$
In Column 64, beginning at Line 5, delete:
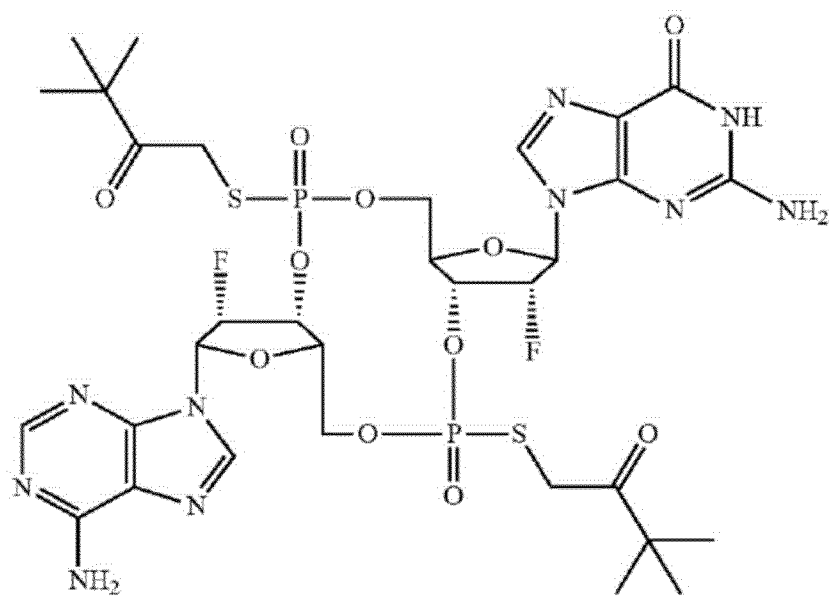
" c-(2'FdGMP(S)- 2'FdAMP(S)] (POM)$_2$ "

CERTIFICATE OF CORRECTION (continued)
U.S. Pat. No. 10,011,630 B2

And replace with:

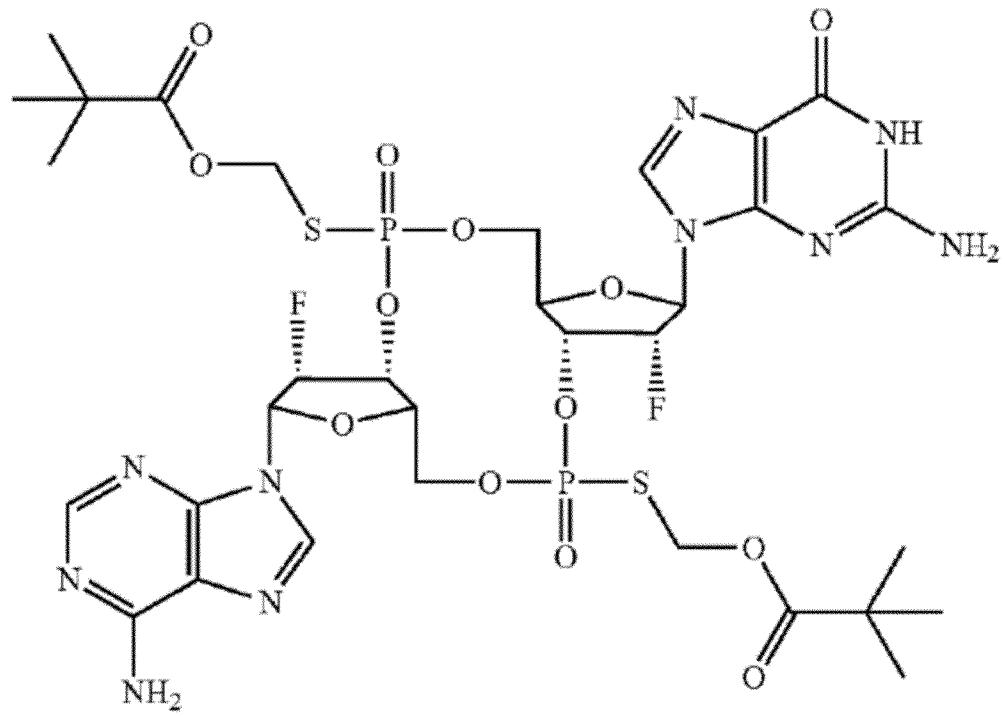

CL633 c-(2'FdGMP(S)-2'FdAMP(S)] (POM)₂

-- --

CERTIFICATE OF CORRECTION (continued)
U.S. Pat. No. 10,011,630 B2

In Column 64, beginning at Line 45, delete:

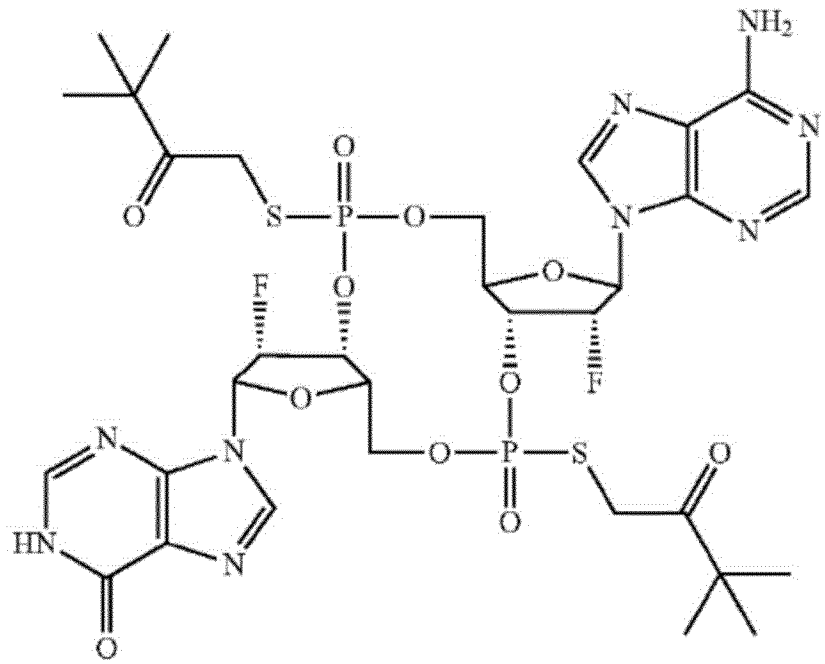

" c-[2'FdAMP(S)- 2'FdIMP(S)] (POM)₂ "

And replace with:

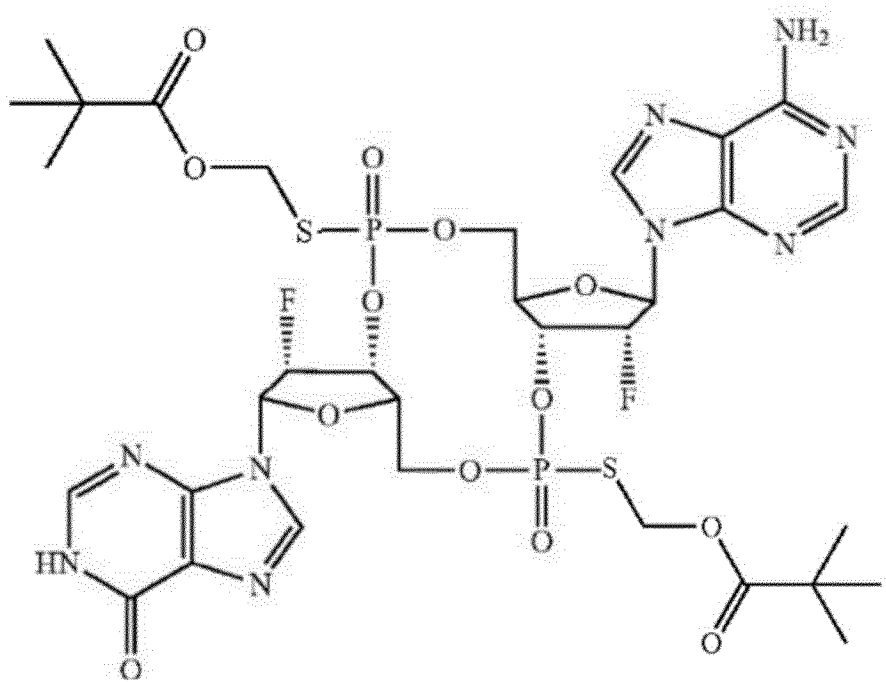

-- c-[2'FdAMP(S)- 2'FdIMP(S)] (POM)₂ --

In the Claims

In Claim 2, Column 76, beginning at Line 23, delete:
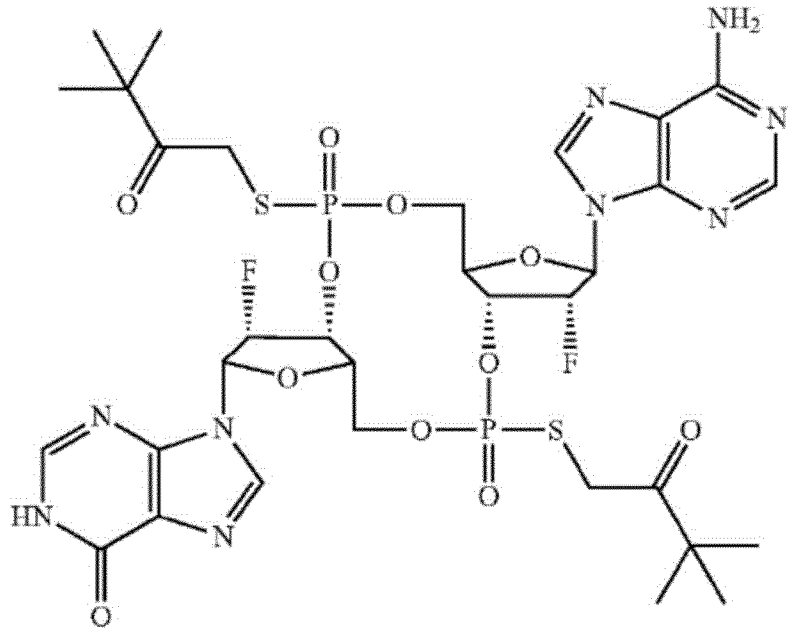
" c-[2'FdAMP(S)- 2'FdIMP(S)] (POM)₂ "
And replace with:
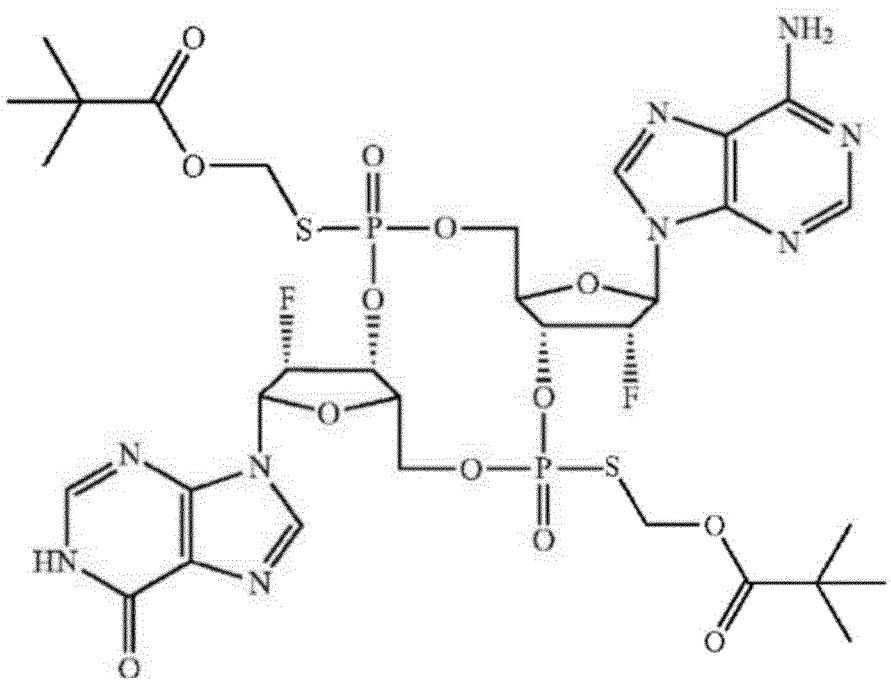
-- c-[2'FdAMP(S)- 2'FdIMP(S)] (POM)₂ --